United States Patent
Kawamura et al.

(10) Patent No.: US 9,126,943 B2
(45) Date of Patent: Sep. 8, 2015

(54) NITROGENATED HETEROCYCLIC RING DERIVATIVE AND ORGANIC ELECTROLUMINESCENT ELEMENT COMPRISING SAME

(75) Inventors: Masahiro Kawamura, Sodegaura (JP); Yuichiro Kawamura, Sodegaura (JP); Sayaka Mizutani, Sodegaura (JP); Hirokatsu Ito, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 499 days.

(21) Appl. No.: 13/389,165

(22) PCT Filed: Jan. 13, 2011

(86) PCT No.: PCT/JP2011/000156
§ 371 (c)(1),
(2), (4) Date: Feb. 6, 2012

(87) PCT Pub. No.: WO2011/086935
PCT Pub. Date: Jul. 21, 2011

(65) Prior Publication Data
US 2012/0132899 A1    May 31, 2012

(30) Foreign Application Priority Data
Jan. 15, 2010 (JP) ................. 2010-007467

(51) Int. Cl.
| H01L 51/54 | (2006.01) |
| C07D 471/04 | (2006.01) |
| C07D 213/22 | (2006.01) |
| C07D 235/18 | (2006.01) |
| C07D 235/08 | (2006.01) |
| C07D 403/04 | (2006.01) |
| C07D 401/04 | (2006.01) |
| C07D 401/14 | (2006.01) |
| C07D 403/10 | (2006.01) |
| C07D 405/04 | (2006.01) |
| C07D 519/00 | (2006.01) |
| H01L 51/00 | (2006.01) |
| H01L 51/50 | (2006.01) |

(52) U.S. Cl.
CPC ............ *C07D 235/08* (2013.01); *C07D 235/18* (2013.01); *C07D 401/04* (2013.01); *C07D401/14* (2013.01); *C07D 403/04* (2013.01); *C07D 403/10* (2013.01); *C07D 405/04* (2013.01); *C07D 471/04* (2013.01); *C07D 519/00* (2013.01); *H01L 51/0054* (2013.01); *H01L 51/0055* (2013.01); *H01L 51/0067* (2013.01); *H01L 51/0072* (2013.01); *H01L 51/5016* (2013.01); *H01L 51/5072* (2013.01); *H01L 51/5096* (2013.01)

(58) Field of Classification Search
None
See application file for complete search history.

(56) References Cited

U.S. PATENT DOCUMENTS

| 6,097,147 | A | 8/2000 | Baldo et al. |
| 6,830,828 | B2 | 12/2004 | Thompson et al. |
| 6,902,830 | B2 | 6/2005 | Thompson et al. |
| 7,001,536 | B2 | 2/2006 | Thompson et al. |
| 7,018,723 | B2 | 3/2006 | Thompson et al. |
| 7,034,454 | B2 | 4/2006 | Kawai et al. |
| 7,291,406 | B2 | 11/2007 | Thompson et al. |
| 7,537,844 | B2 | 5/2009 | Thompson et al. |
| 7,553,558 | B2 | 6/2009 | Klubek et al. |
| 7,883,787 | B2 | 2/2011 | Thompson et al. |
| 2003/0168970 | A1 | 9/2003 | Tominaga et al. |
| 2006/0017050 | A1 | 1/2006 | Hasegawa et al. |
| 2006/0035109 | A1* | 2/2006 | Arakane et al. ............... 428/690 |
| 2006/0088728 | A1 | 4/2006 | Kwong et al. |
| 2006/0097227 | A1 | 5/2006 | Okajima et al. |
| 2006/0154105 | A1* | 7/2006 | Yamamoto et al. ........... 428/690 |
| 2007/0122656 | A1 | 5/2007 | Klubek et al. |
| 2007/0122657 | A1 | 5/2007 | Klubek et al. |
| 2007/0138950 | A1* | 6/2007 | Yamamoto et al. ........... 313/504 |
| 2007/0205715 | A1 | 9/2007 | Saitoh et al. |
| 2007/0231599 | A1 | 10/2007 | Nakamura et al. |
| 2009/0001327 | A1 | 1/2009 | Werner et al. |
| 2009/0008605 | A1 | 1/2009 | Kawamura et al. |
| 2009/0009065 | A1 | 1/2009 | Nishimura et al. |
| 2009/0149649 | A1 | 6/2009 | Shin et al. |
| 2009/0218940 | A1 | 9/2009 | Okajima et al. |
| 2009/0288707 | A1 | 11/2009 | Lee et al. |
| 2010/0041171 | A1 | 2/2010 | Hasegawa et al. |
| 2010/0051106 | A1 | 3/2010 | Kim et al. |
| 2010/0096982 | A1 | 4/2010 | Eum et al. |
| 2010/0108990 | A1 | 5/2010 | Hosokawa et al. |
| 2010/0295029 | A1* | 11/2010 | Kawamura ..................... 257/40 |
| 2010/0320451 | A1 | 12/2010 | Kawamura |
| 2010/0320452 | A1* | 12/2010 | Kawamura ..................... 257/40 |
| 2011/0012504 | A1 | 1/2011 | Matsuda |
| 2011/0112296 | A1 | 5/2011 | Thompson et al. |
| 2011/0309340 | A1 | 12/2011 | Schmid et al. |
| 2012/0126205 | A1 | 5/2012 | Kawamura et al. |
| 2012/0132899 | A1 | 5/2012 | Kawamura et al. |
| 2012/0153268 | A1 | 6/2012 | Kawamura et al. |
| 2012/0286253 | A1 | 11/2012 | Schmid et al. |

FOREIGN PATENT DOCUMENTS

| CA | 2 750 408 A1 | 7/2010 |
| DE | 742 326 C | 12/1943 |
| EP | 1 582 516 A1 | 10/2005 |
| EP | 1 806 334 A1 | 7/2007 |
| EP | 2 161 319 A2 | 3/2010 |
| EP | 2 189 508 A2 | 5/2010 |
| EP | 2 189 508 A3 | 5/2010 |
| EP | 2 216 313 A1 | 8/2010 |
| EP | 2 256 176 A1 | 12/2010 |
| JP | 2001-267080 A | 9/2001 |
| JP | 2002-525808 | 8/2002 |
| JP | 2003-123983 A | 4/2003 |
| JP | 2003-142267 A | 5/2003 |
| JP | 2004-214180 | 7/2004 |
| JP | 2004-281390 A | 10/2004 |
| JP | 2005-093425 A | 4/2005 |
| JP | 2008-277810 A | 11/2008 |
| JP | 2009-91536 | 4/2009 |
| JP | 2010-59158 | 3/2010 |
| JP | 2010-199296 A | 9/2010 |
| JP | 2011-077107 A | 4/2011 |
| KR | 10-2011-0043270 A | 4/2011 |
| WO | WO 2005/105950 A1 | 11/2005 |
| WO | WO 2008/119666 A1 | 10/2008 |
| WO | WO 2009/008343 A1 | 1/2009 |
| WO | WO 2009/063833 A1 | 5/2009 |
| WO | WO 2009/063846 A1 | 5/2009 |
| WO | WO 2009063846 A1 * | 5/2009 |

| WO | WO 2009/069566 A1 | 6/2009 |
| WO | WO 2009069566 A1 * | 6/2009 |
| WO | WO 2009/107596 A1 | 9/2009 |
| WO | WO 2010/027181 A2 | 3/2010 |
| WO | WO 2010/027181 A3 | 3/2010 |
| WO | WO 2010/083869 A2 | 7/2010 |
| WO | WO 2010/114263 A2 | 10/2010 |
| WO | WO 2010/114263 A3 | 10/2010 |
| WO | WO 2013/062075 A1 | 5/2013 |
| WO | WO 2013/077352 A1 | 5/2013 |

OTHER PUBLICATIONS

Extended European Search Report issued May 13, 2013 in Patent Application No. 11732808.8.
T. Ross Kelly et al., "Progress Toward a Rationally Designed, Chemically Powered Rotary Molecular Motor", Journal of the American Chemical Society, vol. 129, No. 2, XP-0055061408, Jan. 1, 2007, pp. 376-386.
D. L. Fields et al., "Overcrowded Molecules. V 3,10-Dimethyl-1,12-bis(2-pyridyl)benzo[c]phenanthrene-2,11-diol", Journal of Heterocyclic Chemistry, vol. 10, No. 3, XP-055061415, Apr. 1973, pp. 195-199.
International Search Report issued Feb. 8, 2011, in Patent Application No. PCT/JP2011/000156.
D.Y. Kondakov, "Characterization of triplet-triplet annihilation in organic light-emitting diodes based on anthracene derivatives", Journal of Applied Physics, vol. 102, 2007, pp. 114504-1-114504-5.
Masakazu Funahashi, et al., "47.3: Highly Efficient Fluorescent Deep Blue Dopant for "Super Top Emission" Device", Society for Information Display 2008 International Symposium Digest of Technical Papers, vol. XXXIX (39), Book II, May 22-23, 2008, pp. 709-711 (with cover page).
Md. Ehesan Ali, et al., "Polyacene Spacers in Intramolecular Magnetic Coupling", The Journal of Physical Chemistry A, vol. 110, No. 49, Dec. 14, 2006, pp. 13232-13237.
Lucie Norel, et al., "Metallahelicenes: Easily Accessible Helicene Derivatives with Large and Tunable Chiroptical Properties", Angewandte Chemie, International Edition, vol. 49, No. 1, 2010, pp. 99-102.
Office Action issued Aug. 12, 2014 in European Patent Application No. 11 732 808.8.
Office Action issued Aug. 26, 2014 in Japanese Patent Application No. 2011-549945.

* cited by examiner

*Primary Examiner* — Andrew K Bohaty
(74) *Attorney, Agent, or Firm* — Oblon, McClelland, Maier & Neustadt, L.L.P.

(57) ABSTRACT

A nitrogen-containing heterocyclic derivative represented by the following formula (1):

wherein any "12-a" groups of $R_1$ to $R_{12}$ are independently a hydrogen atom, a fluorine atom, a substituted or unsubstituted aryl group having 6 to 30 ring carbon atoms or a substituted or unsubstituted heterocyclic group having 5 to 30 ring atoms; any "a" groups of $R_1$ to $R_{12}$ are independently a single bond which is bonded to $L_1$; $L_1$ is a single bond, a "b+1" valent substituted or unsubstituted hydrocarbon ring group having 6 to 30 ring carbon atoms or a "b+1" valent substituted or unsubstituted heterocyclic group having 5 to 30 ring atoms;

HAr is a substituted or unsubstituted nitrogen-containing heterocyclic group; and "a" and "b" are independently an integer of 1 to 4, and at least one of "a" and "b" is 1. Also disclosed is a nitrogen-containing heterocyclic derivative represented by the following formula (21) or (31):

(21)

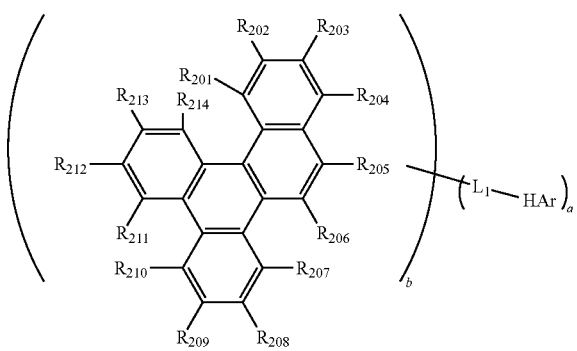

(31)

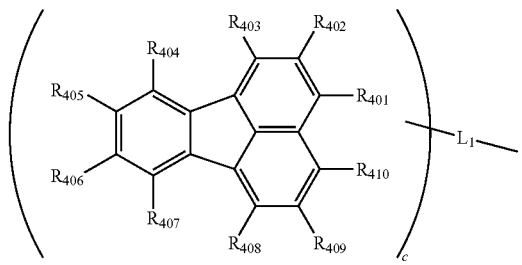

(1)

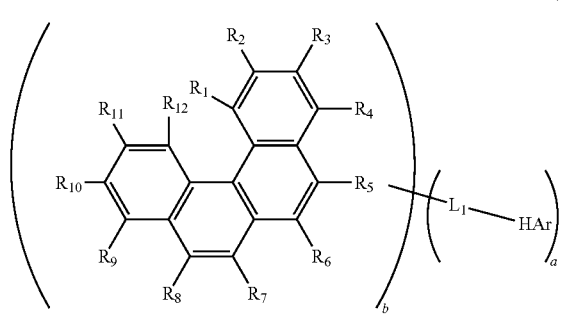

23 Claims, 1 Drawing Sheet

NITROGENATED HETEROCYCLIC RING DERIVATIVE AND ORGANIC ELECTROLUMINESCENT ELEMENT COMPRISING SAME

This application is a National Stage of PCT/JP11/000156 filed Jan. 13, 2011 and claims the benefit of JP 2010-007467 filed Jan. 15, 2010.

TECHNICAL FIELD

The invention relates to a nitrogen-containing heterocyclic derivative and an organic electroluminescence device comprising the same.

BACKGROUND ART

An organic electroluminescence (EL) device is a self-emitting device utilizing a principle that a fluorescence material emits light by energy of recombination of holes injected from an anode and electrons injected from a cathode when an electrical field is applied.

An organic EL device is provided with a pair of electrodes of an anode and a cathode, and an organic thin film layer between them. An organic thin film layer is formed of a multilayer stack of layers having their respective functions. For example, it is a multilayer stack in which an anode, a hole-injecting layer, a hole-transporting layer, an emitting layer, a blocking layer, an electron-transporting layer and an electron-injecting layer are sequentially stacked.

An organic EL device can be divided into two types according to its emission principle; i.e. a fluorescent device and a phosphorescence device. In the fluorescence organic EL device, emission utilizing singlet excitons is used, and in the phosphorescence organic EL device, emission utilizing triplet excitons is used. In the phosphorescence organic EL device, it is known that, in order to prevent diffusion of triplet excitons, which have a longer exciton life as compared with that of singlet excitons, to layers other than the emitting layer, a material having large triplet energy is used in a layer adjacent to the interface on the cathode side of the emitting layer, whereby a high efficiency is attained.

Patent Document 1 discloses a technology of increasing efficiency by providing a blocking layer formed of BCP (bathocuproine), which is a phenanthroline derivative, such that it is adjacent to the emitting layer, thereby to confine triplet excitons. Further, Patent Document 2 discloses a technology of increasing efficiency and prolonging life by using a specific aromatic ring compound in a hole-blocking layer.

On the other hand, in a fluorescence organic EL device, emission derived from triplet excitons has been recently reported (Non-Patent Documents 1 and 2, and Patent Document 3, for example).

RELATED ART DOCUMENTS

Patent Documents

Patent Document 1: JP-T-2002-525808
Patent Document 2: U.S. Pat. No. 7,018,723
Patent Document 3: JP-A-2004-214180

Non-Patent Documents

Non-Patent Document 1: Journal of Applied Physics, 102, 114504 (2007)

SUMMARY OF THE INVENTION

An object of the invention is to provide a novel nitrogen-containing heterocyclic derivative which can prevent an increase in application voltage and can attain highly-efficient emission of an organic EL device by utilizing a TTF (Triplet-Triplet Fusion) phenomenon.

Further, an object of the invention is to provide an optimum blocking material to promote TTF phenomenon.

According to the invention, the following nitrogen-containing heterocyclic derivative or the like are provided.

1. A nitrogen-containing heterocyclic derivative represented by the following formula (1):

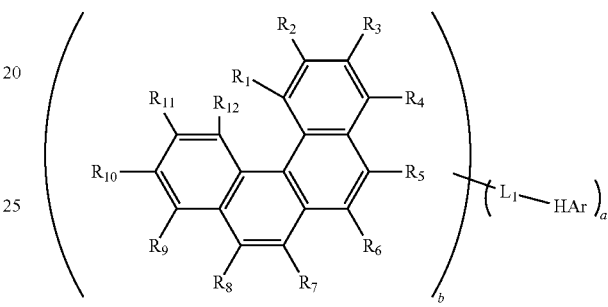

(1)

wherein any "12-a" groups of $R_1$ to $R_{12}$ are independently a hydrogen atom, a fluorine atom, a substituted or unsubstituted aryl group having 6 to 30 carbon atoms that form a ring (hereinafter referred to as the "ring carbon atoms") or a substituted or unsubstituted heterocyclic group having 5 to 30 atoms that form a ring (hereinafter referred to as the "ring atoms"); any "a" groups of $R_1$ to $R_{12}$ are independently a single bond which is bonded to $L_1$; $L_1$ is a single bond, a "b+1" valent substituted or unsubstituted hydrocarbon ring group having 6 to 30 ring carbon atoms or a "b+1" valent substituted or unsubstituted heterocyclic group having 5 to 30 ring atoms;

HAr is a substituted or unsubstituted nitrogen-containing heterocyclic group; and "a" and "b" are independently an integer of 1 to 4, and at least one of "a" and "b" is 1.

2. The nitrogen-containing heterocyclic derivative according to 1, wherein HAr is any of nitrogen-containing heterocyclic groups represented by the following formulas (2) to (6):

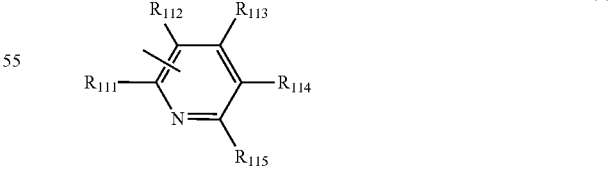

(2)

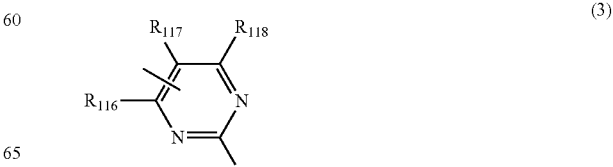

(3)

(4)
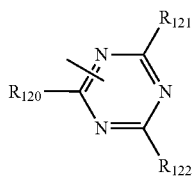

(5)
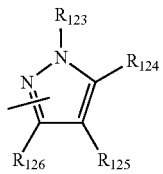

(6)
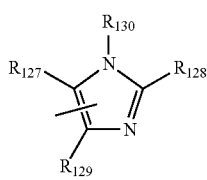

wherein $R_{111}$ to $R_{130}$ are independently a hydrogen atom or a substituent or at least two adjacent groups of $R_{111}$ to $R_{130}$ are combined to form a saturated or unsaturated ring, provided that any one of $R_{111}$ to $R_{115}$, any one of $R_{116}$ to $R_{119}$, any one of $R_{120}$ to $R_{122}$, any one of $R_{123}$ to $R_{126}$ and any one of $R_{127}$ to $R_{130}$ is a single bond and is bonded to $L_1$.

3. The nitrogen-containing heterocyclic derivative according to 1 or 2, wherein HAr is any of the nitrogen-containing heterocyclic groups represented by the following formulas (7) to (20):

(7)
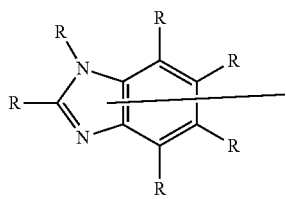

(8)
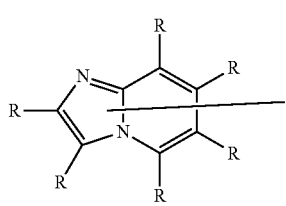

(9)
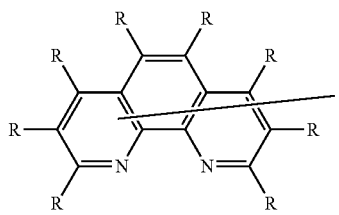

(10)
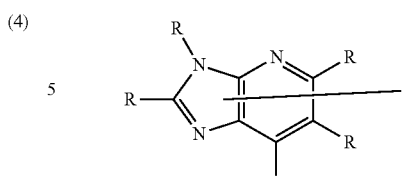

(11)
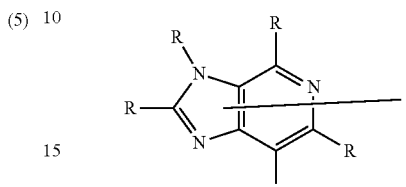

(12)
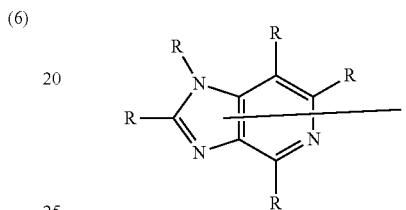

(13)
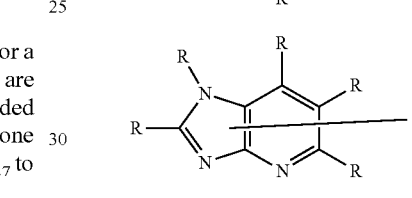

(14)
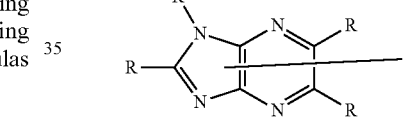

(15)
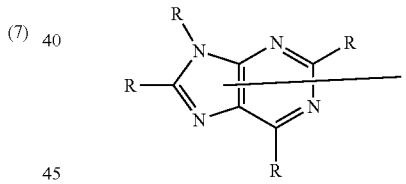

(16)
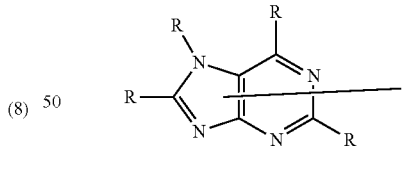

(17)
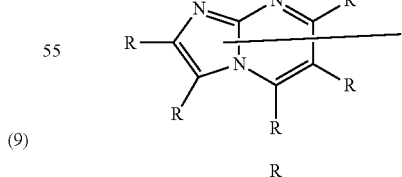

(18)
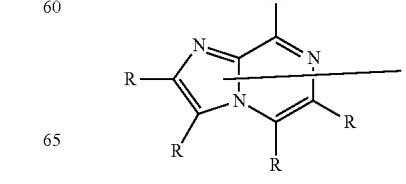

-continued

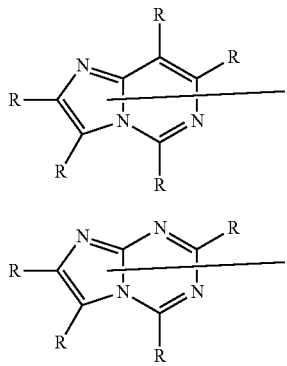

wherein any one of Rs which substitutes the heterocyclic skeleton of the formulas (7) to (20) is a single bond and is bonded to $L_1$, and other Rs are independently a hydrogen atom or a substituent or at least two adjacent groups thereof are combined to form a saturated or unsaturated ring.

4. The nitrogen-containing heterocyclic derivative according to any of 1 to 3, wherein "a" is 1 and "b" is 1

5. A nitrogen-containing heterocyclic derivative represented by the following formula (21):

(21)

[structure with $R_{201}$–$R_{214}$, $L_1$, HAr, subscripts $a$, $b$]

wherein any "14-a" groups of $R_{201}$ to $R_{214}$ are independently a hydrogen atom, a fluorine atom, a substituted or unsubstituted alkyl group having 1 to 10 carbon atoms, a substituted or unsubstituted cycloalkyl group having 3 to 8 carbon atoms, a substituted or unsubstituted alkylsilyl group having 3 to 30 carbon atoms, a substituted or unsubstituted arylsily group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms; and any "a" groups of $R_{201}$ to $R_{214}$ are independently a single bond and is bonded to $L_1$;

$L_1$ is a single bond, a substituted or unsubstituted "b+1" valent hydrocarbon group having 6 to 30 ring carbon atoms or a substituted or unsubstituted "b+1" valent heterocyclic group having 5 to 30 ring atoms;

HAr is a substituted or unsubstituted nitrogen-containing heterocyclic group; and "a" and "b" are independently an integer of 1 to 4 and at least one of "a" and "b" is 1.

6. The nitrogen-containing heterocyclic derivative according to 5, wherein HAr is any of the nitrogen-containing heterocyclic groups represented by the following formulas (2) to (6):

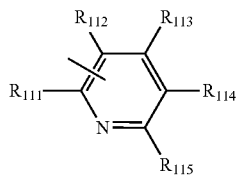

(2)

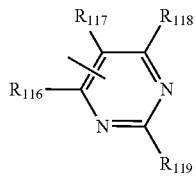

(3)

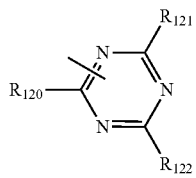

(4)

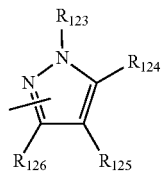

(5)

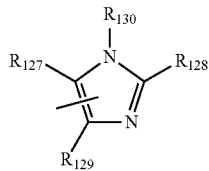

(6)

wherein $R_{111}$ and $R_{130}$ are independently a hydrogen atom or a substituent and at least two adjacent substituents of $R_{111}$ to $R_{130}$ may be combined to form a saturated or unsaturated ring; and any one of $R_{111}$ to $R_{115}$, any one of $R_{116}$ to $R_{119}$, any one of $R_{120}$ to $R_{122}$, any one of $R_{123}$ to $R_{126}$ and any one of $R_{127}$ to $R_{130}$ is a single bond and is bonded to $L_1$.

7. The nitrogen-containing heterocyclic derivative according to 5 or 6, wherein HAr is any of the nitrogen-containing heterocyclic groups represented by the following formulas (7) to (20):

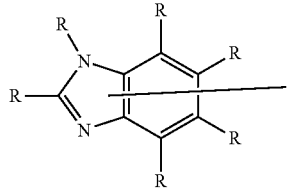

(7)

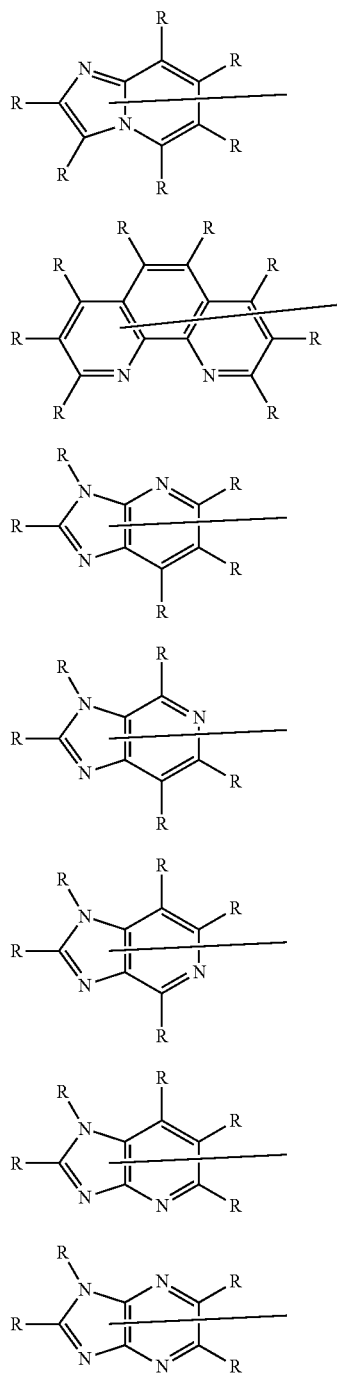

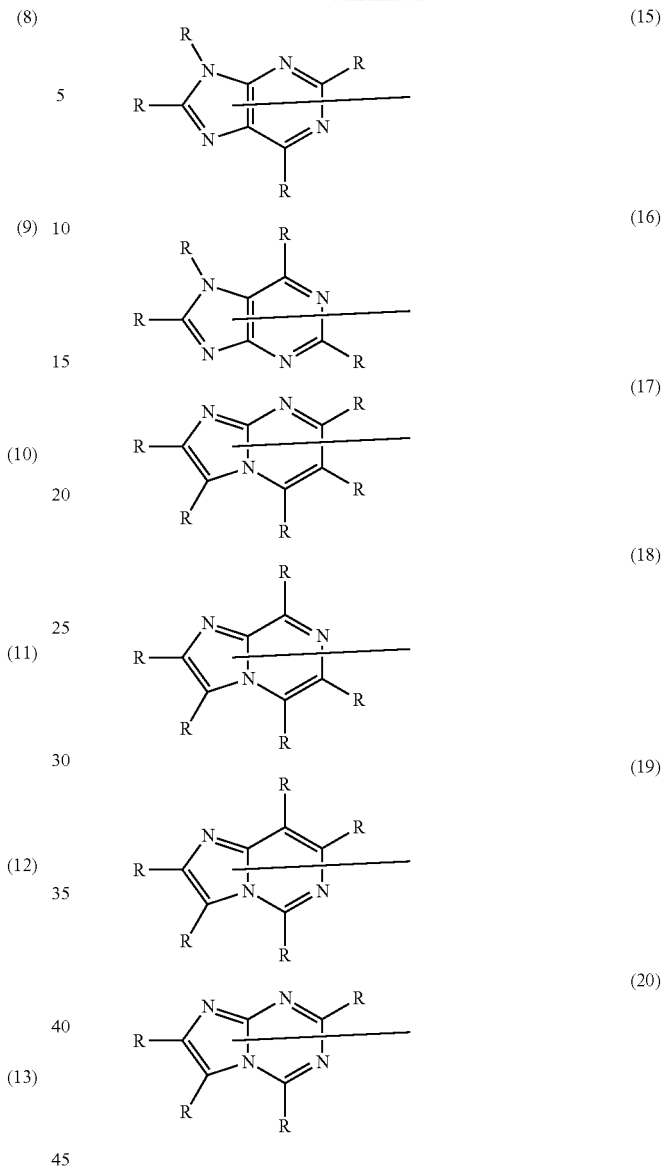

wherein any one of Rs which substitutes the heterocyclic skeleton is a single bond and is bonded to $L_1$, and other Rs are independently a hydrogen atom or a substituent or at least two adjacent groups thereof are combined to form a saturated or unsaturated ring.

8. The nitrogen-containing heterocyclic derivative according to any of 5 to 7, wherein "a" is 1 and "b" is 1.

9. A nitrogen-containing heterocyclic derivative represented by the following formula (31):

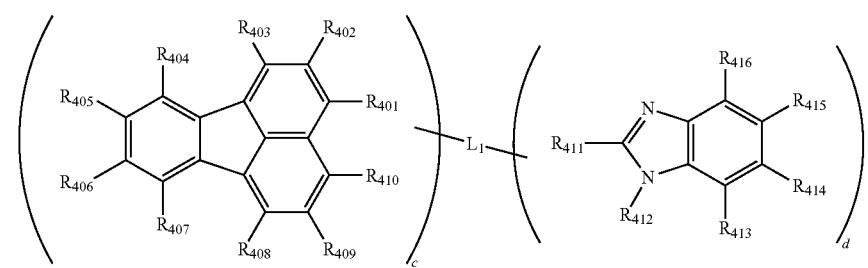

wherein $R_{401}$ to $R_{416}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted alkylamino group, a substituted or unsubstituted arylamino group, a substituted or unsubstituted aryl group having 6 to 30 ring carbon atoms or a substituted or unsubstituted heterocyclic group having 5 to 30 ring atoms; one of $R_{401}$ to $R_{410}$ and one of $R_{411}$ to $R_{416}$ is a single bond and is bonded to $L_1$; at least two adjacent substituents of $R_{411}$ to $R_{416}$ may form a saturated or unsaturated ring;

$L_1$ is a single bond, a substituted or unsubstituted "c+d" valent hydrocarbon group having 6 to 30 ring carbon atoms or a "c+d" valent heterocyclic group having 5 to 30 ring atoms; and "c" and "d" are independently an integer of 1 to 3; provided that $L_1$, and $R_{401}$ to $R_{416}$ are not an anthracene containing group.

10. The nitrogen-containing heterocyclic derivative according to 9, wherein "c" is 1.

11. The nitrogen-containing heterocyclic derivative according to 9 or 10 which is represented by the following formula (32):

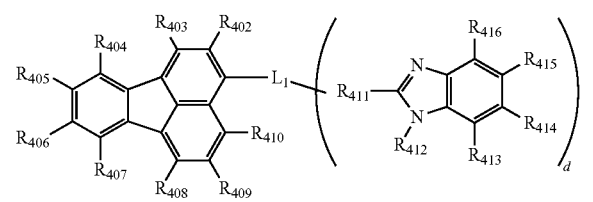

(32)

wherein $R_{402}$ to $R_{416}$, $L_1$ and d are the same groups as those in 9.

12. The nitrogen-containing heterocyclic derivative according to 11, wherein "d" is 1.

13. The nitrogen-containing heterocyclic derivative according to 12 which is represented by the following formula (33) or (34):

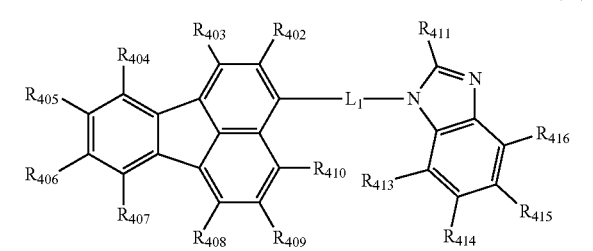

(33)

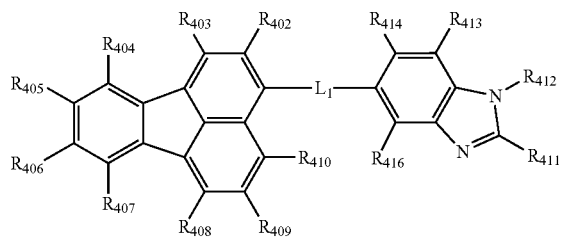

(34)

wherein $R_{402}$ to $R_{414}$, $R_{416}$ and $L_1$ are the same groups as those in 9.

14. The nitrogen-containing heterocyclic derivative according to any of 1 to 13 which is a material for an organic electroluminescence device.

15. The nitrogen-containing heterocyclic derivative according to 14, wherein the material for an organic electroluminescence device is a material for a blocking layer.

16. An organic electroluminescence device comprising an anode, an emitting layer, a blocking layer and a cathode sequentially, wherein the blocking layer comprises the nitrogen-containing heterocyclic derivative according to any of 1 to 13.

17. An organic electroluminescence device comprising an electron-injecting layer and/or an electron-transporting layer between an emitting layer and a cathode, wherein at least one layer of the electron-injecting layer and the electron-transporting layer comprises the nitrogen-containing heterocyclic derivative according to any of 1 to 13.

18. The organic electroluminescence device according to 16 or 17, wherein the emitting layer comprises an anthracene derivative represented by the following formula (41):

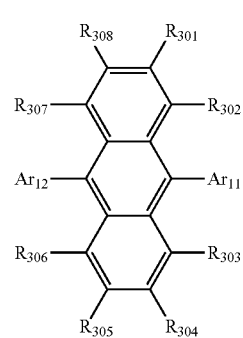

(41)

wherein $Ar_{11}$ and $Ar_{12}$ are independently a substituted or unsubstituted aryl group having 6 to 30 ring carbon atoms or a substituted or unsubstituted heterocyclic group having 5 to 30 ring atoms; and $R_{301}$ to $R_{308}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms.

19. The organic electroluminescence device according to 18, wherein the emitting layer comprising the anthracene derivative represented by the formula (41) is adjacent to the blocking layer comprising the nitrogen-containing heterocyclic derivative.

According to the invention, it is possible to provide a novel nitrogen-containing heterocyclic derivative which can prevent an increase in application voltage and can attain highly-efficient emission of an organic EL device utilizing TTF (Triplet-Triplet Fusion).

MODE FOR CARRYING OUT THE INVENTION

Figure 1:
FIG. 1 is a view showing one example of the first embodiment of the invention.

The nitrogen-containing heterocyclic derivative of the invention is represented by the following formula (1):
A nitrogen-containing heterocyclic derivative represented by the following formula (1):

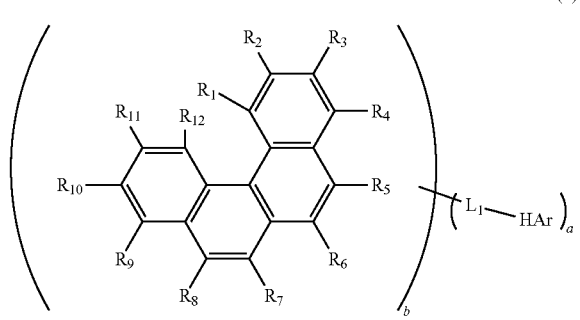

(1)

wherein any "12-a" groups of $R_1$ to $R_{12}$ are independently a hydrogen atom, a fluorine atom, a substituted or unsubstituted aryl group having 6 to 30 carbon atoms ring carbon atoms or a substituted or unsubstituted heterocyclic group having 5 to 30 ring atoms; any "a" groups of $R_1$ to $R_{12}$ are independently a single bond which is bonded to $L_1$; $L_1$ is a single bond, a "b+1" valent substituted or unsubstituted hydrocarbon ring group having 6 to 30 ring carbon atoms or a "b+1" valent substituted or unsubstituted heterocyclic group having 5 to 30 ring atoms;

HAr is a substituted or unsubstituted nitrogen-containing heterocyclic group; and "a" and "b" are independently an integer of 1 to 4, and at least one of "a" and "b" is 1.

In the formula (1), when "a" is 2 or more, the 2 or more HArs may be the same or different. Similarly, when "b" is 2 or more, the benzophenanthrene parts may be the same or different.

In the formula (1), the position at which $L_1$ is bonded to the benzophenanthrene part is preferably at $R_5$ or $R_8$. Since $R_5$ and $R_8$ are bonding positions which are highly reactive, due to the bonding of $L_1$ and $R_5$ or $L_1$ and $R_8$, the nitrogen-containing heterocyclic derivative represented by the formula (1) becomes more stable to electrons.

Further, the nitrogen-containing heterocyclic derivative of the invention is represented by the following formula (21):

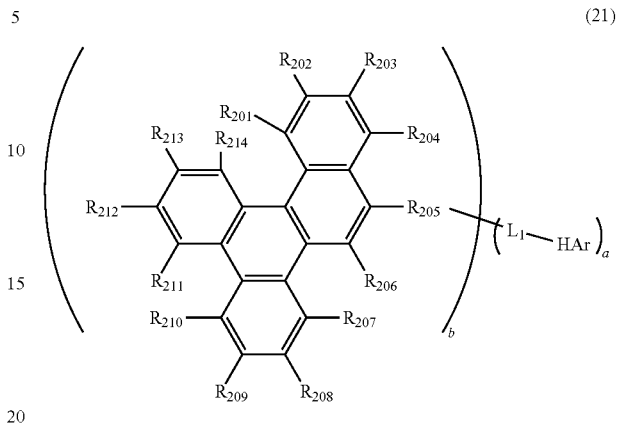

(21)

wherein any "14-a" groups of $R_{201}$ to $R_{214}$ are independently a hydrogen atom, a fluorine atom, a substituted or unsubstituted alkyl group having 1 to 10 carbon atoms, a substituted or unsubstituted cycloalkyl group having 3 to 8 carbon atoms, a substituted or unsubstituted alkylsilyl group having 3 to 30 carbon atoms, a substituted or unsubstituted arylsily group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms; and any "a" groups of $R_{201}$ to $R_{214}$ are independently a single bond and is bonded to $L_1$;

$L_1$ is a single bond, a substituted or unsubstituted "b+1" valent hydrocarbon ring group having 6 to 30 ring carbon atoms or a substituted or unsubstituted "b+1" valent heterocyclic group having 5 to 30 ring atoms;

HAr is a substituted or unsubstituted nitrogen-containing heterocyclic group; and "a" and "b" are independently an integer of 1 to 4 and at least one of "a" and "b" is 1.

In the formula (21), when "a" is two or more, two or more HArs may independently the same or different. Similarly, when "b" is two or more, the benzochrysene parts may be the same or different.

In the formula (21), the position at which $L_1$ is bonded to the benzochrysene part is preferably $R_{205}$. Since $R_{205}$ is a highly reactive bonding position, due to the bonding of $L_1$ and $R_{205}$, the nitrogen-containing heterocyclic derivative represented by the formula (21) becomes more stable to electrons.

The substituted or unsubstituted nitrogen-containing heterocyclic group represented by HAr in the formulas (1) and (21) is preferably any of the nitrogen-containing heterocyclic groups represented by the following formulas (2) to (6), more preferably any of the nitrogen-containing heterocyclic groups represented by the following formulas (7) to (20):

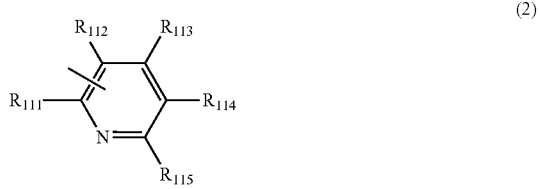

(2)

(3) 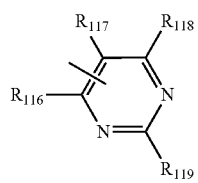
(4) 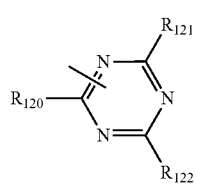
(5) 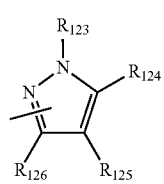
(6) 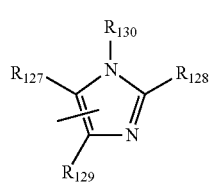
wherein $R_{111}$ to $R_{130}$ are independently a hydrogen atom or a substituent, or adjacent substituents of $R_{111}$ to $R_{130}$ are combined to form a saturated or unsaturated ring.
Any one of $R_{111}$ to $R_{115}$, any one of $R_{116}$ to $R_{119}$, any one of $R_{120}$ to $R_{122}$, any one of $R_{123}$ to $R_{126}$ and any one of $R_{127}$ to $R_{130}$ is a single bond, and is bonded to $L_1$.
(7) 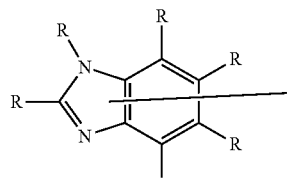
(8) 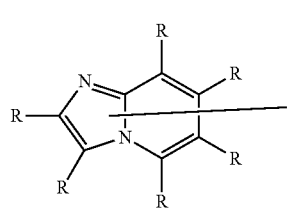
(9) 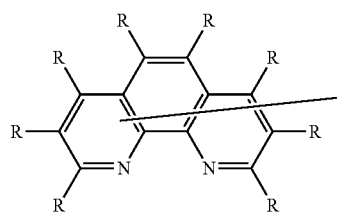
(10) 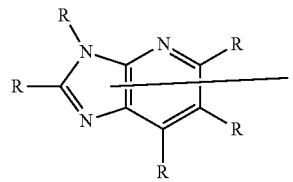
(11) 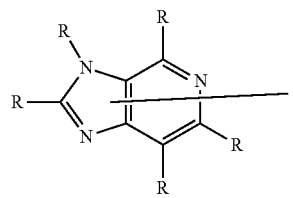
(12) 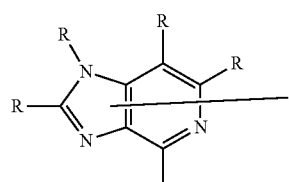
(13) 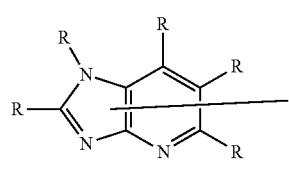
(14) 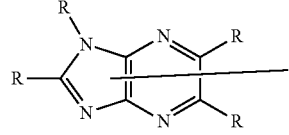
(15) 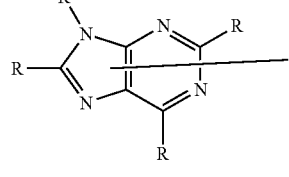
(16) 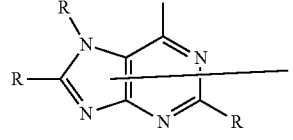
(17) 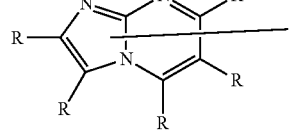
(18) 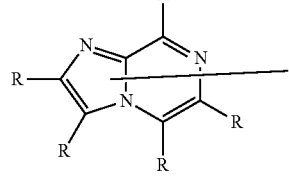

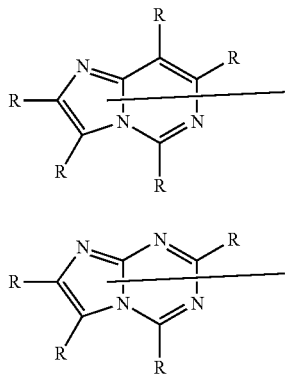
wherein any one of Rs which substitutes the heterocyclic skeleton of the formulas (7) to (20) is a single bond, and is bonded to $L_1$. Other Rs are independently a hydrogen atom or a substituent, or adjacent groups thereof may be combined to form a saturated or unsaturated ring.
Specific examples of HAr include the following nitrogen-containing heterocyclic groups.
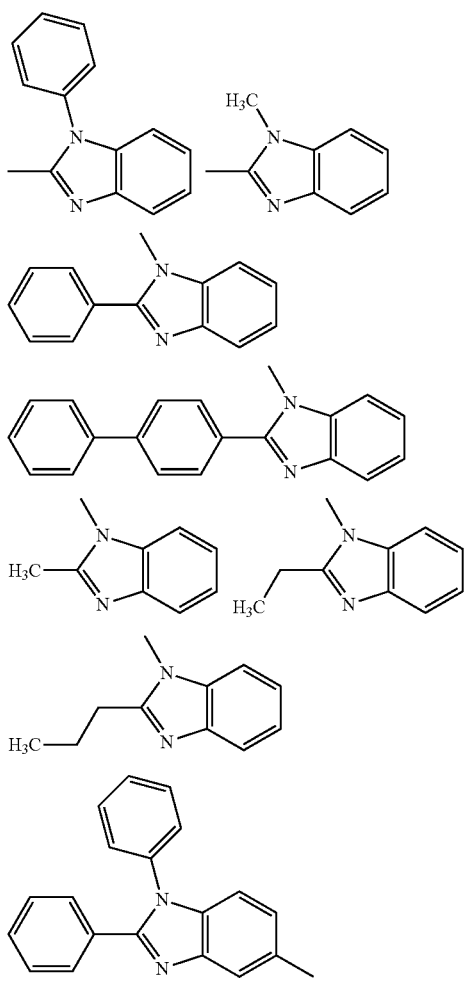
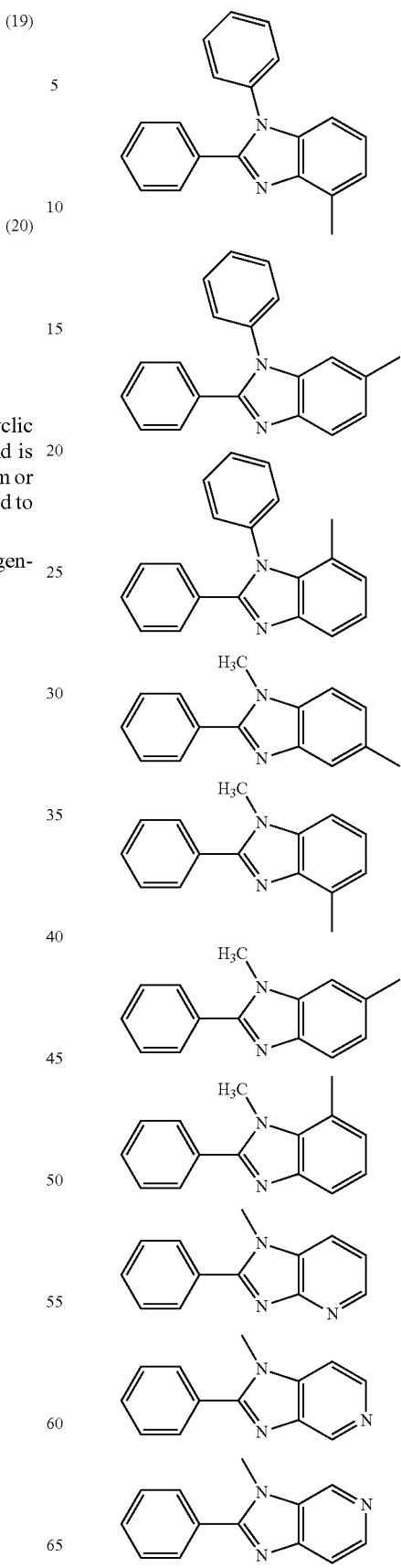

17
-continued
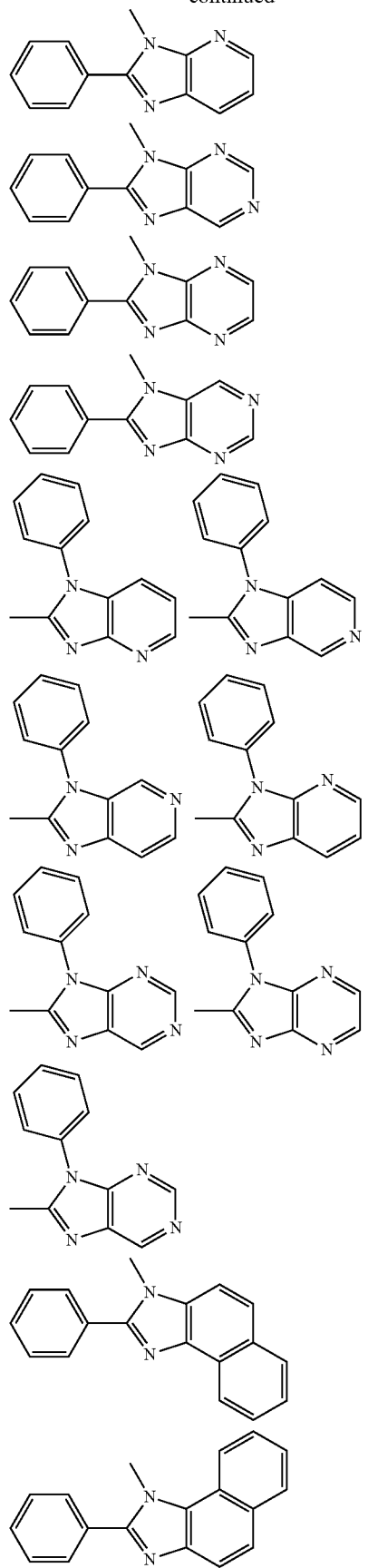
18
-continued
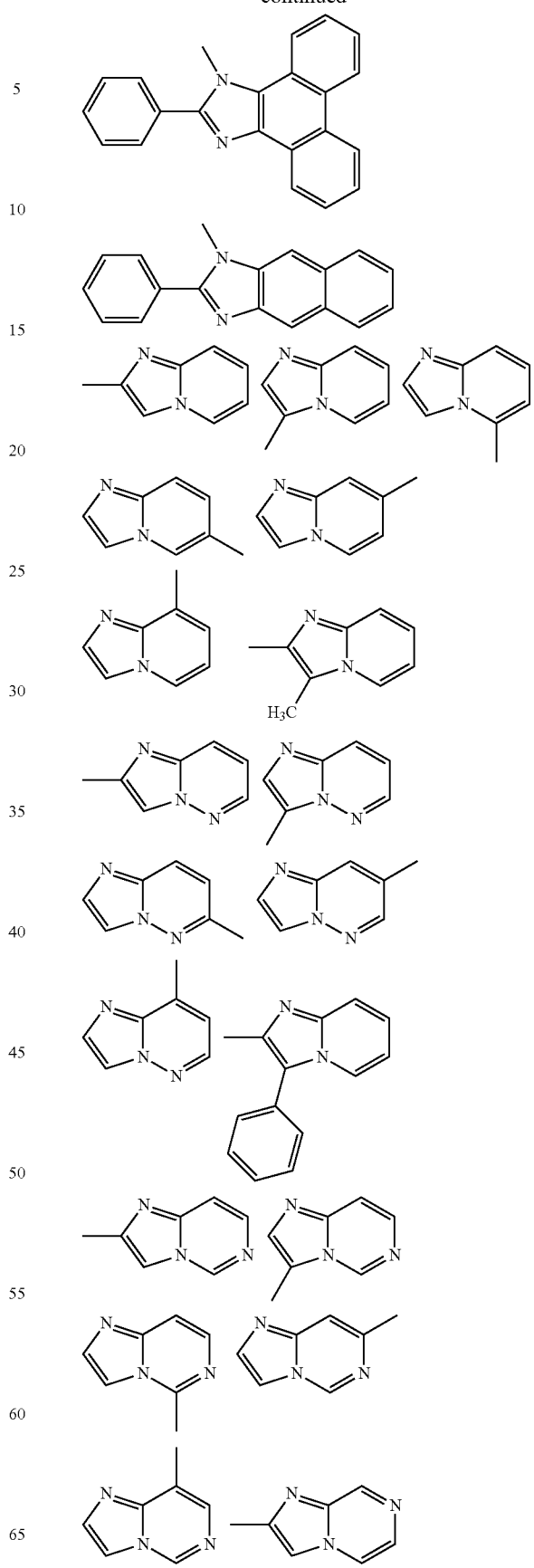

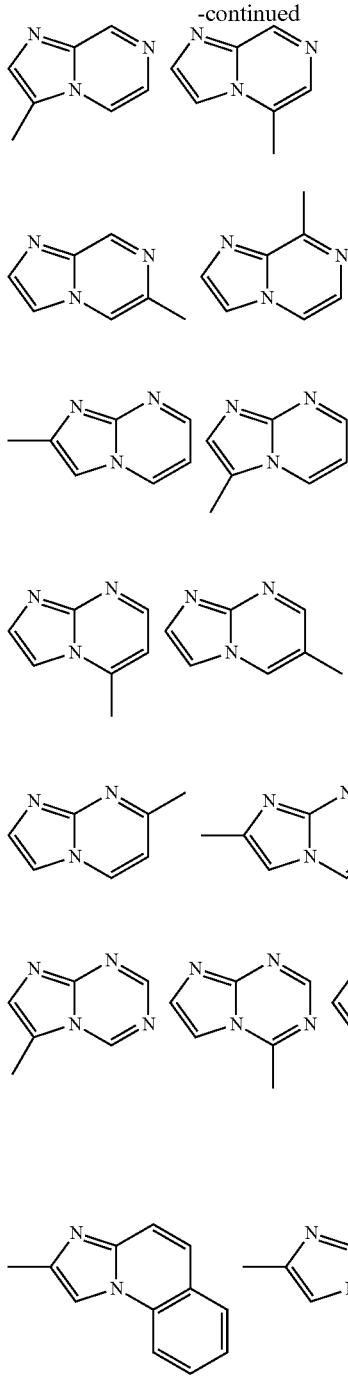
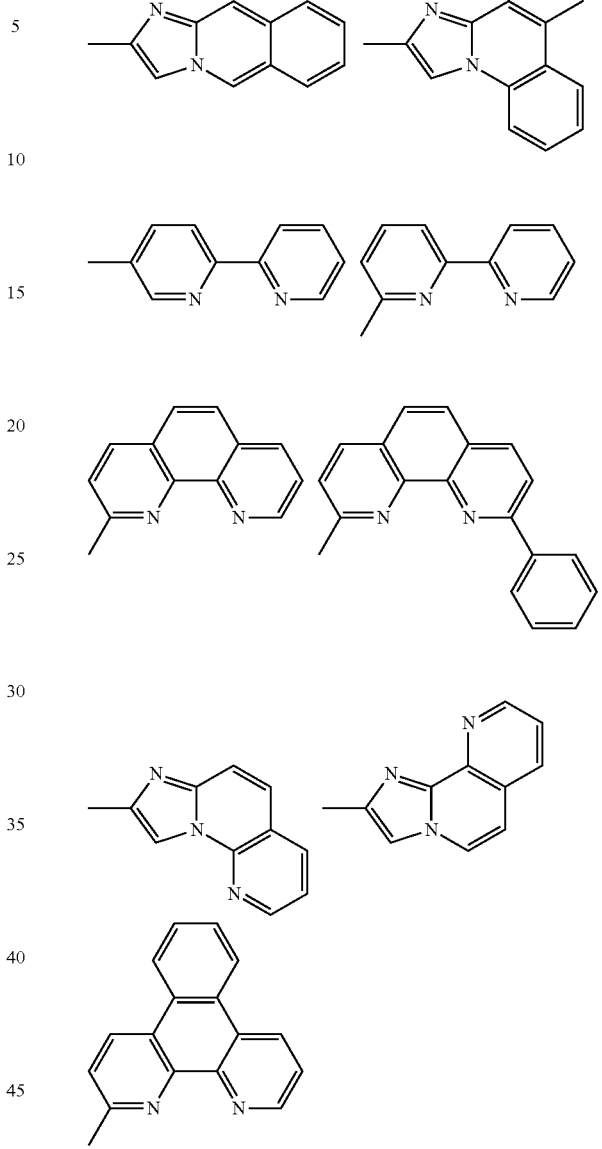
"a" and "b" in the formulas (1) and (21) is preferably a=b=1, a=2 and b=1, or a=1 and b=2, more preferably a=b=1.
The nitrogen-containing heterocyclic derivative is represented by the following formula (31):
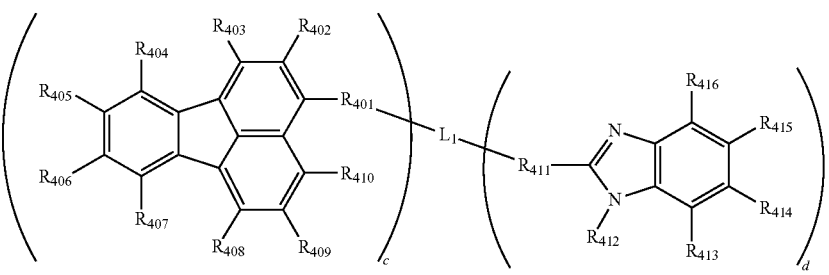
(31)

wherein $R_{401}$ to $R_{416}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted alkylamino group, a substituted or unsubstituted arylamino group, a substituted or unsubstituted aryl group having 6 to 30 ring carbon atoms or a substituted or unsubstituted heterocyclic group having 5 to 30 ring atoms; one of $R_{401}$ to $R_{410}$ and one of $R_{411}$ to $R_{416}$ is a single bond and is bonded to $L_1$; at least two adjacent substituents of $R_{411}$ to $R_{416}$ may form a saturated or unsaturated ring;

$L_1$ is a single bond, a substituted or unsubstituted "c+d" valent hydrocarbon group having 6 to 30 ring carbon atoms or a "c+d" valent heterocyclic group having 5 to 30 ring atoms; and "c" and "d" are independently an integer of 1 to 3; provided that $L_1$, and $R_{401}$ to $R_{416}$ are not an anthracene containing group.

In the formula (31), when "c" is two or more, two or more fluoranthene parts may independently be the same or different. Similarly, when "d" is two or more, the benzimidazole parts may be the same or different.

In the formula (31), "c" is preferably 1, more preferably a nitrogen-containing heterocyclic derivative represented by the following formula (32):

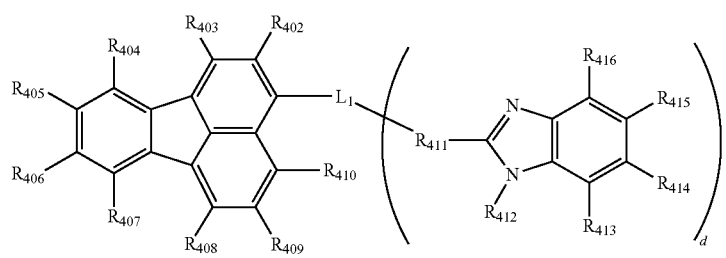

(32)

wherein $R_{402}$ to $R_{416}$, $L_1$ and d are the same groups as those in the formula (31).

In the formula (32), "d" is preferably 1, more preferably a nitrogen-containing heterocyclic derivative represented by the following formula (33) or (34):

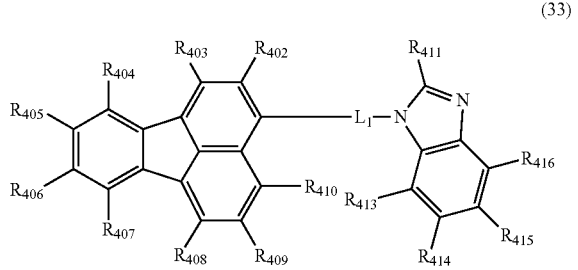

(33)

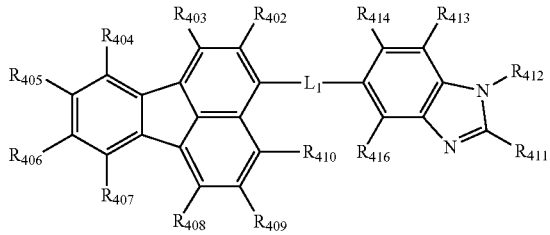

(34)

wherein $R_{402}$ to $R_{414}$, $R_{416}$ and $L_1$ are the same groups as those in the formula (31).

Each substituent of the nitrogen-containing heterocyclic derivative of the invention will be explained hereinbelow.

Examples of the aryl group having 6 to 30 ring carbon atoms represented by $R_1$ to $R_{12}$, $R_{201}$ to $R_{214}$ and $R_{401}$ to $R_{416}$ include a phenyl group, a naphthyl group, a phenanthryl group, a biphenyl group, a terphenyl group, a chryseny group, a benzophenanthryl group, a benzanthryl group, a benzochrysenyl group, a fluorenyl group and a fluoranthenyl group.

However, $R_{401}$ to $R_{416}$ do not include an anthracene ring.

Examples of the heterocyclic group having 5 to 30 ring atoms represented by $R_1$ to $R_{12}$, $R_{201}$ to $R_{214}$ and $R_{401}$ to $R_{416}$ include a pyridinyl group, a pyrazinyl group, a pyrimidyl group, a pyridazinyl group, a triazinyl group, an indolinyl group, a quinolinyl group, an acrydinyl group, a pyrrolidinyl group, a dioxanyl group, a piperidinyl group, a morpholyl group, a piperazinyl group, a carbazolyl group, a furanyl group, a thiophenyl group, an oxazolyl group, an oxadiazolyl group, a benzoxazolyl group, a thiazolyl group, a thiadiazolyl group, a benzothiaozolyl group, a triazolyl group, an imidazolyl group, a benzimidazolyl group, a benzofuranyl group and a dibenzofuranyl group.

As the alkyl group having 1 to 10 carbon atoms represented by $R_{201}$ to $R_{214}$ and $R_{401}$ to $R_{416}$, an ethyl group, a methyl group, an i-propyl group, a n-propyl group, an s-propyl group, a t-butyl group, a pentyl group, a hexyl group or the like can be given.

As the cycloalkyl group having 3 to 8 carbon atoms represented by $R_{201}$ to $R_{214}$ and $R_{401}$ to $R_{416}$, a cyclopropyl group, a cyclobutyl group, a cyclopentyl group, a cyclohexyl group, a 4-methylcyclohexyl group or the like can be given.

As the alkylsilyl group having 3 to 30 carbon atoms represented by $R_{201}$ to $R_{214}$ and $R_{401}$ to $R_{416}$, a trimethylsilyl group, a triethylsilyl group, a t-butyldimethylsilyl group, a vinyldimethylsilyl group, a propyldimethylsilyl group or the like can be given.

As the arylsilyl group having 8 to 30 ring carbon atoms represented by $R_{201}$ to $R_{214}$ and $R_{401}$ to $R_{416}$, a triphenylsilyl group, a phenyldimethylsilyl group, a t-butylphenylsilyl group, a tritolylsilyl group, a trixylylsilyl group, a trinaphthylsilyl group or the like can be given.

The alkoxy group having 1 to 20 carbon atoms represented by $R_{201}$ to $R_{214}$ and $R_{401}$ to $R_{416}$ is a group represented by —OY, and examples of Y are the same as those of the alkyl group.

The aryloxy group having 6 to 20 ring carbon atoms represented by $R_{201}$ to $R_{214}$ and $R_{401}$ to $R_{416}$ is a group represented by —OAr, and examples of Ar are the same as those of the aryl group.

The alkylamino group and the arylamino group represented by $R_{401}$ to $R_{416}$ are represented by —$NY_1Y_2$, and examples of $Y_1$ and $Y_2$ include a hydrogen atom and the same groups as those exemplified for the alkyl group or the aryl group as mentioned above. $Y_1$ and $Y_2$ may be different from each other.

As the hydrocarbon ring group having 6 to 30 ring carbon atoms represented by $L_1$, a divalent arylene group can be given, for example. A phenylene group, a naphthylene group, a biphenylene, a terphenylene group, a picenylene group, a pyrenylene group, a pentaphenylene group, a fluorenylene group, a chrysenylene group or the like can be given.

If the valence of $L_1$ is equal to or larger than trivalent, residues corresponding to the above-mentioned divalent arylene group can be given. However, $L_1$ in the formula (31) do not include an anthracene ring.

As the heterocyclic group having 5 to 30 ring atoms represented by $L_1$, if it is a divalent heterocyclic group, a pyridinylene group, a pyrazinylene group, a pyrimidinylene group, a pyridazinylene group, a triazinylene group, an indolylene group, a quinolinylene group, an acrydinylene group, a pyrrolidinylene group, a dioxanylene group, a piperidinylene group, a morpholilene group, a piperazinylene group, a carbazolylene group, a furanylene group, a thiophenylene group, an oxazolylene group, an oxadiazolyene group, a benzoxazolylene group, a thiazolylene group, a thiadiazolylene group, a benzothiazolylene group, a triazolylene group, an imidazolylene group, a benzimidazolylene group, a furanylene group, a dibenzofuranylene group or the like can be given.

When $L_1$ has a valency which is equal to or larger than trivalency, as examples of $L_1$, residues corresponding to the above-mentioned divalent heterocyclic group can be given.

As the substituent for R, a halogen atom, a hydroxyl group, a cyano group, a substituted or unsubstituted amino group, a substituted or unsubstituted alkyl group having 1 to 20 carbon atoms, a substituted or unsubstituted alkoxy group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted aryl group having 6 to 50 ring carbon atoms or a substituted or unsubstituted heterocyclic group having 5 to 50 ring atoms.

If each of substituents of $R_1$ to $R_{12}$, $R_{201}$ to $R_{214}$, $R_{401}$ to $R_{416}$, $L_1$ and HAr has a further substituent, as such a further substituent, the alkyl group, the alkylsilyl group, the halogenated alkyl group, the aryl group, the cycloalkyl group, the alkoxy group, the heterocyclic group, the aralkyl group, the aryloxy group, the arylthio group, the alkoxycarbonyl group, the halogen atom, the hydroxyl group, the nitro group, the cyano group, the carboxyl group, the dibenzofuranyl group, the fluorenyl group or the like, as mentioned above, can be given.

As for each substituent of the nitrogen-containing heterocyclic derivative of the invention, the "unsubstituted" means that the group is substituted by a hydrogen atom. The hydrogen atom of the nitrogen-containing heterocyclic derivative of the invention includes protium and deutrium.

Specific examples of the nitrogen-containing heterocyclic derivative of the invention represented by the formulas (1), (21) and (31) are given below.

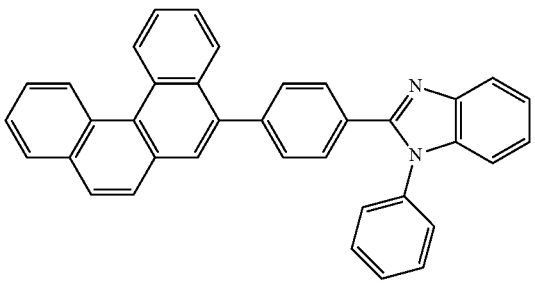

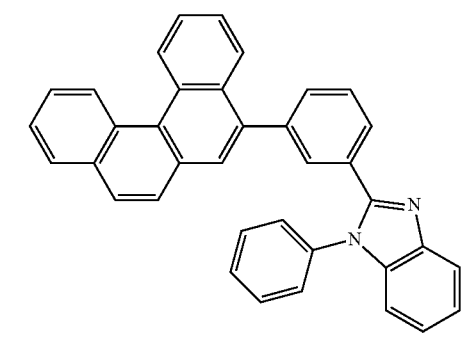

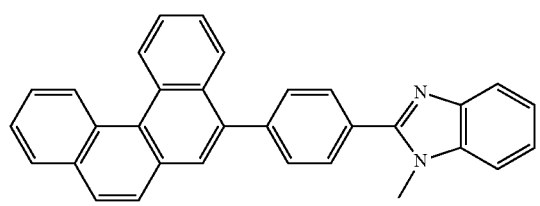

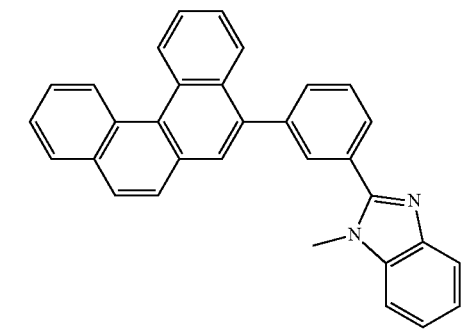

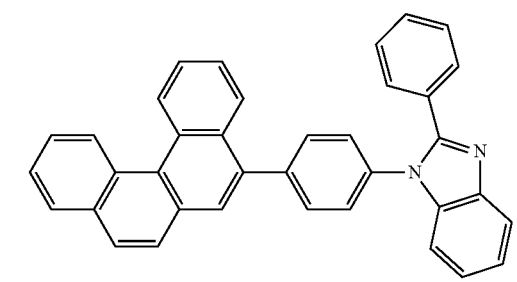

-continued
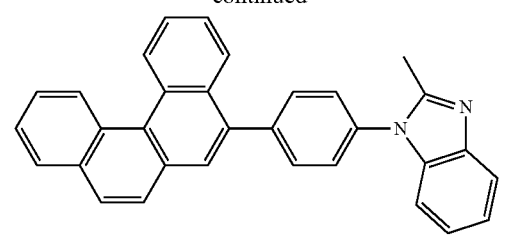
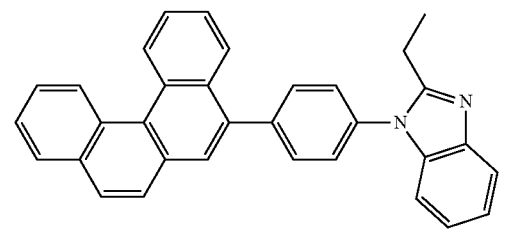
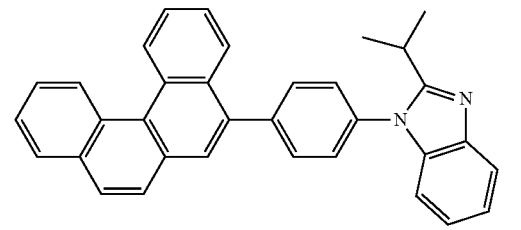
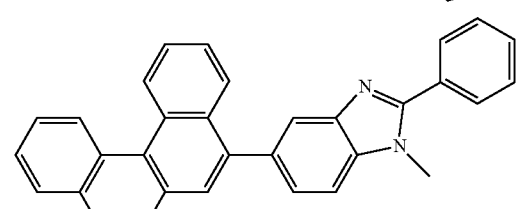
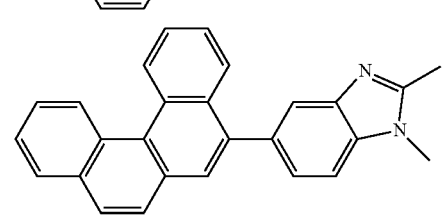
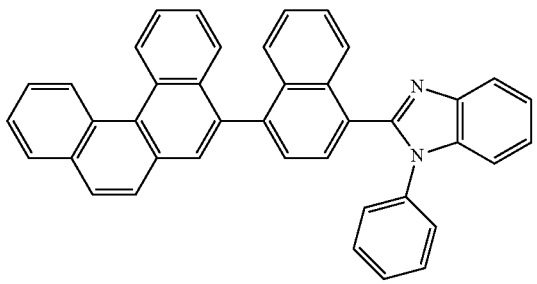
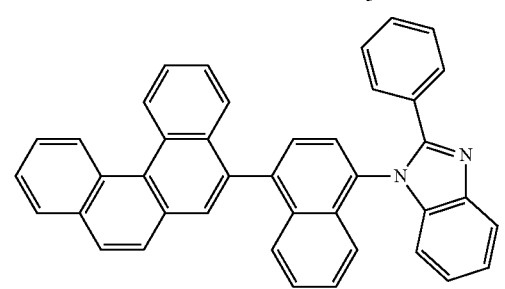
-continued
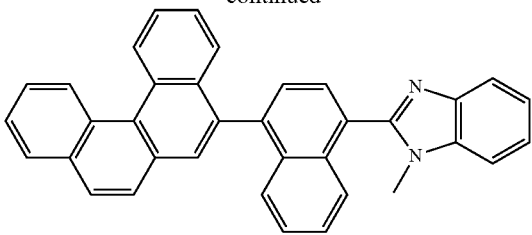
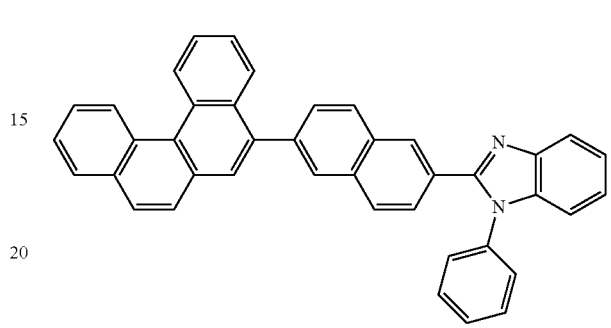
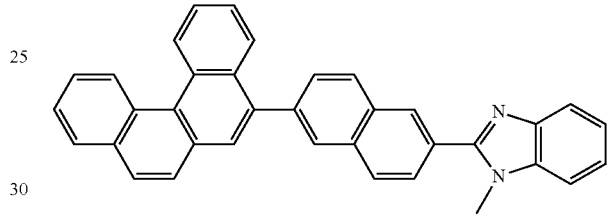
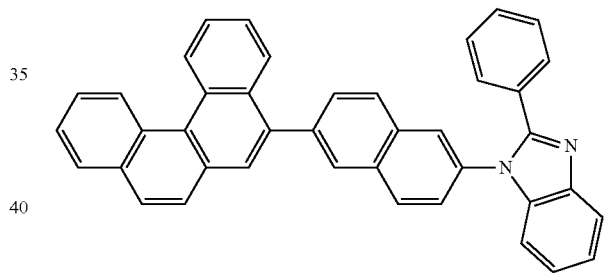
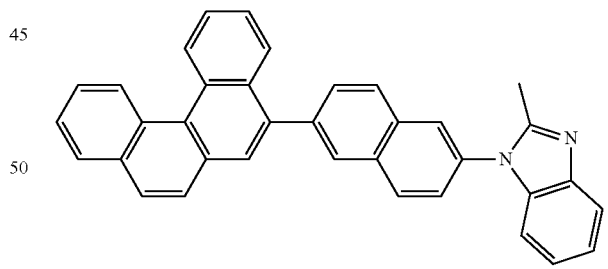
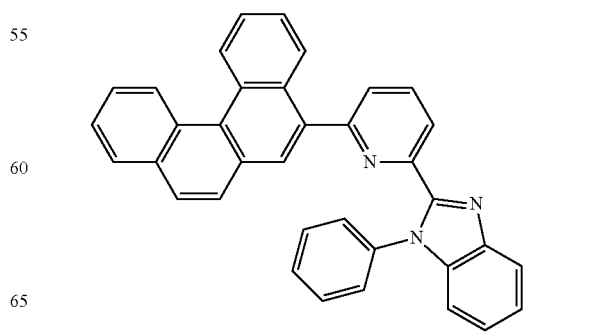

27
-continued
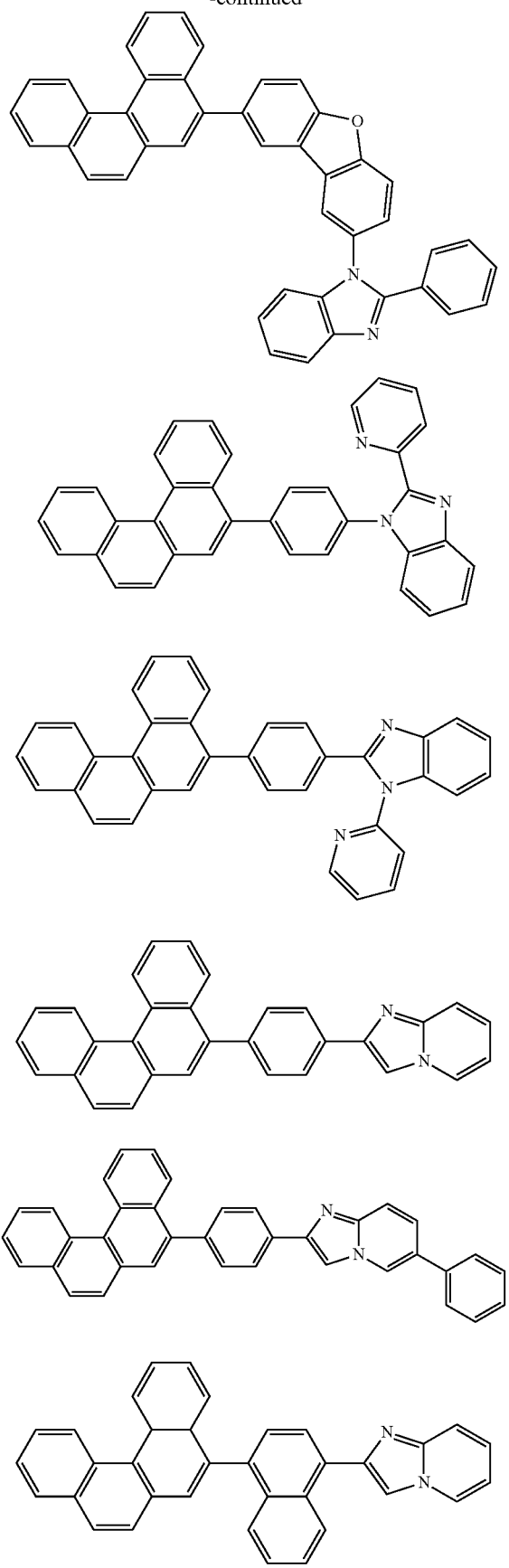
28
-continued
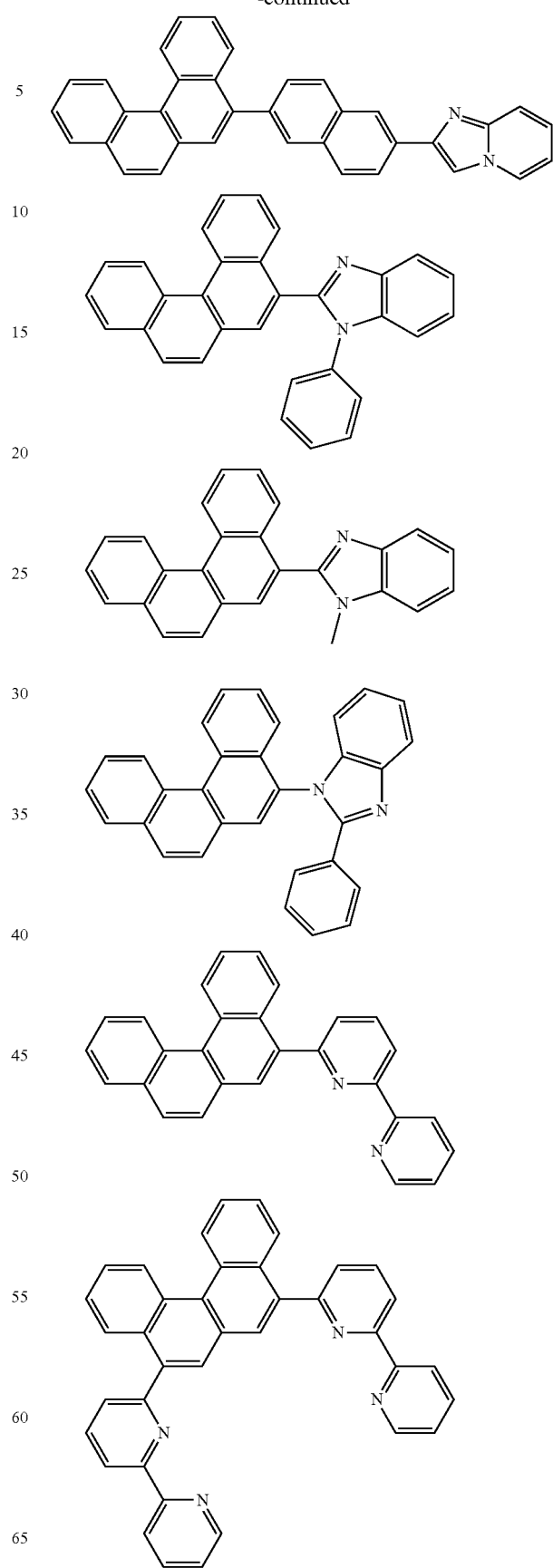

-continued
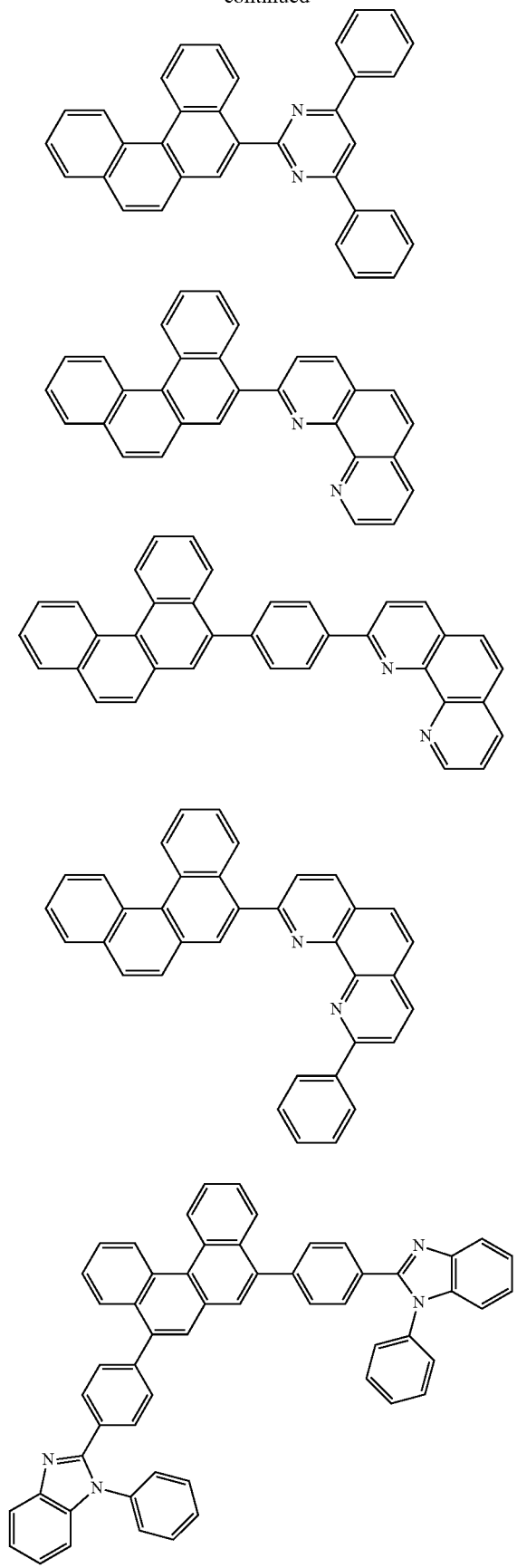
-continued
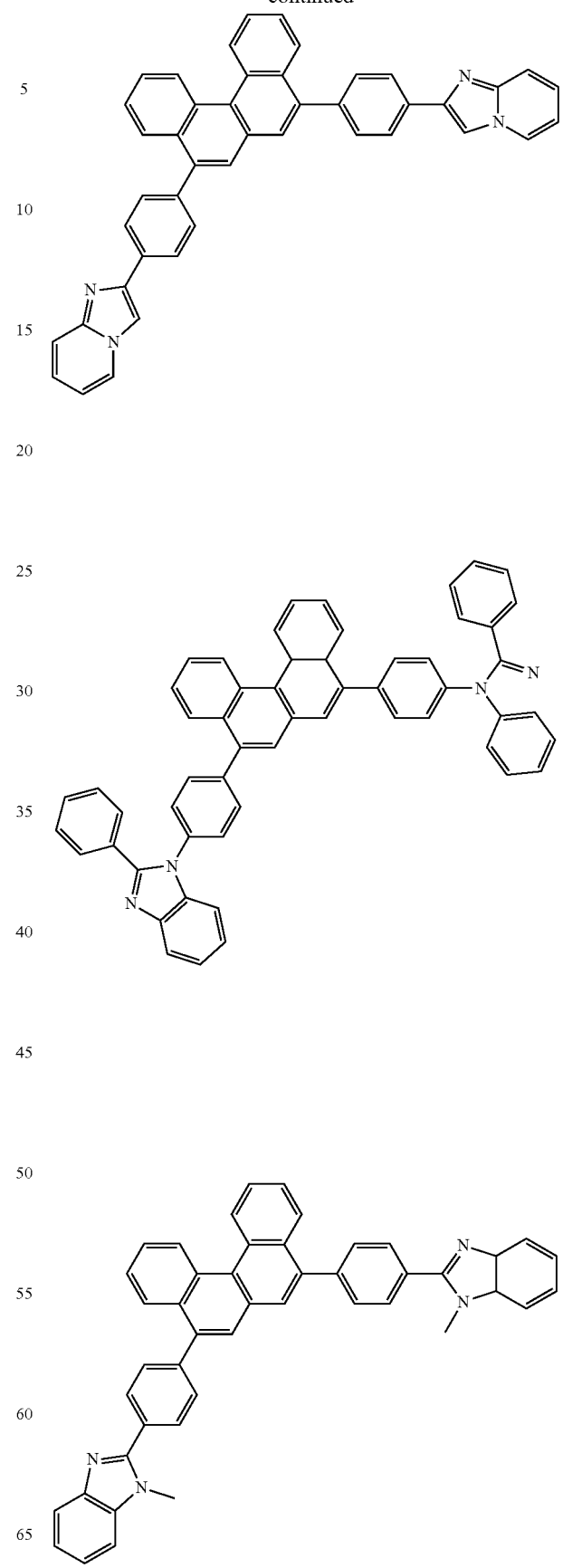

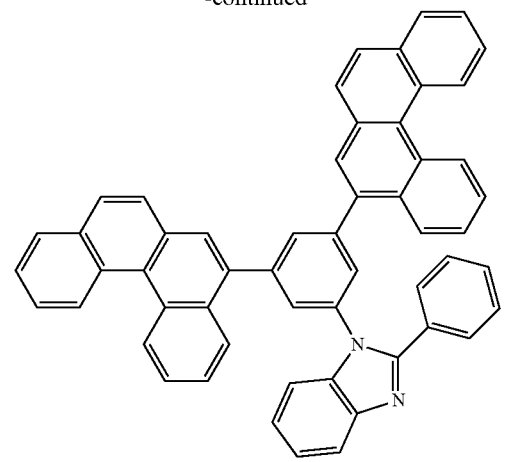
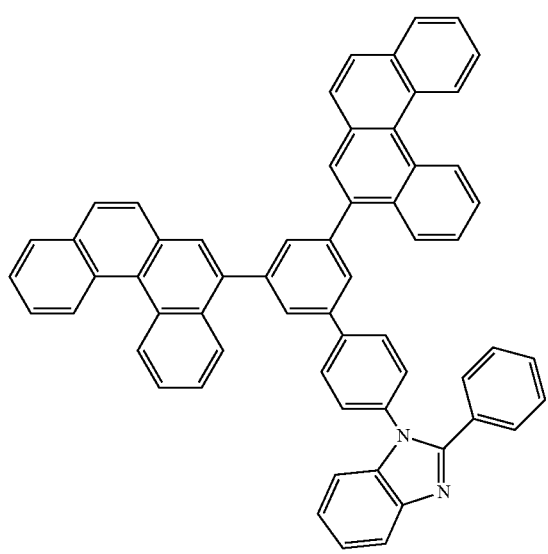
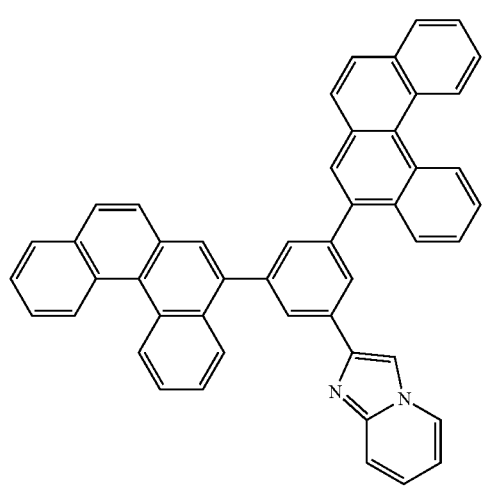
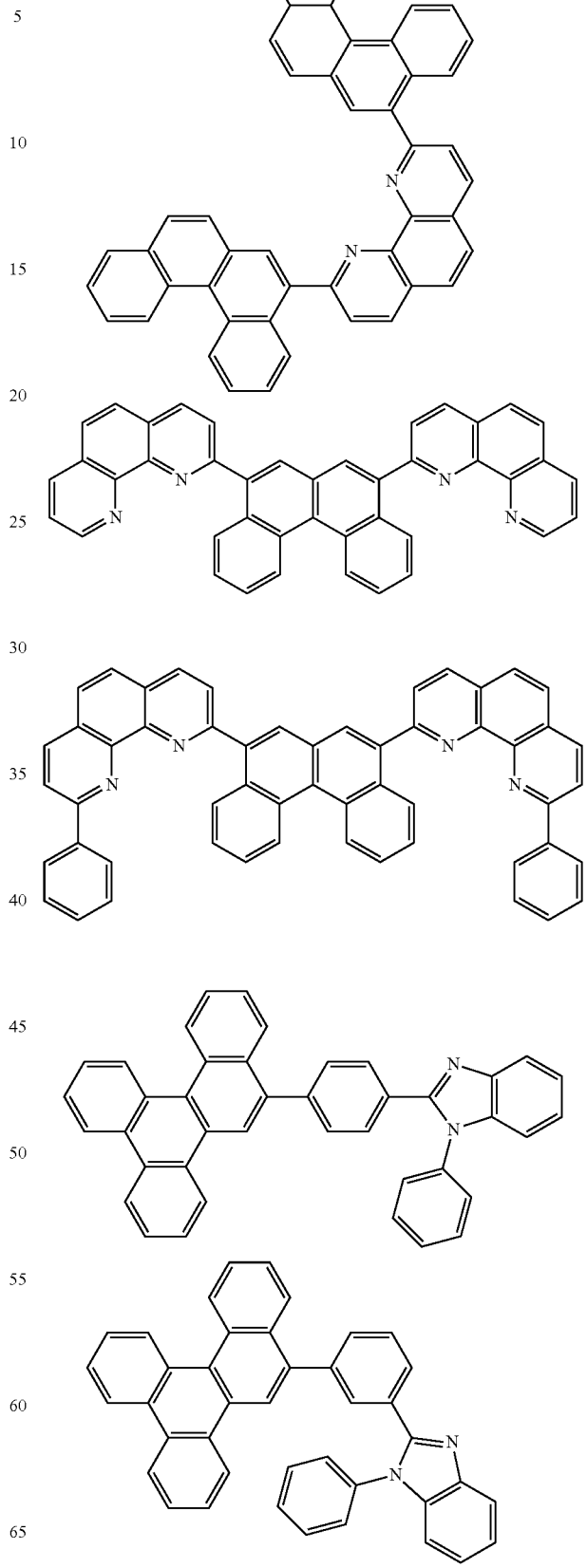

33
-continued
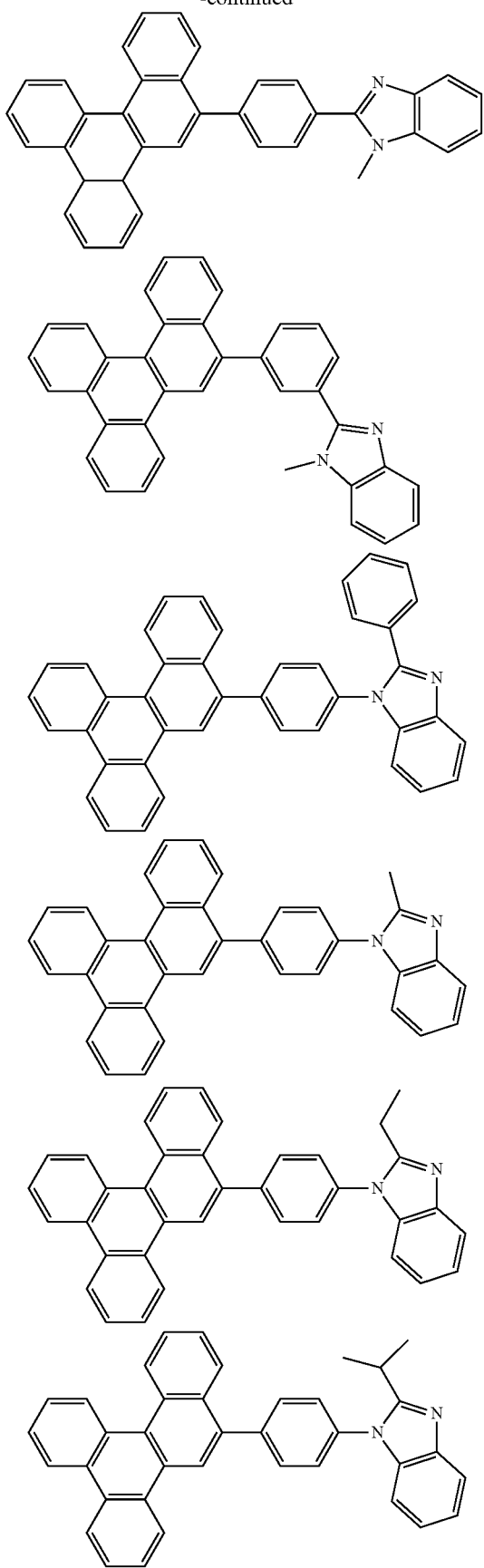
34
-continued
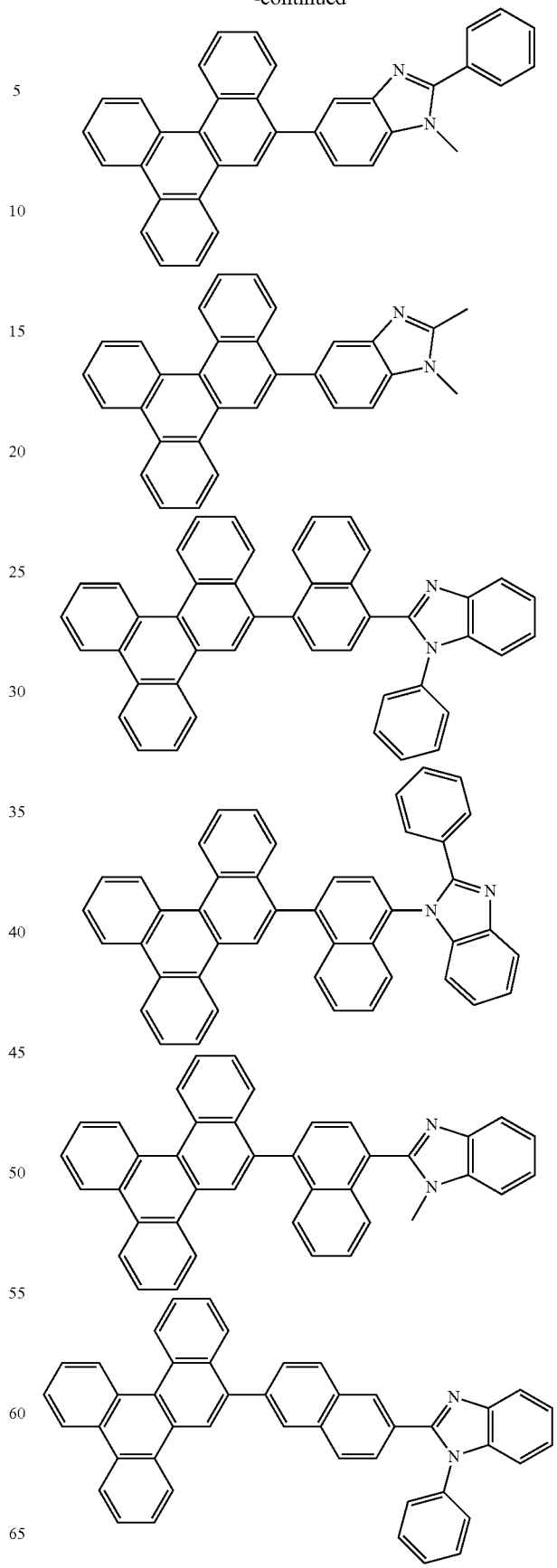

35
-continued
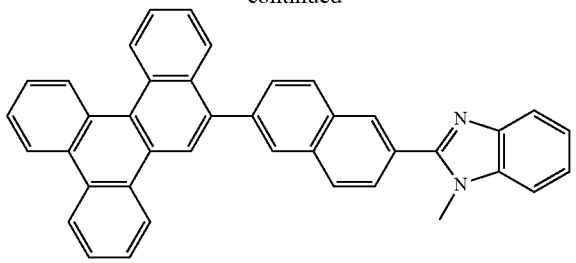
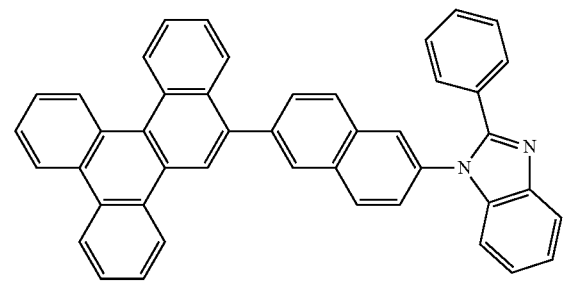
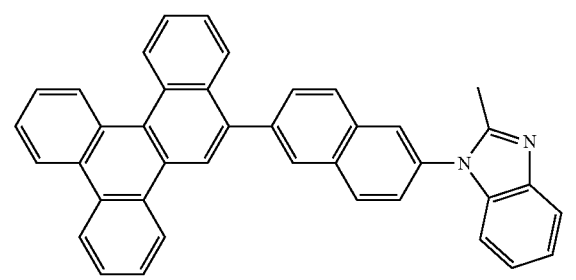
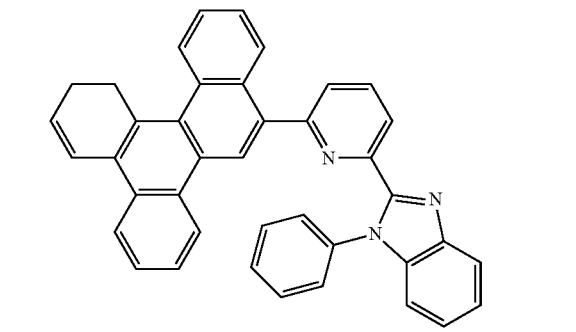
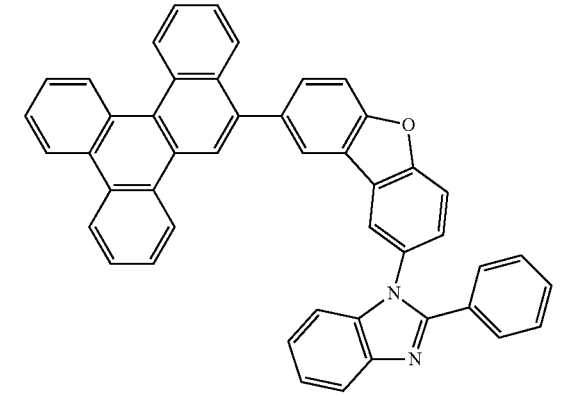
36
-continued
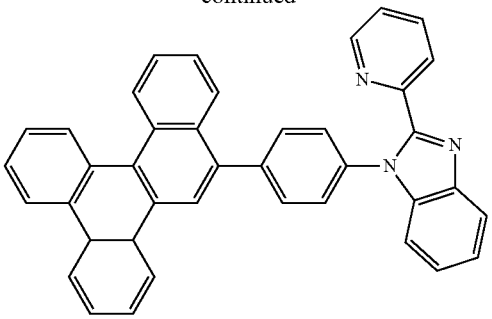
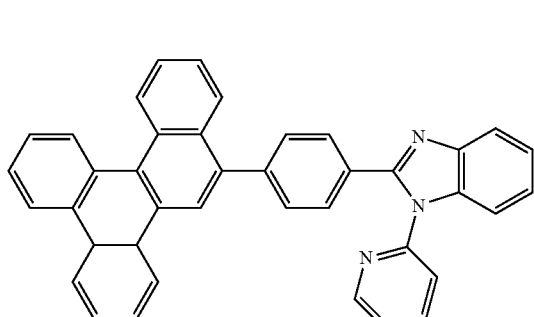
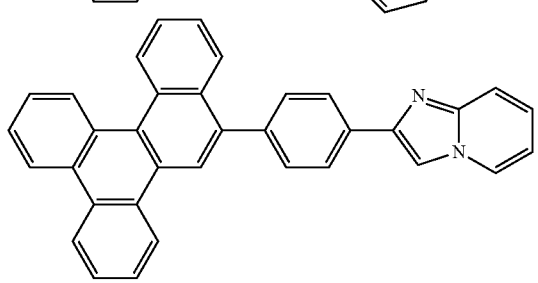
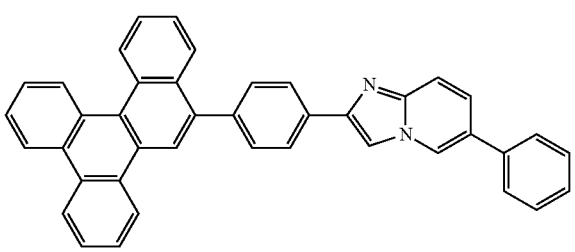
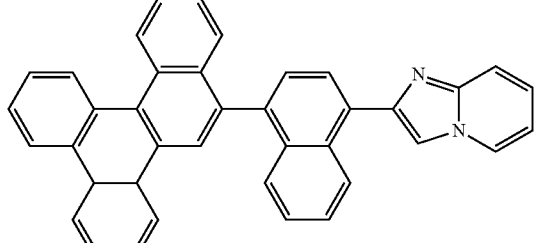
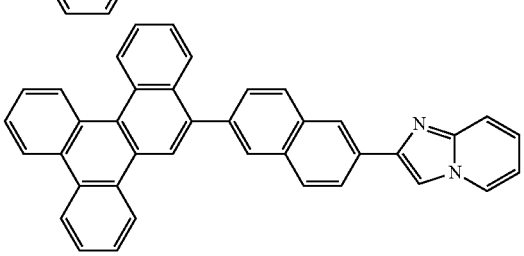

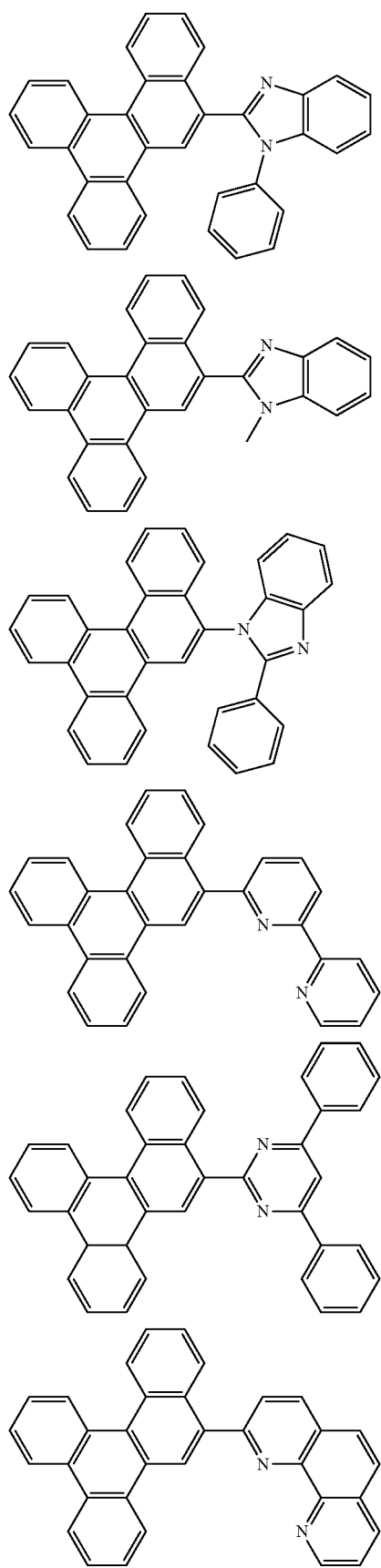
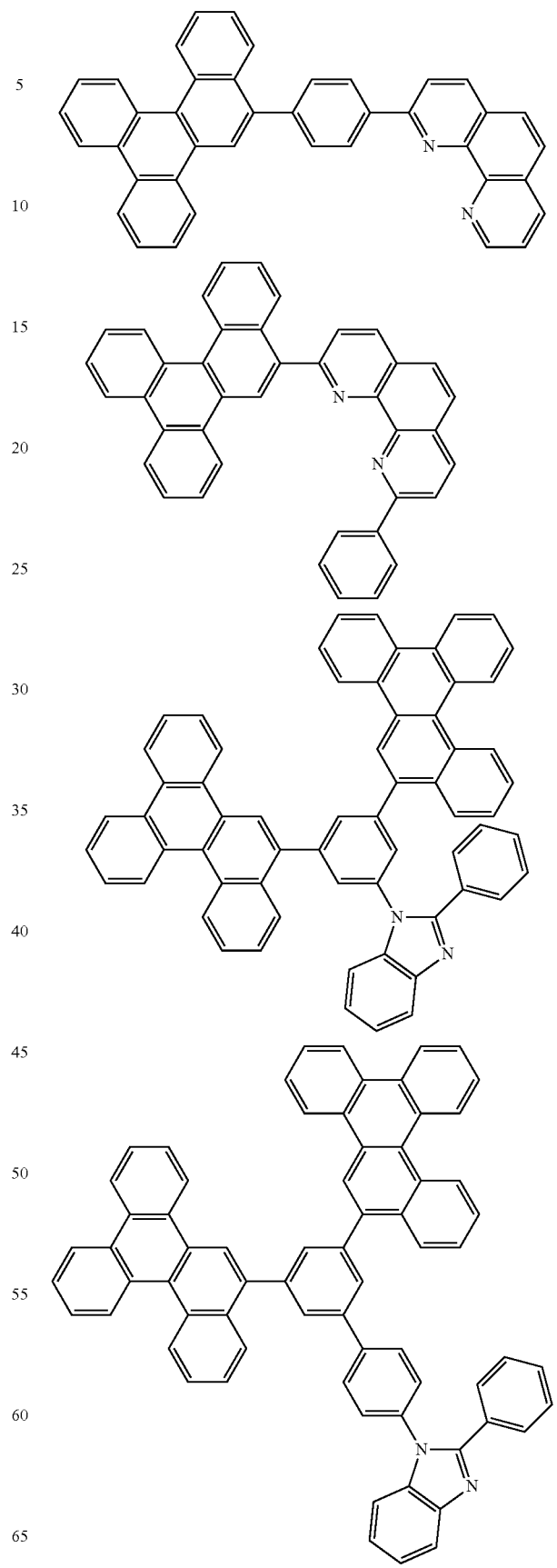

39
-continued
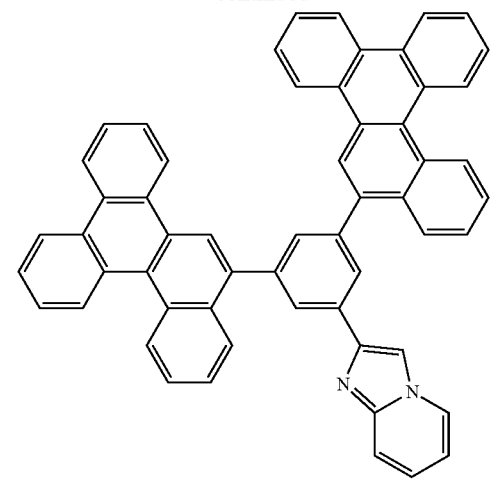
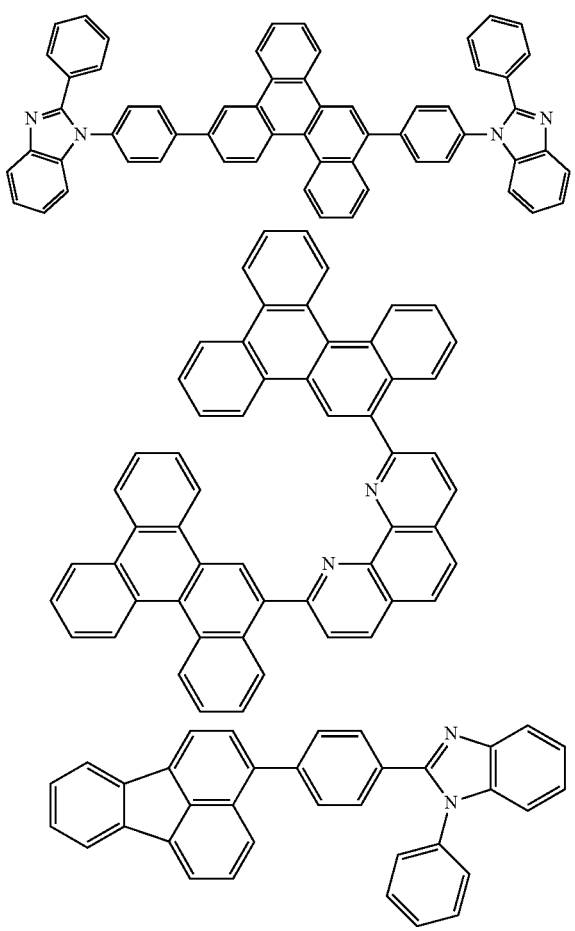
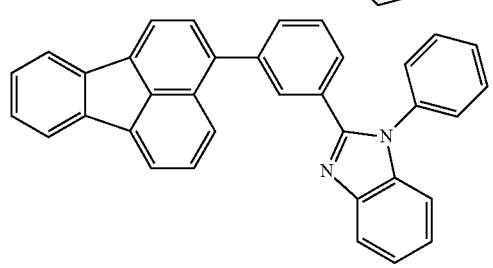
40
-continued
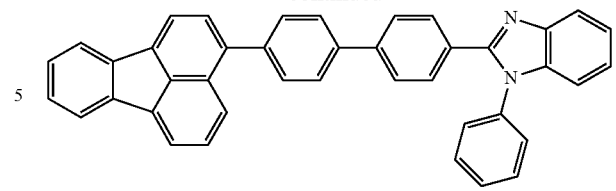
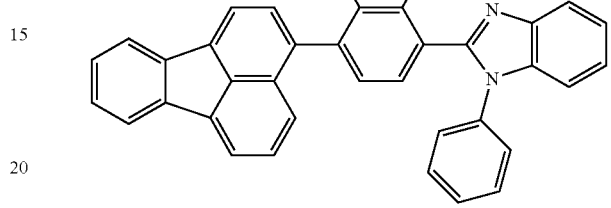
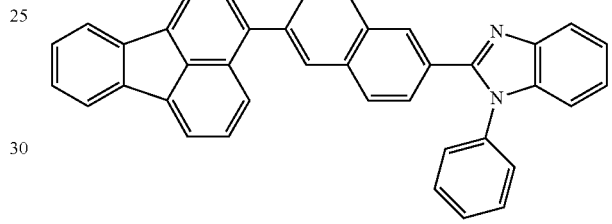
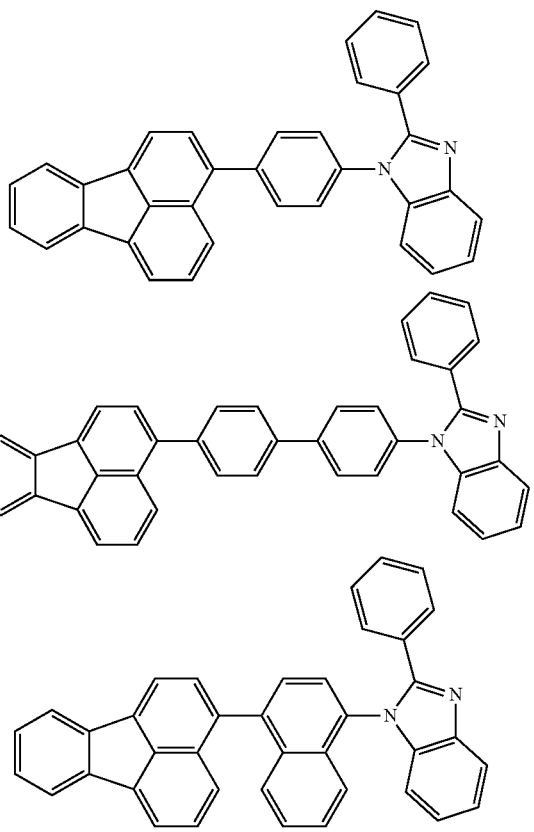

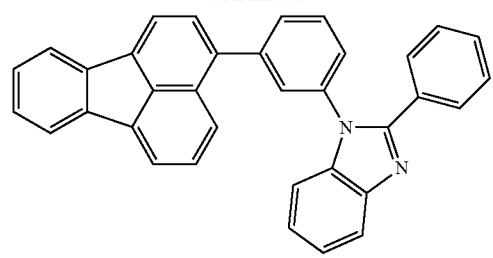
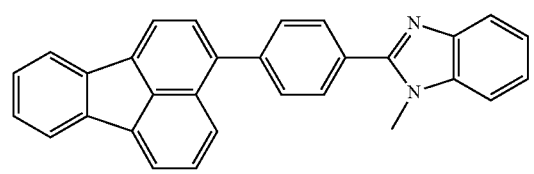
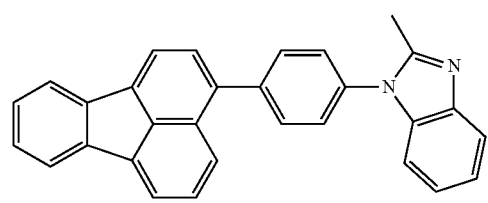
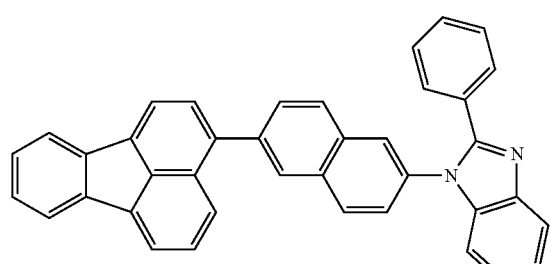
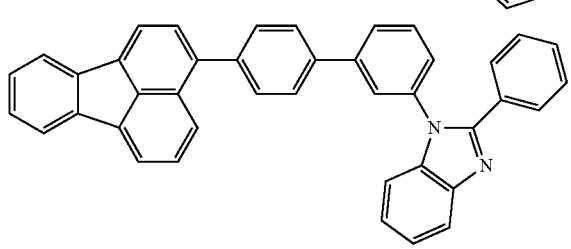
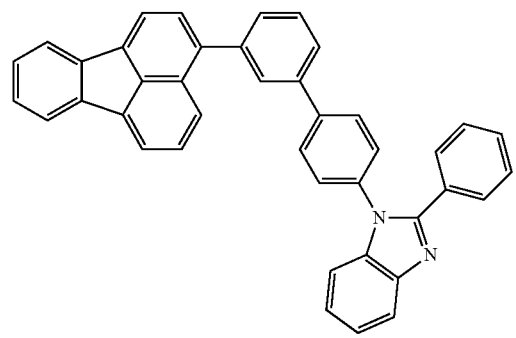
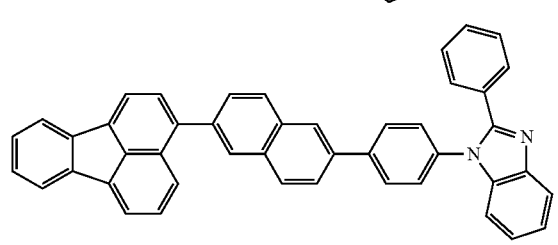
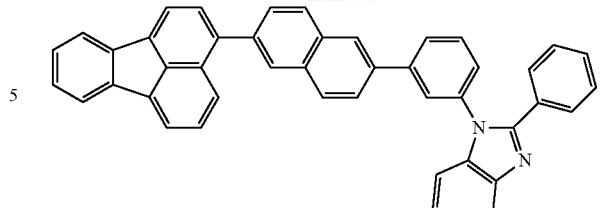
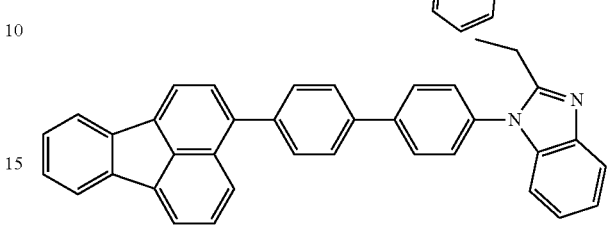
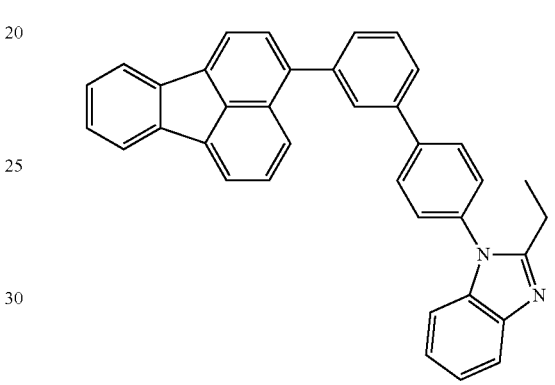
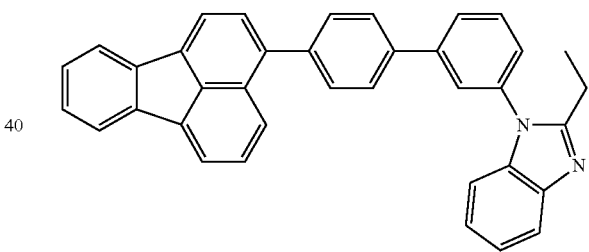
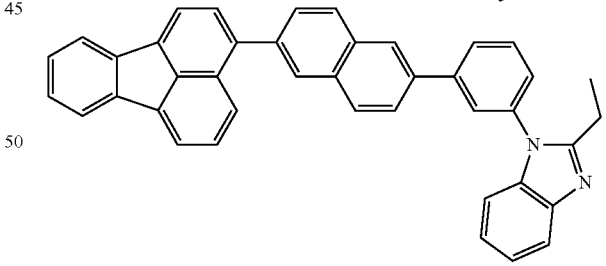
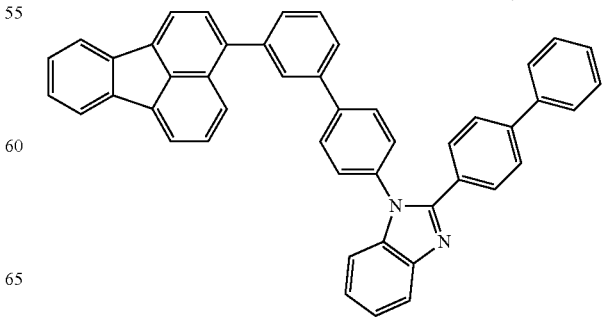

43
-continued
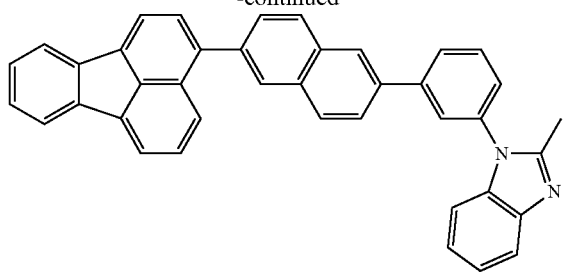
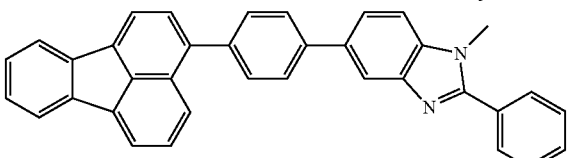
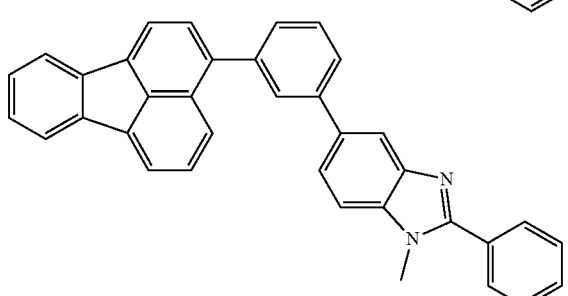
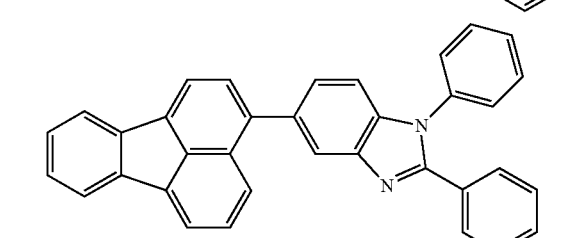
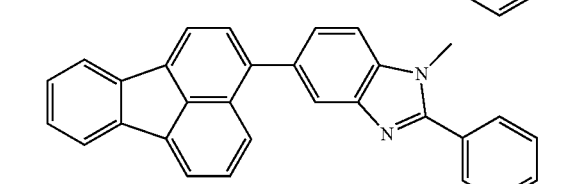
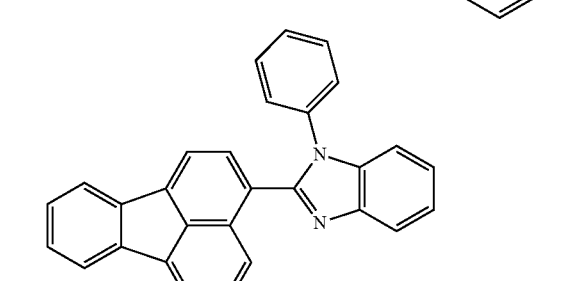
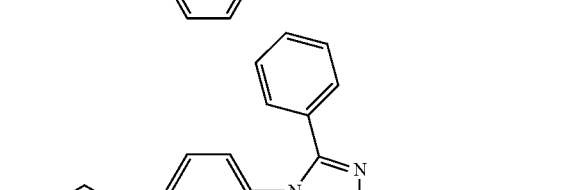
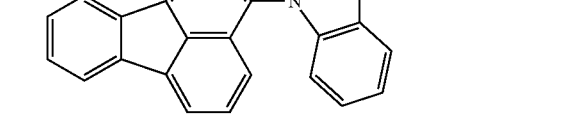
44
-continued
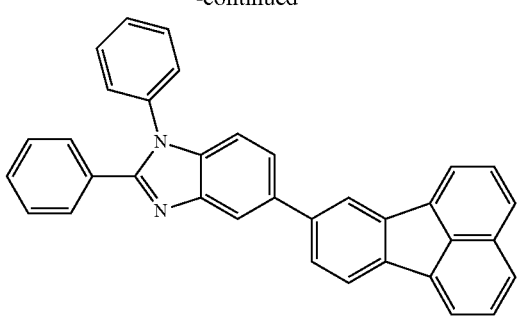
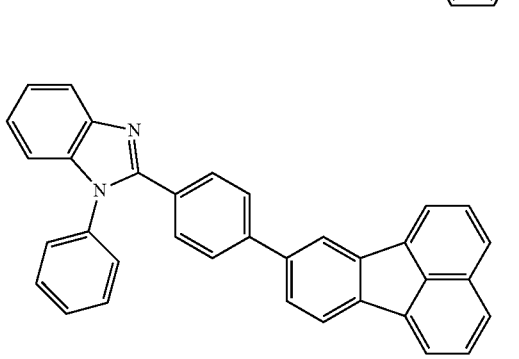
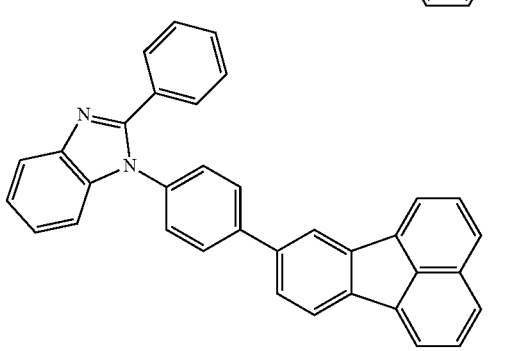
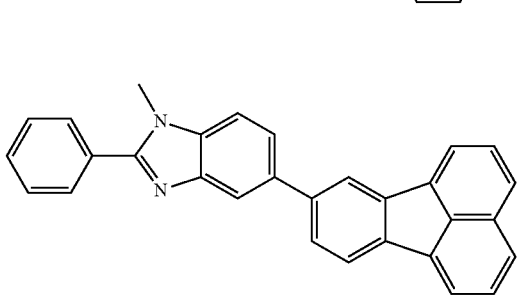
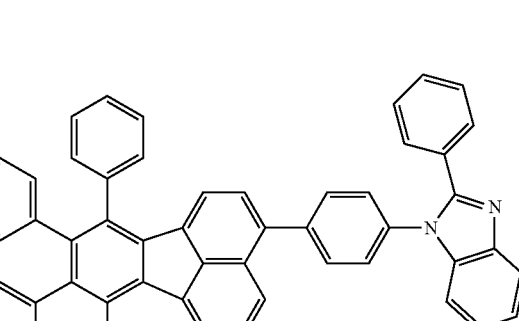
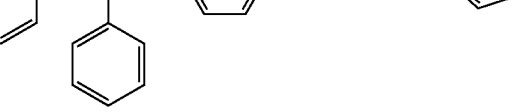

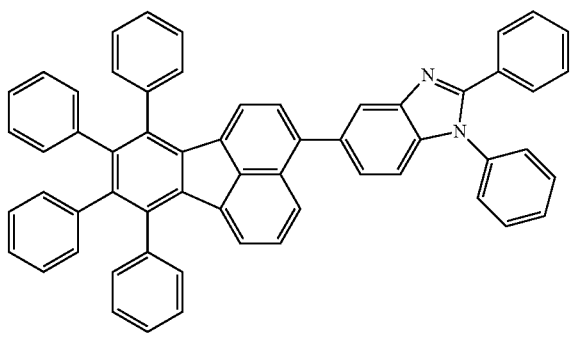

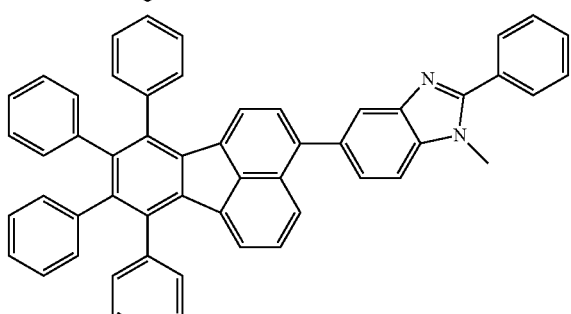

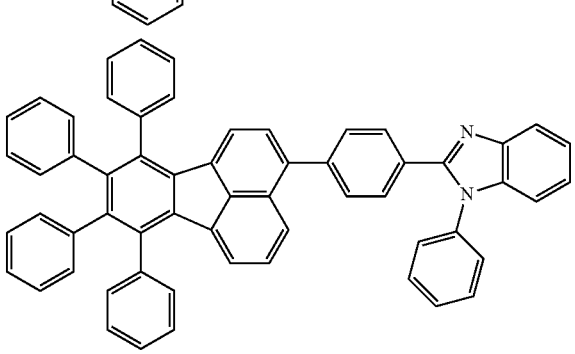

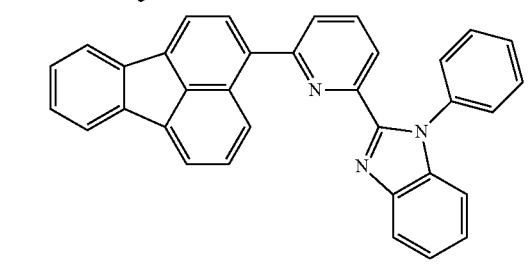

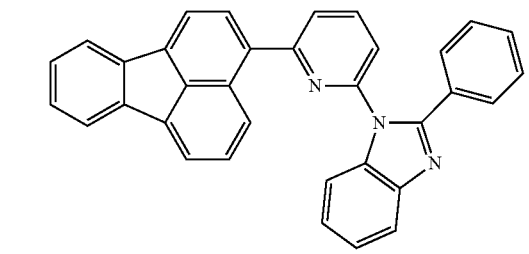

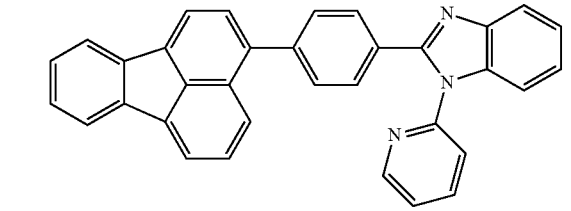

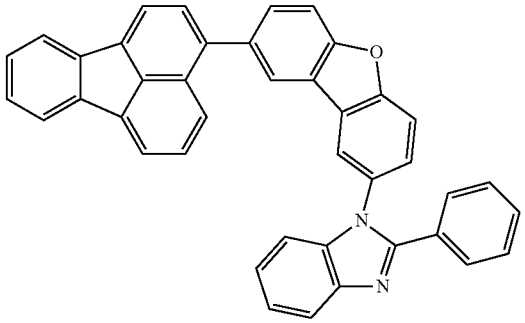

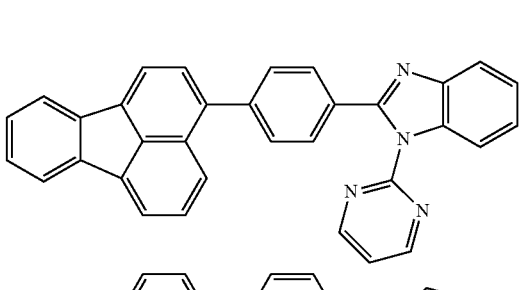

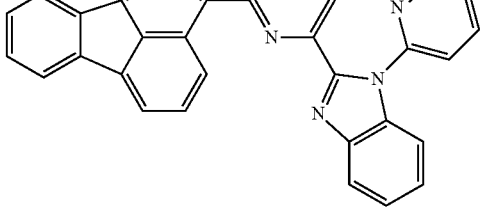

It is preferred that the nitrogen-containing heterocyclic derivative of the invention be used as a material for an organic EL device. It is more preferred that the nitrogen-containing heterocyclic derivative of the invention be used as a blocking material for an organic EL device.

Benzophenanthrene, benzochrysene and fluoranthene, which are the basic skeletons of the nitrogen-containing heterocyclic derivative of the invention, have a high triplet energy, and has improved effects of confining triplet excitons. For example, by using as the material for the blocking layer which is adjacent to the emitting layer of an organic EL device, they can promote occurrence of TTF phenomenon. Further, benzophenanthrene, benzochrysene and fluoranthene, which are the basic skeletons of the nitrogen-containing heterocyclic derivative of the invention, have characteristics that molecular stacking within a thin film is increased due to their high planarity, whereby the electron mobility is increased. As a result, injection of electrons to the emitting layer is promoted and efficiency of electron recombination in the emitting layer is improved, thus enabling a TTF phenomenon to be caused efficiently. In addition, since the nitrogen-containing heterocyclic derivative of the invention comprises a nitrogen-containing heterocyclic ring which has a high electron-injecting property from a metal-containing layer such as an electrode, it is possible to realize a low-voltage driving organic EL device without the need of further stacking an electron-injecting layer.

Meanwhile, the nitrogen-containing heterocyclic derivative of the invention can be preferably used in the electron-injecting layer and/or the electron-transporting layer.

A brief explanation of the TTF phenomenon will be given below.

When a voltage is applied to an organic EL device, electrons and holes are injected from the anode and the cathode, respectively, the electrons and the holes thus injected are recombined in the emitting layer to generate excitons. As for the spin state of the excitons, singlet excitons account for 25% and triplet excitons account for 75%. In a conventionally known fluorescent device, light is emitted when singlet excitons are relaxed to the ground state. However, triplet excitons are returned to the ground state without emitting light after passing the thermal deactivation process. However, according to S. M. Bachilo et al. (J. Phys. Chem. A, 104, 7711 (2000)), of the initially generated 75% triplet excitons, one-fifth thereof is changed to singlet excitons.

TTF is a phenomenon in which singlet excitons are generated by collision and fusion of triplet excitons. By utilizing the TTF phenomenon, not only 25% singlet excitons which are initially generated, but also singlet excitons which are generated by collision and fusion of the triplet excitons can be utilized for emission, whereby luminous efficiency of the device can be enhanced.

In order to allow a TTF phenomenon to occur efficiently, it is necessary to confine triplet excitons which have a significantly long exciton life as compared with that of singlet excitons within the emitting layer.

In the invention, it is preferred that a blocking layer which is normally used in a phosphorescence device be positioned such that it is adjacent to the emitting layer of a fluorescent device so that the blocking layer comprises the nitrogen-containing heterocyclic derivative of the invention. In a fluorescent device which emits light by singlet excitons, which have a shorter exciton life, a blocking layer is not generally used since the provision thereof leads to an increase in process. By using a blocking layer which comprises the nitrogen-containing heterocyclic derivative of the invention in a fluorescent device, a TTF phenomenon is caused to occur, whereby a highly efficient organic EL device can be realized. Further, since the nitrogen-containing derivative of the invention has a high triplet energy, in a conventional phosphorescence device, it can exhibit the function of a blocking layer, and can prevent diffusion of triplet energy.

In the invention, when reference is simply made to the blocking layer, it means a layer which has effects of blocking triplet energy, and it has a function different from that of a hole-blocking layer or a charge-blocking layer.

It is preferred that the blocking layer which comprises the nitrogen-containing heterocyclic derivative of the invention further comprise a reductive dopant.

The above-mentioned reductive dopant is preferably one or two or more selected from the group consisting of an alkali metal, an alkaline earth metal, a rare earth metal, an oxide of an alkali metal, a halide of an alkali metal, an oxide of an alkaline earth metal, a halide of an alkaline earth metal, an oxide of a rare earth metal, a halide of a rare earth metal, an organic complex of an alkali metal, an organic complex of an alkaline earth metal and an organic complex of a rare earth metal.

In the emitting layer of the organic EL device of the invention, rubrene, anthracene, tetracene, pyrene, perylene or the like can be used. An anthracene derivative is preferable, with an anthracene derivative represented by the formula (41) being further preferably included.

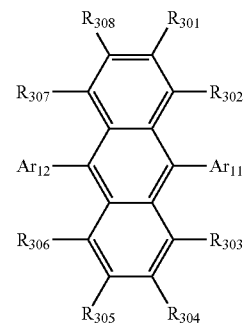

(41)

wherein $Ar_{11}$ and $Ar_{12}$ are independently a substituted or unsubstituted aryl group having 6 to 30 ring carbon atoms or a substituted or unsubstituted heterocyclic group having 5 to 30 ring atoms; and $R_{301}$ to $R_{308}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms. Meanwhile, specific examples of the aryl group, the heterocyclic group, the alkyl group, the cycloalkyl group, the alkylsilyl group, the arylsilyl group, the alkoxy group and aryloxy group mentioned above are the same as those of $R_1$ to $R_{12}$, $R_{201}$ to $R_{214}$, $R_{401}$ to $R_{416}$ and the like in the above-mentioned formulas (1), (21) and (31)

It is preferred that the emitting layer comprising the anthracene derivative represented by the formula (41) be adjacent to the blocking layer comprising the nitrogen-containing heterocyclic derivative of the invention. When the emitting layer is adjacent to the blocking layer which comprises the nitrogen-containing heterocyclic derivative of the invention, it is possible to enhance the luminous efficiency by utilizing a TTF phenomenon.

When a TTF phenomenon is used, the triplet energy of the compound constituting the block layer composed of the nitrogen-containing heterocyclic derivative of the invention is required to be higher than the triplet energy of a host which mainly constitutes the emitting layer. It is preferred that the nitrogen-containing heterocyclic derivative of the invention and a host and a dopant contained in the emitting layer satisfy the following formulas (1) and (2):

$$E^T b > E^T h \quad (1)$$

$$E^T d > E^T h \quad (2)$$

($E^T h$, $E^T b$ and $E^T d$ are independently the triplet energy of the host material, the nitrogen-containing heterocyclic derivative of the blocking layer and the dopant.)

Figure 2A:
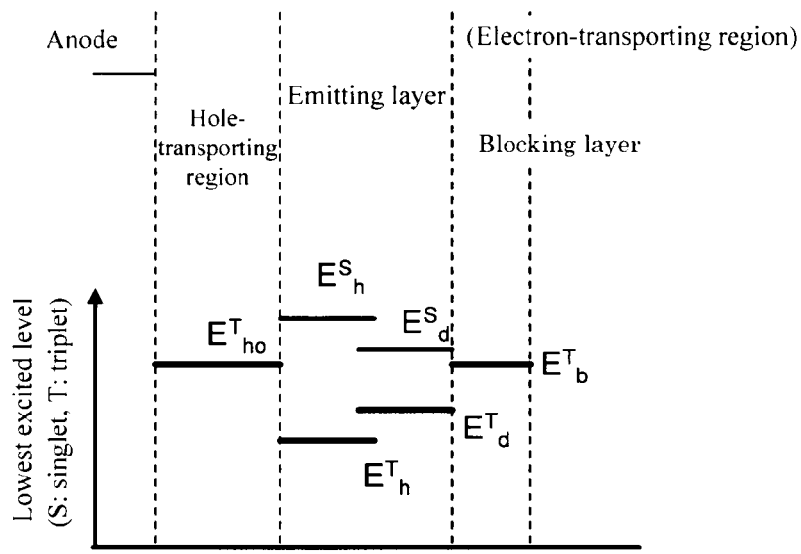
FIG. 2A is a view showing the relationship of energy gap of each layer of the invention.

FIG. 1 is a schematic constitutional view showing one example of the first embodiment of the invention. FIG. 2A diagrammatically shows the lowest singlet excited energy level and the lowest excited triplet energy level of each layer. In the invention, the triplet energy means a difference in energy between the lowest excited triplet energy state and the ground state, and the singlet energy means a difference in energy between the lowest excited singlet energy state and the ground state. The organic EL device shown in FIG. 1 has a configuration in which an anode 10, a hole-transporting region 50, an emitting layer 20, an electron-transporting region 30 and a cathode 40 are sequentially stacked from the anode 10. It is preferred that the hole-transporting region 50 be provided between the anode 10 and the emitting layer 20. FIG. 2A shows an embodiment in which the electron-transporting region is formed only of a blocking layer. It should be noted that an embodiment in which the electron-transporting region which is formed only of a blocking layer does not inhibit insertion of the electron-injecting layer which has higher electron-injecting properties. When forming an electron-injecting layer, known compounds which have conventionally been used as an electron-injecting layer can be used. Of these, a heterocyclic compound is preferable.

In FIG. 2A, holes which have been injected from the anode are injected to the emitting layer through the hole-transporting region, and electrons which have been injected from the cathode are injected to the emitting layer through the electron-transporting region. Then, the holes and the electrons are recombined in the emitting layer, whereby singlet excitons and triplet excitons are generated. There are two cases of occurrence of recombination; i.e. recombination which occurs on the host molecule and recombination which occurs on the dopant molecule. In this embodiment, as shown in FIG. 2A, when the triplet energy of the host and the dopant is taken as $E^T h$ and $E^T d$, respectively, it is preferred that the relationship $E^T h < E^T d$ be satisfied. When this relationship is satisfied, as further shown by FIG. 2B, triplet excitons which are generated by the recombination on the host molecule do not move to a dopant having a higher triplet energy.

Triplet excitons generated by the recombination on the dopant molecule are subjected to energy transfer smoothly to the host molecule. That is, singlet excitons are generated efficiently by a TTF phenomenon due to the collision of triplet excitons on the host molecule without the energy transfer of triplet excitons of the host to the dopant. Further, since the singlet energy $E^s d$ of the dopant is smaller than the singlet energy $E^s h$ of the host, singlet excitons generated by a TTF phenomenon are subjected to energy transfer from the host to the dopant, and contribute to the fluorescence emission of the dopant. Originally, in a dopant used in a fluorescent device, transition from the excited triplet state to the ground state corresponds to a band gap, and in such a band gap, triplet excitons do not undergo optical deactivation, and undergo thermal deactivation. However, by allowing the relationship of the triplet energy of the host and the triplet energy of the dopant to be the above-mentioned range, singlet excitons are efficiently generated by the collision of triplet excitons before triplet excitons undergo thermal deactivation, whereby luminous efficiency is improved.

In the electron-transporting region, the blocking layer is provided at a part which is adjacent to the emitting layer. The blocking layer prevents diffusion of triplet excitons generated in the emitting layer to the electron-transporting region to confine triplet excitons within the emitting layer to increase the density of triplet excitons, whereby a TTF phenomenon is efficiently caused.

Figure 2B:
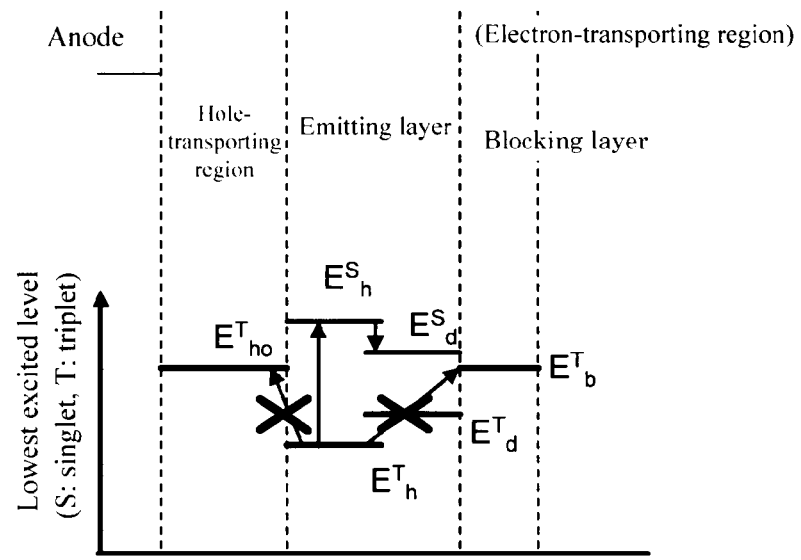
FIG. 2B is a view showing the action based on the relationship of energy gap of each layer of the invention.

In order to prevent diffusion of triplet excitons, as shown in FIGS. 2A and 2B, it is preferred that the triplet energy $E^T b$ of a compound forming the blocking layer be larger than $E^T h$. It is further preferred that the triplet energy $E^T b$ be further larger than $E^T d$. Since the blocking layer prevents triplet excitons generated in the emitting layer from being diffused to the electron-transporting zone, within the emitting layer, triplet excitons of the host become singlet excitons efficiently. These singlet excitons transfer to the dopant and undergo optical deactivation. The material forming the blocking layer is the nitrogen-containing heterocyclic derivative of the invention.

The blocking layer containing the nitrogen-containing heterocyclic derivative of the invention can also have the function of electron injection and transportation. The reason therefor is that a lone pair of electrons mediates transfer of electrons from the adjacent layers. Next, electrons which have been injected to the blocking layer easily donate electrons through the electron-transporting structure part. That is, by moving to a structure part having a lower LUMO level, they contribute electron injection to the emitting layer.

A low-work function metal containing layer may be provided between the electron-transporting region and the cathode. The low-work function metal containing layer means a layer containing a low-work function metal or a low-work function metal compound. It may be formed only of a low-work function metal or a low-work function metal compound, or may be formed by adding as a donor a low-work function metal, a low-work function metal compound or a low work function metal complex to a material used as an electron-transporting layer. A low-work function metal means a metal having a work function of 3.8 eV or less. As the metal having a work function of 3.8 eV or less, an alkali metal, an alkaline earth metal or the like can be mentioned. As the alkali metal, Li, Na, K, Cs or the like can be given. As the alkaline earth metal, Mg, Ca, Sr, Ba or the like can be given. As other metals, Yb, Eu, Ce or the like can be given. As the low-work function metal compound, oxides, halides, carbonates and borates of a low-work function metal are preferable. As the halides, fluorides, chlorides and bromides can be given, with fluorides being preferable. LiF can be given as a preferable halide, for example. As the low-work function metal complex, a complex of a low-work function metal can be given, with an organic metal complex of an alkaline metal, an alkaline earth metal or a rare earth metal being preferable.

Efficiency can be improved significantly in a blue fluorescence layer by utilizing a TTF phenomenon. However, also in a green fluorescence layer and a red fluorescence layer, luminous efficiency can be improved by confining triplet energy within the emitting layer.

In the phosphorescence layer, it is possible to obtain effects of confining triplet energy in the emitting layer, to prevent diffusion of triplet energy, whereby improvement in luminous efficiency of a phosphorescence dopant can be attained.

Other elements such as the substrate, the anode, the cathode, the hole-injecting layer, the hole-transporting layer or the like of the organic EL device of the invention can be used by appropriately selecting those stated in PCT/JP2009/053247, PCT/JP2008/073180, U.S. patent application Ser. No. 12/376,236, U.S. patent application Ser. No. 11/766,281, U.S. patent application Ser. No. 12/280,364 or the like.

EXAMPLES

Synthesis Example 1

(A) Synthesis of benzo[c]phenanthrene-5-boronic acid

Benzo[c]phenanthrene-5-boronic acid was synthesized according to the following scheme:

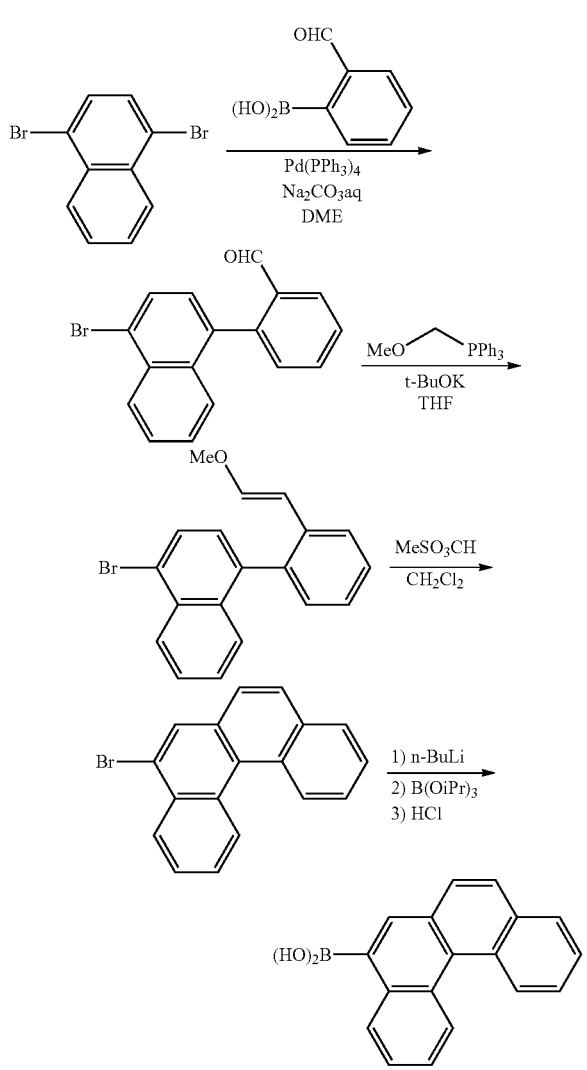

(A-1) Synthesis of
1-bromo-4-(2-formylphenyl)naphthalene

Under the atmosphere of argon, 230 g of 1,4-dibromonaphthalene, 121 g of 2-formylphenylboronic acid and 18.5 g of tetrakis(triphenylphosphine)palladium(0) were placed in a flask. To the resulting mixture, 2.4 L of dimethoxyethane (DME) and 1.2 L of an aqueous 2M sodium carbonate solution were added, followed by stirring under reflux for 8 hours. After cooling to the room temperature, an aqueous phase was removed, and an organic phase was washed with water and saturated saline, and dried with magnesium sulfate. After filtering off magnesium sulfate, the organic phase was concentrated. The residues were purified by silica gel column chromatography, whereby 170 g (yield 67%) of 1-bromo-4-(2-formylphenyl)naphthalene as an intended product was obtained.

(A-2) Synthesis of
1-bromo-4-[2-(2-methoxyvinyl)phenyl]naphthalene

Under the atmosphere of argon, 170 g of 1-bromo-4-(2-formylphenyl)naphthalene, 207 g of methoxymethyltriphenylphosphonium chloride and 2.0 L of tetrahydrofuran (THF) were placed, and 73.6 g of potassium t-butoxide was added at room temperature during stirring. After stirring at room temperature for 2 hours, 1.5 L of water was added. The reaction solution was extracted with diethyl ether, and an aqueous phase was removed. An organic phase was washed with water and saturated saline, and dried with magnesium sulfate. After filtering off magnesium sulfate, the organic phase was concentrated. The residues were purified by silica gel column chromatography, whereby 180 g (yield 99%) of 1-bromo-4-[2-(2-methoxyvinyl)phenyl]naphthalene as an intended product was obtained.

(A-3) Synthesis of 5-bromobenzo[c]phenanthrene 180 g of 1-bromo-4-[2-(2-methoxyvinyl)phenyl]naphthalene and 1.0 L of dichloromethane were placed. 25 mL of methanesulfonic acid was added at room temperature while stirring. The stirring was conducted for 8 hours at room temperature. After the completion of the reaction, 1 L of an aqueous solution of 10% potassium carbonate was added. After removing an aqueous phase, an organic phase was washed with water and saturated saline, and dried with magnesium sulfate. After filtering off magnesium sulfate, the organic phase was concentrated. The residues were purified by silica gel column chromatography, whereby 24.4 g (yield 15%) of 5-bromobenzo[c]phenanthrene as an intended product was obtained.

(A-4) Synthesis of benzo[c]phenanthrene-5-boronic acid

Under the atmosphere of argon, 10.1 g of 5-bromobenzo[c]phenanthrene was placed in a flask, and 400 mL of dehydrated ether was added. The reaction solution was cooled to –40° C., and 22 mL of a hexane solution of 1.6 M n-butyl lithium was added. The resultant was heated to 0° C., and stirred for 1 hour. The reaction solution was cooled to –60° C., and 10 mL of a dehydrated ether solution of 14.4 g of triisopropyl borate was added dropwise. While heating the reaction solution to room temperature, stirring was continued for 5 hours. 10 mL of a 10% aqueous hydrochloric acid solution was added, followed by stirring for 1 hour. An aqueous phase was removed, and an organic phase was washed with water and saturated saline, and dried with magnesium sulfate. After filtering off magnesium sulfate, the organic phase was concentrated. The resulting solids were washed with hexane, whereby 5.37 g (yield 60%) of benzo[c]phenanthrene-5-boronic acid as an intended product was obtained.

Synthesis Example 2

(B) Synthesis of benzo[g]chrysene-10-boronic acid

Benzo[g]chrysene-10-boronic acid was synthesized according to the following scheme:

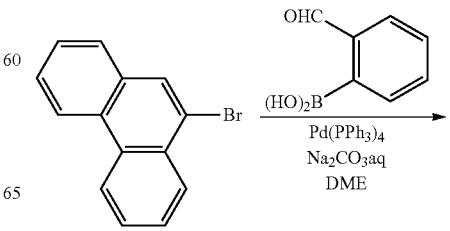

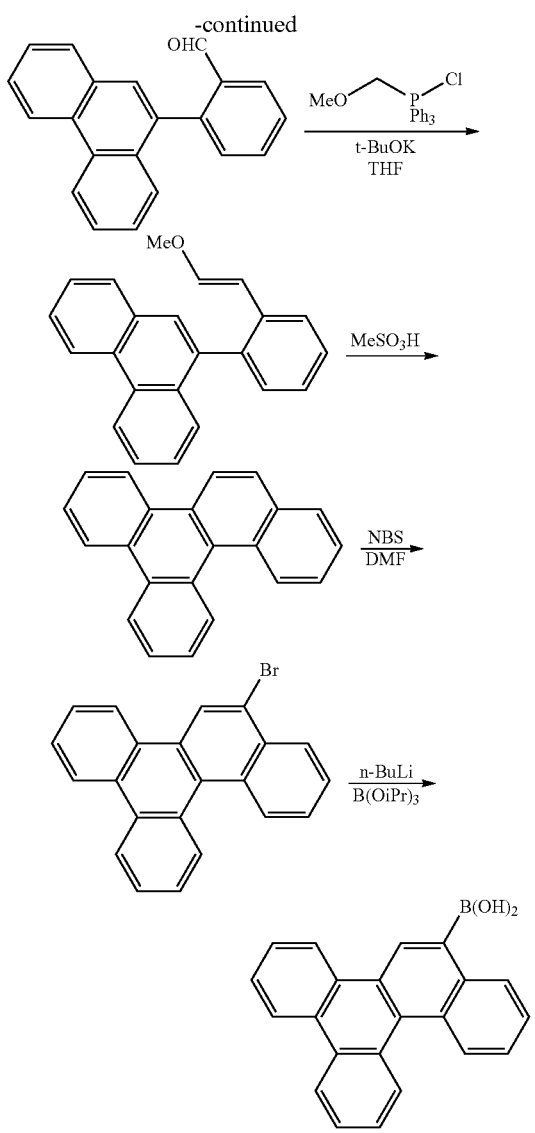

(B-1) Synthesis of 9-(2-formylphenyl)phenanthrene

Under the atmosphere of argon, 25.7 g of 9-bromophenathrene, 16.5 g of 2-formylphenylboronic acid and 2.31 g of tetrakis(triphenylphosphine)palladium (0) were placed in a flask. To the resulting mixture, 340 mL of DME and 170 mL of an aqueous 2M sodium carbonate solution were added, followed by stirring under reflux while heating for 8 hours. After cooling to room temperature, an aqueous phase was removed. An organic phase was washed with water and saturated saline, and dried with magnesium sulfate. After filtering off magnesium sulfate, the organic phase was concentrated. The residues were purified by silica gel column chromatography, whereby 25.0 g (yield 89%) of 9-(2-formylphenyl) phenanthrene as an intended product was obtained.

(B-2) Synthesis of 9-[2-(2-methoxyvinyl)phenyl]phenanthrene

Under the atmosphere of argon, 25.0 g of 9-(2-formylphenyl)phenanthrene, 33.4 g of methoxymethyltriphenylphosphonium chloride and 300 mL of THF were placed, and 11.9 g of potassium t-buthoxide was added at room temperature during stirring. After stirring at room temperature for 2 hours, 200 mL of water was added. The reaction solution was extracted with diethyl ether, and an aqueous phase was removed. An organic phase was washed with water and saturated saline, and dried with magnesium sulfate. After filtering off magnesium sulfate, the organic phase was concentrated. The residues were purified by silica gel column chromatography, whereby 24.0 g (yield 87%) of 9-[2-(2-methoxyvinyl) phenyl]phenanthrene as an intended product was obtained.

(B-3) Synthesis of benzo[g]chrysene 24.0 g of 9-[2-(2-methoxyvinyl)phenyl]phenanthrene and 100 mL of dichloromethane were placed. 6 drops of methanesulfonic acid was added by means of a Pasteur pipette while stirring at room temperature. The stirring was conducted at room temperature for 8 hours. After completion of the reaction, 100 mL of an aqueous 10% potassium carbonate solution was added. An aqueous phase was removed, and an organic phase was washed with saturated saline and dried with magnesium sulfate. After filtering off magnesium sulfate, the organic phase was concentrated. The residues were purified by silica gel column chromatography, whereby 5.21 g (yield 25%) of benzo[g]chrysene as an intended product was obtained.

(B-4) Synthesis of 10-bromobenzo[g]chrysene 5.21 g of benzo[g]chrysene and 50 mL of N,N-dimethylformamide were placed in a flask. 10 mL of N,N-dimethylformamide solution of 4.00 g of N-bromosuccinimide were added. The resulting solution was heated with stirring at 80° C. for 8 hours. After cooling to room temperature, the reaction solution was poured to 200 mL of water. Deposited solids were filtered off, and washed with water and methanol. The resulting solids were purified by silica gel column chromatography, whereby 5.87 g (yield 88%) of 10-bromobenzo[g] chrysene was obtained.

(B-5) Synthesis of benzo[g]chrysene-10-boronic acid

Under the atmosphere of argon, 5.87 g of 10-bromobenzo [g]chrysene was placed in a flask, and 100 mL of dehydrated ether was added. After cooling the reaction solution to −40° C., 11 mL of a 1.6M hexane solution of n-butyllithium was added. The resulting solution was heated to 0° C., followed by stirring for 1 hour. The reaction solution was cooled to −60° C., and 10 mL of a dehydrated ether solution of 7.72 g of triisopropyl borate was added dropwise. The reaction solution was stirred for 5 hours while heating to room temperature. 50 mL of a 10% aqueous hydrochloric acid solution was added, followed by stirring for 1 hour. After removing an aqueous phase, and an organic phase was washed with water and saturated saline, and dried with magnesium sulfate. After filtering off magnesium sulfate, the organic phase was concentrated. The resulting solids were washed with hexane, whereby 3.18 g (yield 60%) of benzo[g]chrysene-10-boronic acid as an intended product was obtained.

Synthesis Example 3

(C) Synthesis of 1-(4-bromophenyl)-2-phenyl-1H-benzimidazole 1-(4-bromophenyl)-2-phenyl-1H-benzimidazole was synthesized according to the following scheme.

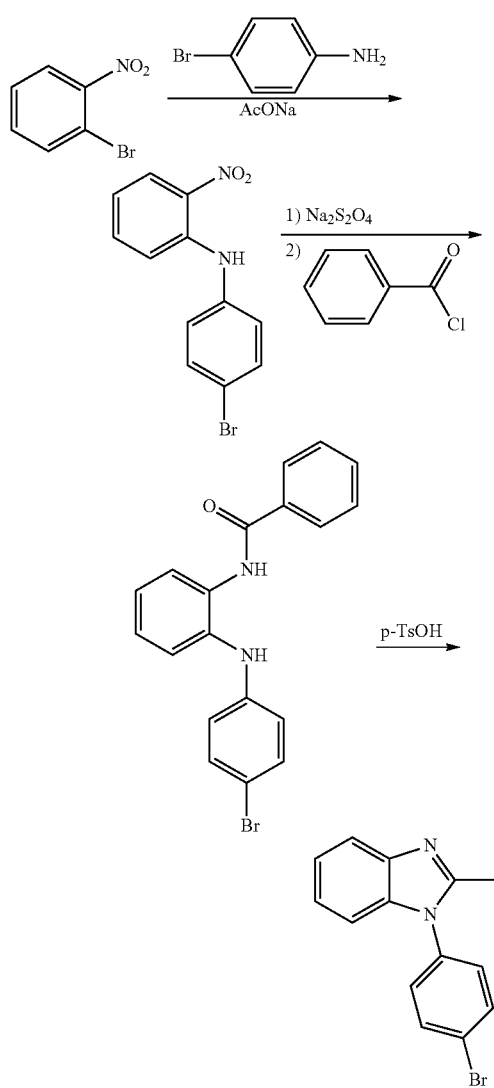

(C-1) Synthesis of (4-bromophenyl)-(2-nitrophenyl)amine 10 g (49.5 mmol) of 2-bromonitrobenzene, 13 g (163 mmol) of sodium acetate and 10 g (59 mmol) of 4-bromoaniline was stirred with heating at 180° C. for 8 hours in the argon atmosphere. The reaction solution was cooled to room temperature, diluted with ethyl acetate, and filtrated. After concentrating the filtrate, residues were washed with methanol, whereby 3.8 g (yield 22%) of orange crystals of (4-bromophenyl)-(2-nitrophenyl)amine were obtained.

(C-2) Synthesis of N-[2-(4-bromophenylamino)phenyl]benzamide 3.8 g (13 mmol) of (4-bromophenyl)-(2-nitrophenyl) amine was dissolved in 30 mL of tetrahydrofuran. The resulting solution was stirred at room temperature in the argon atmosphere. During the stirring, a solution of 11 g (64 mmol) of sodium hydrosulfite/30 mL of water was added dropwise. After stirring for 5 hours, 20 mL of ethyl acetate was added, and then a solution of 2.2 g (26 mmol) of sodium hydrogen carbonate/20 mL of water was added. Further, a solution of 2.5 g (18 mmol) of benzoyl chloride/10 mL of ethyl acetate was added dropwise, and the resultant was stirred at room temperature for 1 hour. The resultant was extracted with ethyl acetate, and sequentially washed with an aqueous 10% potassium carbonate solution, water and saturated saline. Thereafter, the solution was dried with anhydrous sodium sulfate, and the solvent was distilled off under reduced pressure, whereby 2.1 g (yield 45%) of N-[2-(4-bromophenylamino)phenyl] benzamide was obtained.

(C-3) Synthesis of 1-(4-bromophenyl)-2-phenyl-1H-benzimidazole 2.1 g (5.7 mmol) of N-[2-(4-bromophenylamino)phenyl] benzamide was suspended in 30 mL of xylene. To the resulting suspension, 0.6 g (2.9 mmol) of p-toluenesulfonic acid monohydrate was added, and the resultant was subjected to azeotropic dehydration while heating under reflux for 3 hours. After allowing it to be cool, ethyl acetate, methylene chloride and water were added to the reaction solution, and unsoluble matters were filtered off. An organic phase was extracted from a mother solution, washed with water and saturated saline, and dried with anhydrous sodium sulfate. The solvent was distilled off under a reduced pressure. Residues were purified by silica gel column chromatography, whereby 1.0 g of slightly pinky white crystals of 1-(4-bromophenyl)-2-phenyl-1H-benzimidazole were obtained (yield 52%).

Synthesis Example 4

(D) Synthesis of 1-(3-bromophenyl)-2-phenyl-1H-benzimidazole

As shown by the following synthesis scheme, a reaction was conducted in the same manner as in Synthesis Example 3, except that 3-bromoaniline was used instead of 4-bromoaniline, whereby 1-(3-bromophenyl)-2-phenyl-1H-benzimidazole was synthesized.

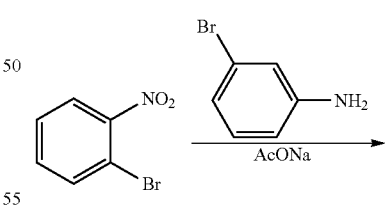

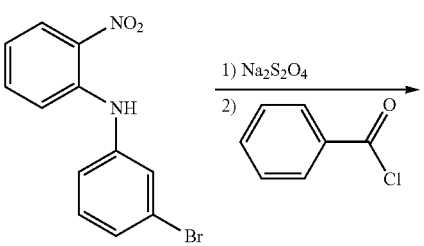

-continued

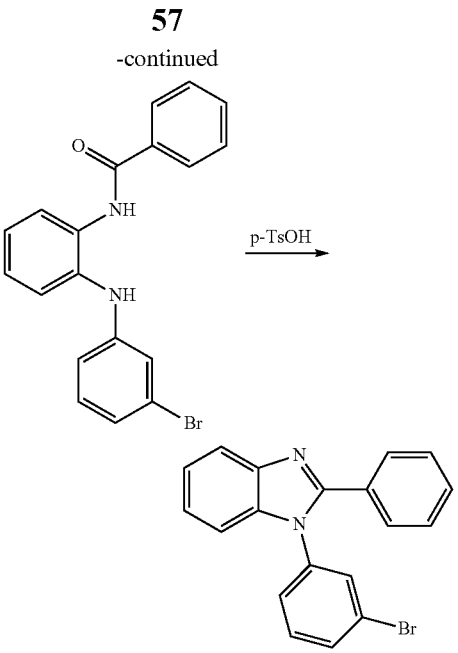

Synthesis Example 5

(E) Synthesis of 5-bromo-1-methyl-2-phenyl-1H-benzimidazole

According to the following synthesis scheme, 5-bromo-1-methyl-2-phenyl-1H-benzimidazole was synthesized.

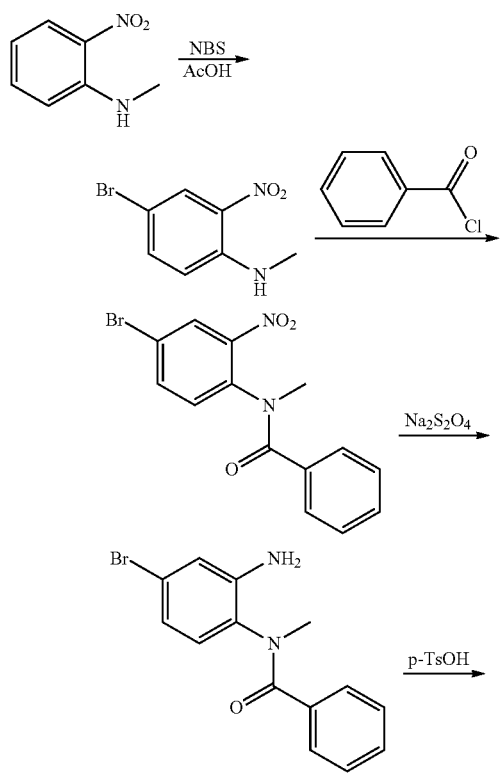

-continued (E-1) Synthesis of 4-bromo-N-methyl-2-nitroanilline 60 mL of acetic acid was added to 5.0 g (33 mmol) of N-methyl-2-nitroaniline and 5.9 g (33 mmol) of N-bromosuccinimide, and the resultant was heated under reflux for 7 hours. After completion of the reaction, the reaction solution was poured to 500 mL of water, and deposited solids were filtered off. The solids which were filtered off were dissolved in ethyl acetate, and dried with magnesium sulfate. After filtration, the solvent was distilled off under reduced pressure at room temperature, whereby 7.1 g (yield 93%) of orange solids of 4-bromo-N-methyl-2-nitroaniline were obtained.

(E-2) Synthesis of 4'-bromo-N-methyl-2'-nitrobenzanilide 6.8 g (29 mmol) of 4-bromo-N-methyl-2-nitroaniline was dissolved in 20 mL of pyridine. To the resulting solution, 5.0 g (35 mmol) of benzoyl chloride was added, and the resulting mixture was stirred with heating at 90° C. for 7 hours in the atmosphere of argon. After completion of the reaction, 200 mL of ethyl acetate was added, and an organic phase was washed with an aqueous 10% hydrochloric acid solution, an aqueous 10% potassium carbonate solution and saturated saline, and then dried with magnesium sulfate. After filtration, the solvent was distilled off under reduced pressure, and residues were purified by silica gel column chromatography, whereby 9.5 g (yield 96%) of greenish white solids of 4'-bromo-N-methyl-2'-nitrobenzanilide were obtained.

(E-3) Synthesis of 4'-bromo-N-methyl-2'-aminobenzanilide 9.5 g (28 mmol) of 4'-bromo-N-methyl-2'-nitrobenzanilide was dissolved in 100 mL of tetrahydrofuran. In the atmosphere of argon, while stirring at room temperature, a solution of 25 g (142 mmol) of sodium hydrosulfite/90 mL of water was added. Further, 10 mL of methanol was added, followed by stirring for 3 hours. Next, 100 mL of ethyl acetate was added, and a solution of 12 g (142 mmol) of sodium hydrogen carbonate/125 mL of water was added. After stirring at room temperature for 1 hour, extraction was conducted with ethyl acetate. After removing an aqueous phase, an organic phase was washed with an aqueous 10% potassium carbonate solution and saturated saline, and dried with magnesium sulfate. After filtration, the solvent was distilled off under reduced pressure, whereby 7.8 g (yield 90%) of white crystals of 4'-bromo-N-methyl-2'-aminobenzanilide were obtained.

(E-4) Synthesis of 5-bromo-1-methyl-2-phenyl-1H-benzimidazole 7.8 g (26 mmol) of 4'-bromo-N-methyl-2'-aminobenzanilide was suspended in 50 mL of xylene. To the resulting suspension, 1.5 g (7.7 mmol) of p-toluenesulfonic monohydrate was added, followed by heating under reflux for 7 hours. After completion of the reaction, the solution was filtrated. The resulting solids were dissolved in methylene chloride, washed with an aqueous 10% potassium chloride solution and saturated saline and dried with magnesium sulfate. The solvent was distilled off under reduced pressure. Organic matters were recovered from the filtrate in the same manner. The solids and organic matters were purified by silica gel column chromatography, whereby 6.5 g (yield 89%) of white crystals of 5-bromo-1-methyl-2-phenyl-1H-benzimidazole were obtained.

Synthesis Example 6

(F) 2-(4-bromophenyl)-imidazo[1,2-a]pyridine 15 g (54 mmol) of 4-bromophenacyl bromide and 5.2 g (55 mmol) of 2-aminopyridine were dissolved in 100 mL of ethanol. Then, 7.0 g of sodium hydrogen carbonate was added, and the resultant was heated under reflux for 6 hours. After completion of the reaction, generated crystals were filtered out, washed with water and ethanol, whereby 12.5 g (yield 85%) of 2-(4-bromophenyl)-imidazo[1,2-a]pyridine was obtained.

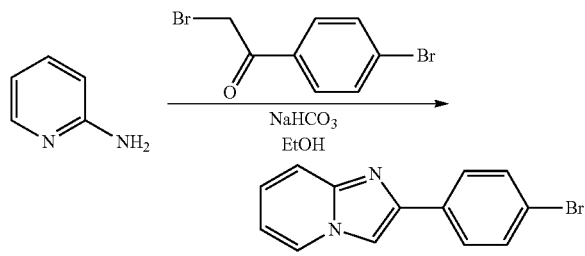

Synthesis Example 7

(G) Synthesis of 2-(3-bromophenyl)-imidazo[1,2-a]pyridine

As shown by the following synthesis scheme, a reaction was conducted in the same manner as in Synthesis Example 6, except that 3-bromophenacyl bromide was used instead of 4-bromophenacyl bromide, whereby 2-(3-bromophenyl)-imidazo[1,2-a]pyridine was synthesized.

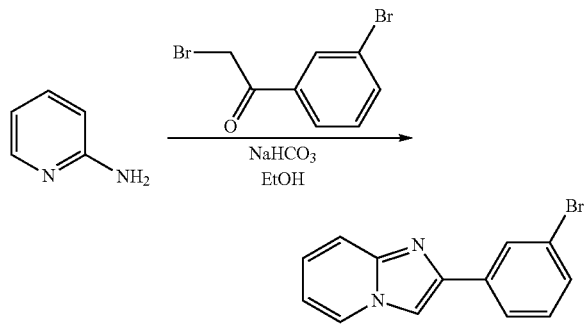

Synthesis Example 8

(H) Synthesis of 4-(fluoranthen-3-yl)phenylboronic acid

According to the following synthesis scheme, 4-(fluoranthen-3-yl)phenylboronic acid was synthesized.

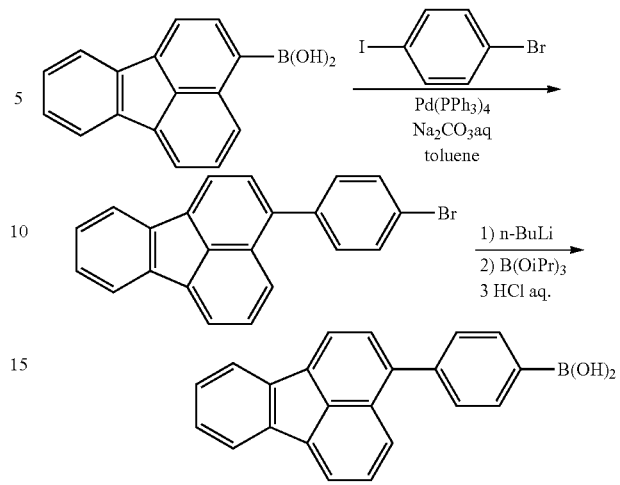

(H-1) Synthesis of 3-(4-bromophenyl)fluoranthene

In the atmosphere of argon, 9.1 g of fluoranthene-3-boronic acid, 10.5 g of 4-bromoiodobenzene, 2.1 g of tetrakis(triphenylphosphine)palladium(0), 186 mL of toluene and 74 mL of an aqueous 2M solution of sodium carbonate were placed in a flask, and stirred at 100° C. for 8 hours. After cooling to room temperature, the reaction solution was extracted with toluene. After removing an aqueous phase, an organic phase was washed with saturated saline, and dried with anhydrous sodium sulfate. After filtration, the solvent was distilled off under reduced pressure, and residues were purified by silica gel column chromatography, whereby 9.2 g (yield 70%) of 3-(4-bromophenyl)fluoranthene as an intended product was obtained.

(H-2) Synthesis of 4-(fluoranthen-3-yl)phenylboronic acid

In the atmosphere of argon, 9.2 g of 3-(4-bromophenyl)fluoranthene and 129 mL of tetrahydrofuran were placed in a flask. The reaction solution was cooled to −70° C., and 17.2 mL of a 1.65M hexane solution of n-butyllithium was added dropwise. Stirring was conducted at −70° C. for 2 hours. To the reaction solution, 17.7 mL of triisopropyl borate was added dropwise, and the resultant was stirred at −70° C. for 1 hour. While heating the reaction solution to room temperature, stirring was conducted for 5 hours. 2M hydrochloric acid was added to the reaction liquid to allow it to be acidic, and the reaction solution was extracted with ethyl acetate. After removing an aqueous phase, an organic phase was washed with saturated saline, and dried with anhydrous sodium sulfate. After filtration, the solvent was distilled off under reduced pressure, residues were washed with a hexane-ethyl acetate mixed solution, whereby 7.9 g (yield 95%) of 4-(fluoranthen-3-yl)phenylboronic acid was obtained.

Synthesis Example 9

(I) Synthesis of 3-(fluoranthen-3-yl)phenylboronic acid

As shown by the following synthesis scheme, a reaction was conducted in the same manner as in Synthesis Example 8, except that 3-iodobromobenzene was used instead of 4-bromoiodebenzene, whereby 3-(fluoranthene-3-yl)phenylboronic acid was synthesized.

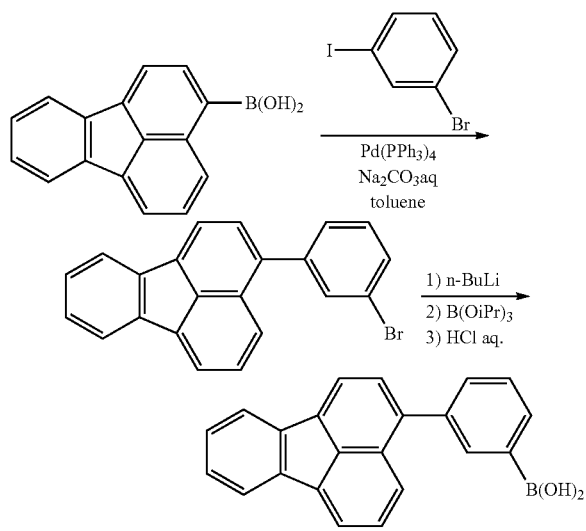

Synthesis Example 10

(J) Synthesis of
6-(fluoranthen-3-yl)naphthalene-2-ylboronic acid
pinacol ester

According to the following synthesis scheme, 6-(fluoranthen-3-yl)naphthalene-2-ylboronic acid pinacol ester was synthesized.

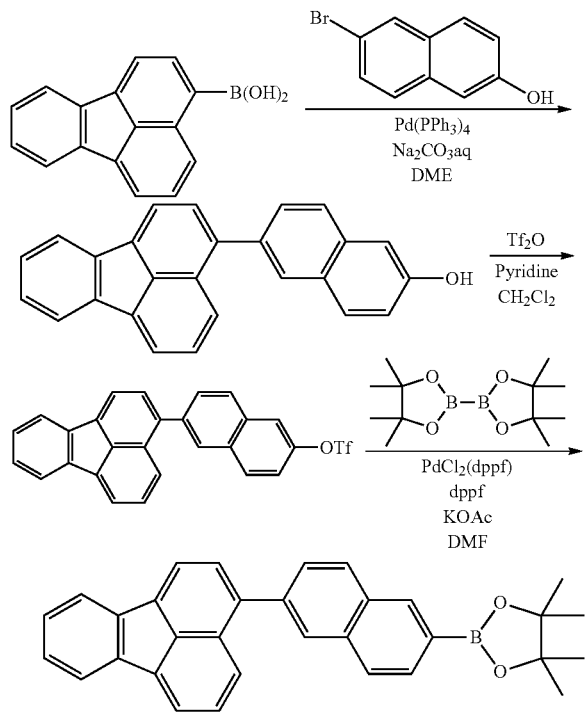

(J-1) Synthesis of 6-(fluoranthen-3-yl)-2-naphthol

Under the atmosphere of argon, 2.7 g of fluoranthene-3-boronic acid, 2.0 g of 6-bromo-2-naphthol, 0.31 g of tetrakis(triphenylphosphine)palladium (0), 27 mL of 1,2-dimethoxyethane and 13.5 mL of an aqueous 2M sodium carbonate solution were placed in a flask, and the resulting mixture was stirred under reflux while heating for 4 hours. After cooling to room temperature, 2M hydrochloric acid was added to the reaction solution to allow it to be acidic, and the reaction solution was extracted with dichloromethane. An aqueous phase was removed and an organic phase was washed with saturated saline, and dried with anhydrous sodium sulfate. After filtration, the solvent was distilled off under reduced pressure, residues were dispersed and washed with dichloromethane, whereby 2.75 g (yield 89%) of 6-(fluoranthen-3-yl)-2-naphthol as an intended product was obtained.

(J-2) Synthesis of 6-(fluoranthen-3-yl)-2-trifluoromethanesulfoxynaphthalene

Under the atmosphere of argon, 2.75 g of 6-(fluoranthen-3-yl)-2-naphthol, 2 mL of pyridine and 80 mL of dichloromethane were placed in a flask. While cooling on ice, 2 mL of anhydrous trifluoromethanesulfonic acid was added dropwise to the reaction liquid. After stirring for 20 minutes, stirring was conducted for 3 hours while heating to room temperature. 0.5 mL of trifluoromethanesulfonic acid was added dropwise to the reaction liquid, and the resultant was stirred for 30 minutes. Water was carefully added dropwise to the reaction liquid to quench the reaction. Thereafter, 200 mL of 0.5M hydrochloric acid was added, and extraction was conducted with dichloromethane. An aqueous phase was removed, and an organic phase was dried with anhydrous sodium sulfate. After the filtration, the solvent was distilled off under reduced pressure, residues were recrystallized from toluene, whereby 3.11 g (yield 82%) of 6-(fluoranthen-3-yl)-2-trifluoromethanesulfoxynaphthalene as an intended product was obtained.

(J-3) Synthesis of
6-(fluoranthen-3-yl)naphthalene-2-ylboronic acid
pinacol ester Under the atmosphere of argon, 3.11 g of 6-(fluoranthen-3-yl)-2-trifluoromethanesulfoxynaphthalene, 1.83 g of bispinacolatodiboron, [1,1'-bis(diphenylphosphino)ferrocene]palladium (II) dichloride dichloromethane adduct (0.27 g), 1,1'-bis(diphenylphosphino)ferrocene (0.18 g), potassium acetate (1.93 g) and 65 mL of dimethylformamide were placed in a flask, and the resulting mixture was stirred at 80° C. for 8 hours. After cooling to room temperature, water was added to the reaction liquid. Then, the mixture was extracted with toluene. The resulting toluene solution was passed through a silica gel short column, whereby the solvent of the eluent was distilled off under reduced pressure. Residues were recrystallized from toluene, whereby 1.53 g (yield 52%) of 6-(fluoranthen-3-yl)naphthalene-2-ylboronic acid pinacol ester as an intended product was obtained.

Synthesis of Nitrogen-Containing Heterocyclic
Derivative

Example 1

In the atmosphere of argon, 3.0 g of benzo[c]phenanthrene-5-boronic acid, 3.5 g of 1-(4-bromophenyl)-2-phenyl- 1H-benzimidazole, 0.231 g of tetrakis(triphenylphosphine) palladium (0), 40 mL of dimethoxyethane and 20 mL of a 2M aqueous solution of sodium carbonate were placed in a flask, and the resultant was stirred under reflux with heating for 8 hours. After cooling to room temperature, the reaction solution was extracted with toluene. After removing an aqueous phase, an organic phase was washed with water and dried with magnesium sulfate. After filtration, the solvent was distilled off under reduced pressure, residues were purified by silica gel column chromatography, whereby 3.8 g of pale yellow solids were obtained. As a result of mass spectroscopy, the resulting compound was found to be the following compound 1 and had an m/e value of 496 relative to the molecular weight of 496.19.

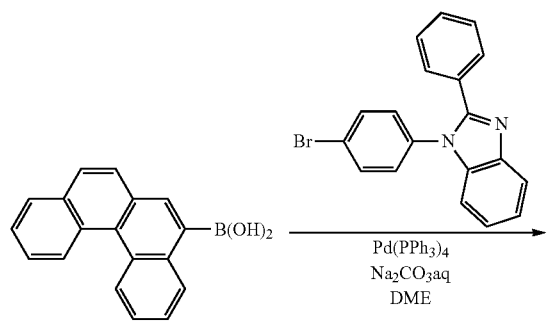

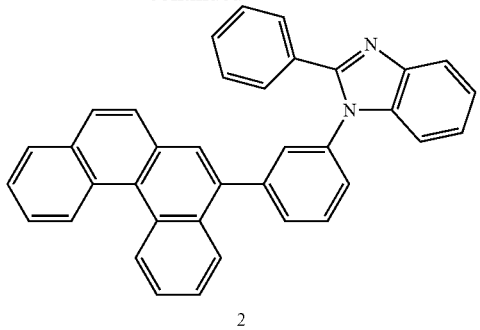

2

Example 3

A reaction was conducted in the same manner as in Example 1, except that 5-bromo-1-methyl-2-phenyl-1H-benzimidazole was used instead of 1-(4-bromophenyl)-2-phenyl-1H-benzimidazole.

As a result of mass spectroscopy, the resulting compound was found to be the following compound 3 and had an m/e value of 434 relative to the molecular weight of 434.18.

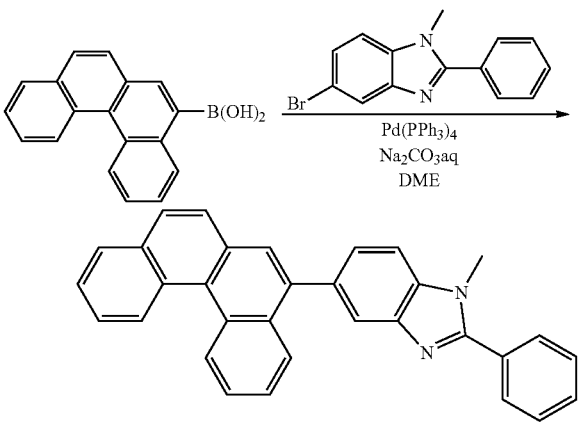

1

Example 2

A reaction was conducted in the same manner as in Example 1, except that 1-(3-bromophenyl)-2-phenyl-1H-benzimidazole was used instead of 1-(4-bromophenyl)-2-phenyl-1H-benzimidazole.

As a result of mass spectroscopy, the resulting compound was found to be the following compound 2 and had an m/e value of 496 relative to the molecular weight of 496.19.

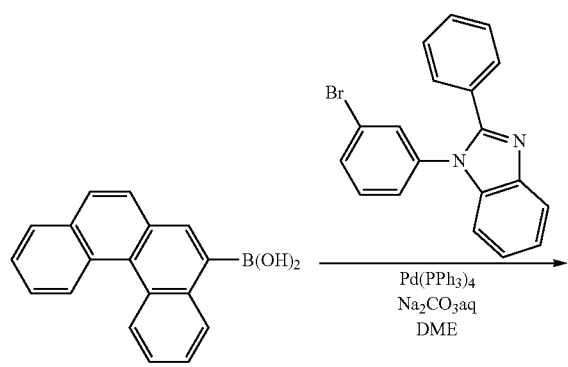

3

Example 4

A reaction was conducted in the same manner as in Example 1, except that 2-(4-bromophenyl)-imidazo[1,2-a]pyridine was used instead of 1-(4-bromophenyl)-2-phenyl-1H-benzimidazole.

As a result of mass spectroscopy, the resulting compound was found to be the following compound 4 and had an m/e value of 420 relative to the molecular weight of 420.16.

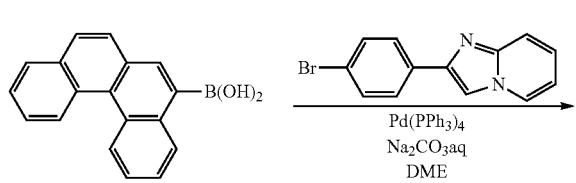

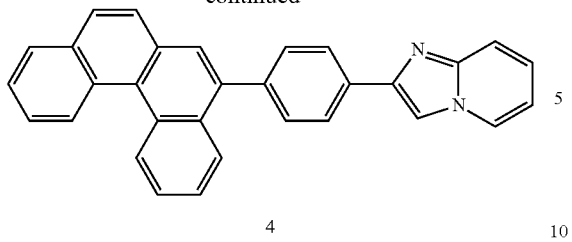

4

Example 5

A reaction was conducted in the same manner as in Example 1, except that 2-(3-bromophenyl)-imidazo[1,2-a]pyridine was used instead of 1-(4-bromophenyl)-2-phenyl-1H-benzimidazole.

As a result of mass spectroscopy, the resulting compound was found to be the following compound 5 and had an m/e value of 420 relative to the molecular weight of 420.16.

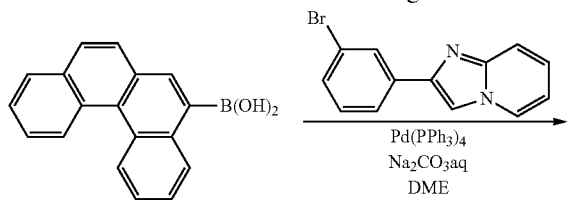

5

Example 6

A reaction was conducted in the same manner as in Example 1, except that benzo[g]chrysene-10-boronic acid was used instead of benzo[c]phenanthrene-5-boronic acid.

As a result of mass spectroscopy, the resulting compound was found to be the following compound 6 and had an m/e value of 546 relative to the molecular weight of 546.21.

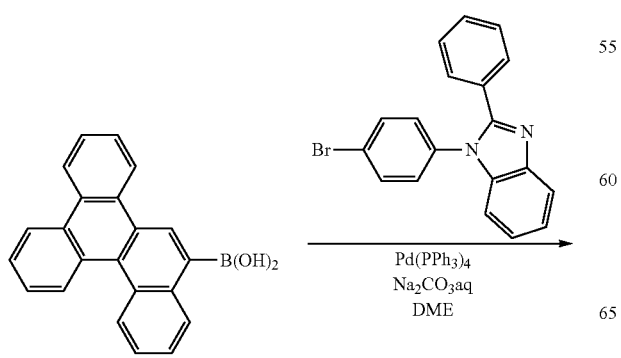

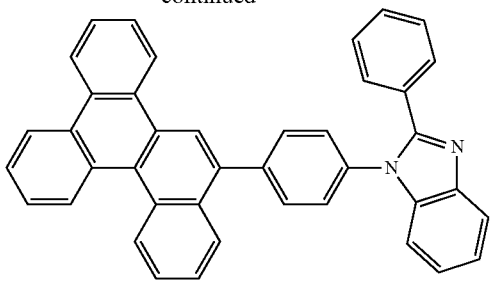

6

Example 7

A reaction was conducted in the same manner as in Example 1, except that benzo[g]chrysene-10-boronic acid was used instead of benzo[c]phenanthrene-5-boronic acid and 1-(3-bromophenyl)-2-phenyl-1H-benzimidazole was used instead of 1-(4-bromophenyl)-2-phenyl-1H-benzimidazole.

As a result of mass spectroscopy, the resulting compound was found to be the following compound 7 and had an m/e value of 546 relative to the molecular weight of 546.21.

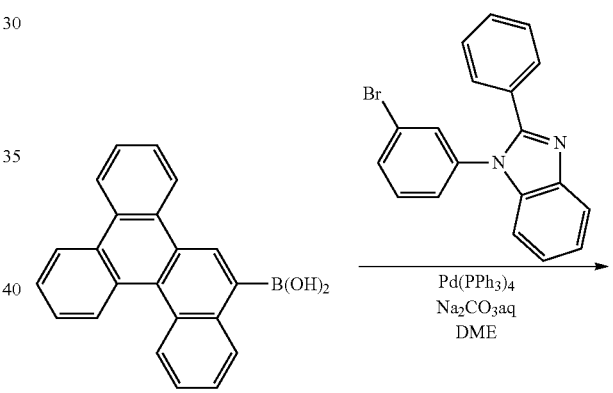

7

Example 8

A reaction was conducted in the same manner as in Example 1, except that benzo[g]chrysene-10-boronic acid was used instead of benzo[c]phenanthrene-5-boronic acid and 5-bromo-1-methyl-2-phenyl-1H-benzimidazole was used instead of 1-(4-bromophenyl)-2-phenyl-1H-benzimidazole.

As a result of mass spectroscopy, the resulting compound was found to be the following compound 8 and had an m/e value of 484 relative to the molecular weight of 484.19.

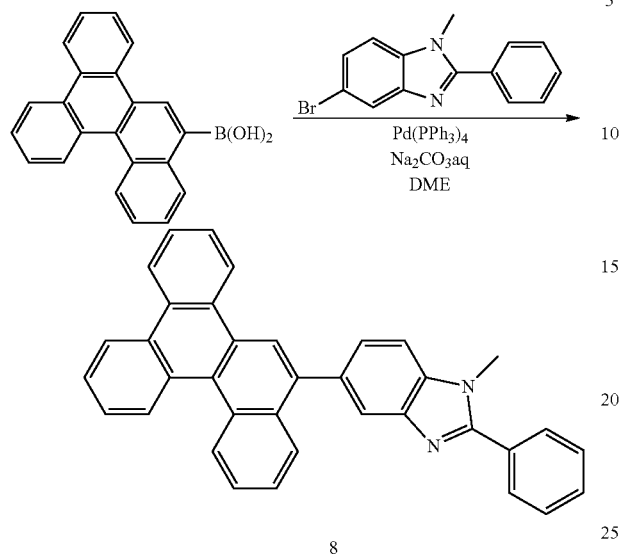

8

Example 9

A reaction was conducted in the same manner as in Example 1, except that benzo[g]chrysene-10-boronic acid was used instead of benzo[c]phenanthrene-5-boronic acid and 2-(4-bromophenyl)-imidazo[1,2-a]pyridine was used instead of 1-(4-bromophenyl)-2-phenyl-1H-benzimidazole.

As a result of mass spectroscopy, the resulting compound was found to be the following compound 9 and had an m/e value of 470 relative to the molecular weight of 470.18.

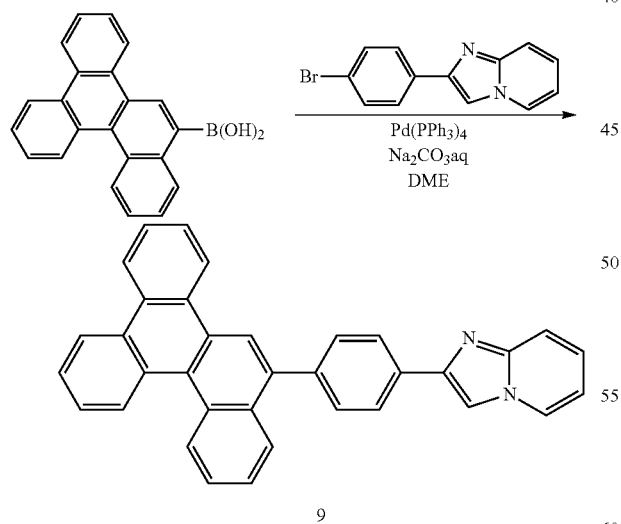

9

Example 10

A reaction was conducted in the same manner as in Example 1, except that benzo[g]chrysene-10-boronic acid was used instead of benzo[c]phenanthrene-5-boronic acid and 2-(4-bromophenyl)-imidazo[1,2-a]pyridine was used instead of 1-(3-bromophenyl)-2-phenyl-1H-benzimidazole.

As a result of mass spectroscopy, the resulting compound was found to be the following compound 10 and had an m/e value of 470 relative to the molecular weight of 470.18.

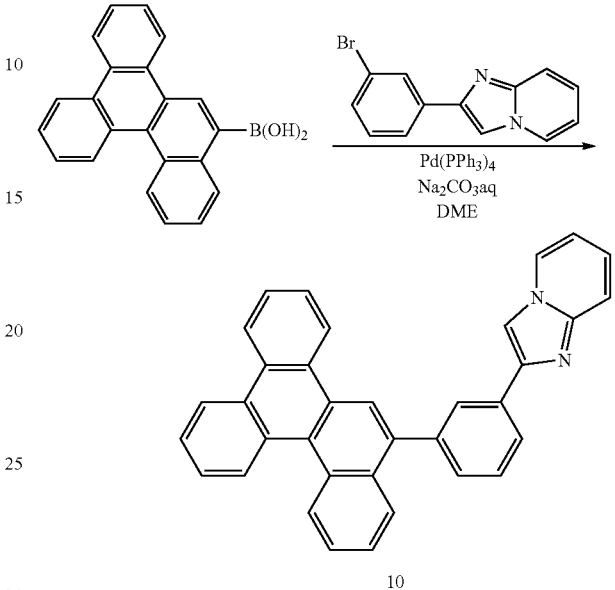

10

Example 11

In the atmosphere of argon, 2.7 g of fluoranthene-3-boronic acid, 3.5 g of 1-(4-bromophenyl)-2-phenyl-1H-benzimidazole which was synthesized in Synthesis Example 3, 0.231 g of tetrakis(triphenylphosphine)palladium(0), 40 mL of dimethoxyethane and 20 mL of a 2M aqueous sodium carbonate solution were placed in a flask. The resulting mixture was stirred under reflux with heating for 8 hours. After cooling to room temperature, the reaction solution was extracted with toluene. After removing an aqueous phase, an organic phase was washed with water, and dried with magnesium sulfate. After filtration, the solvent was distilled off under reduced pressure, residues were purified by silica gel column chromatography, whereby 3.4 g of pale yellow solids were obtained. As a result of mass spectroscopy, the resulting compound was found to be the following compound 11 and had an m/e value of 470 relative to the molecular weight of 470.18.

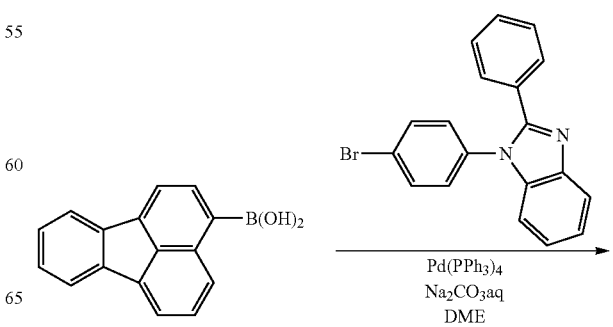

-continued

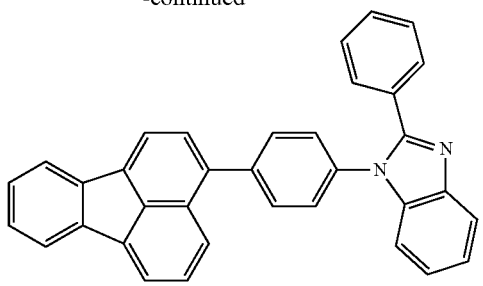

11

Example 12

Synthesis was conducted in the same manner as in the synthesis of the compound 11, except that 1-(3-bromophenyl)-2-phenyl-1H-benzimidazole which was synthesized in Synthesis Example 4 was used instead of 1-(4-bromophenyl)-2-phenyl-1H-benzimidazole.

As a result of mass spectroscopy, the resulting compound was found to be the following compound 12 and had an m/e value of 470 relative to a molecular weight of 470.18.

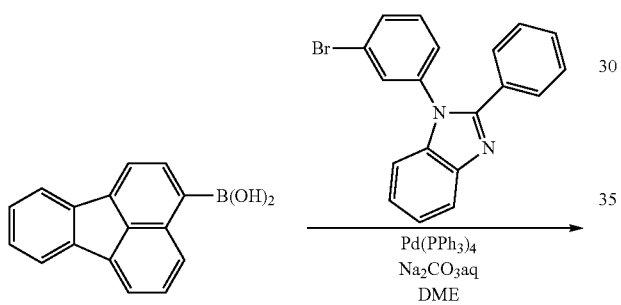

12

Example 13

Synthesis was conducted in the same manner as in the synthesis of the compound 11, except that 5-bromo-1-methyl-2-phenyl-1H-benzimidazole which was synthesized in Synthesis Example 5 was used instead of 1-(4-bromophenyl)-2-phenyl-1H-benzimidazole.

As a result of mass spectroscopy, the resulting compound was found to be the following compound 13 and had an m/e value of 408 relative to a molecular weight of 408.16.

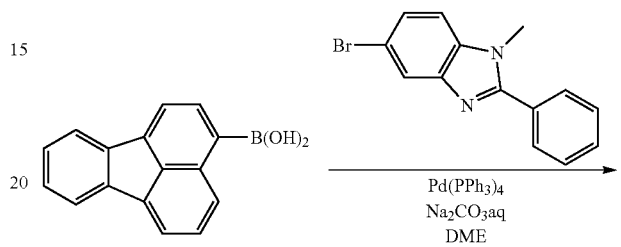

13

Example 14

Synthesis was conducted in the same manner as in the synthesis of the compound 11, except that 4-(fluororanthen-3-yl)phenylboronic acid which was synthesized in Synthesis Example 8 was used instead of fluoranthene-3-boronic acid.

As a result of mass spectroscopy, the resulting compound was found to be the following compound 14 and had an m/e value of 546 relative to a molecular weight of 546.21.

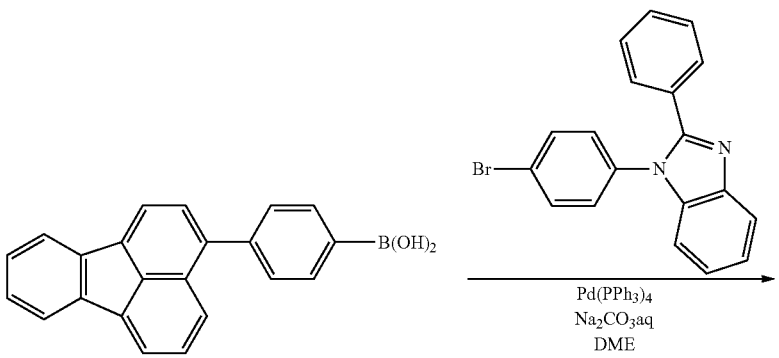

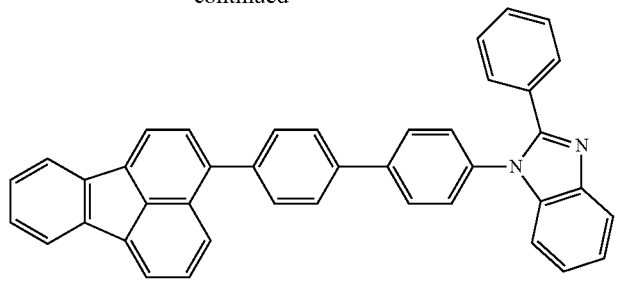

14

Example 15

Synthesis was conducted in the same manner as in the synthesis of the compound 11, except that 3-(fluoranthen-3-yl)phenylboronic acid which was synthesized in Synthesis Example 9 was used instead of fluoranthene-3-boronic acid. As a result of mass spectroscopy, the resulting compound was found to be the following compound 15 and had an m/e value of 546 relative to a molecular weight of 546.21.

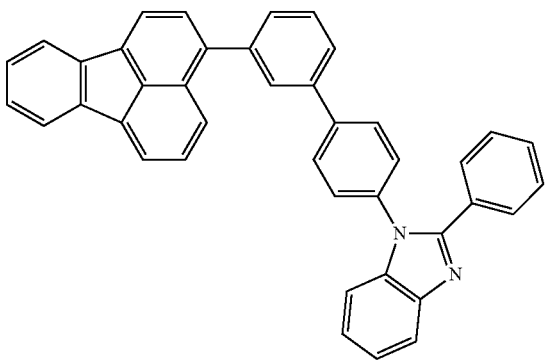

-continued

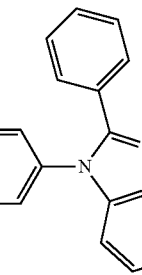

15

Example 16

Synthesis was conducted in the same manner as in the synthesis of the compound 11, except that 6-(fluoranthen-3-yl)naphthalene-2-ylboronic acid pinacol ester which was synthesized in Synthesis Example 10 was used instead of fluoranthene-3-boronic acid, and 1-(3-bromophenyl)-2-phenyl-1H-benzimidazole which was synthesized in Synthesis Example 4 was used instead of 1-(4-bromophenyl)-2-phenyl-1H-benzimidazole. As a result of mass spectroscopy, the resulting compound was found to be the following compound 16 and had an m/e value of 596 relative to a molecular weight of 596.23.

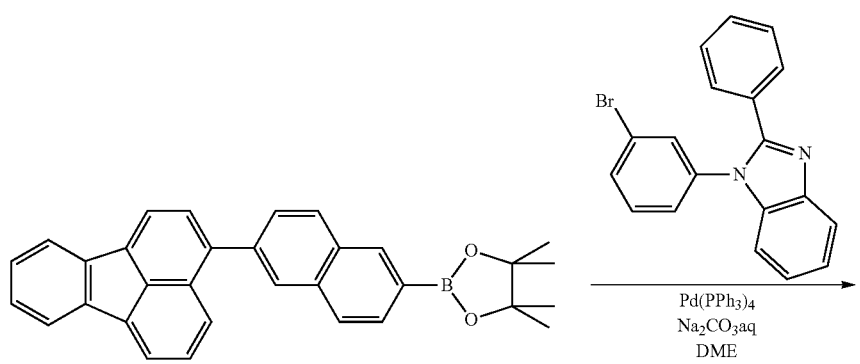

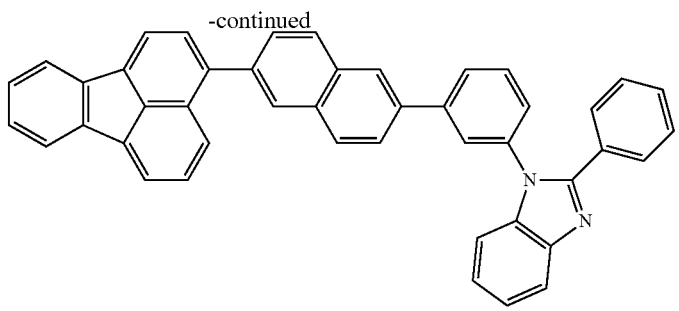

16

Example 17

Synthesis was conducted in the same manner as in the synthesis of the compound 11, except that 3-(fluoranthen-3-yl)phenylboronic acid which was synthesized in Synthesis Example 9 was used instead of fluoranthene-3-boronic acid, and 5-bromo-1-methyl-2-phenyl-1H-benzimidazole which was synthesized in Synthesis Example 5 was used instead of 1-(4-bromophenyl)-2-phenyl-1H-benzimidazole. As a result of mass spectroscopy, the resulting compound was found to be the following compound 17 and had an m/e value of 484 relative to a molecular weight of 484.19.

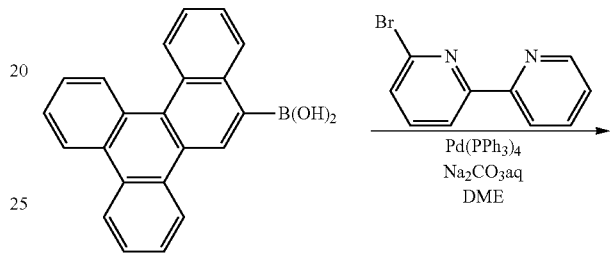

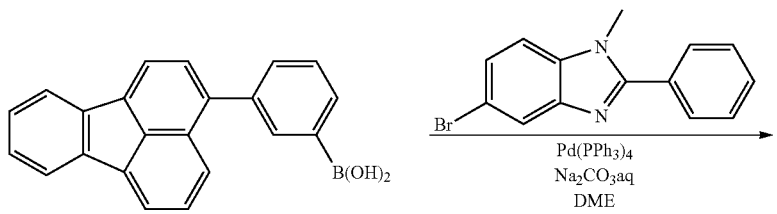

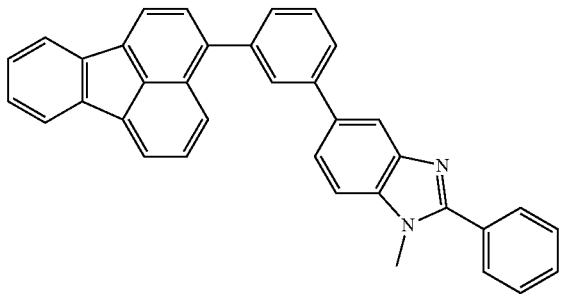

17

Example 18

A reaction was conducted in the same manner as in Example 1, except that benzo[g]chrysene-10-boronic acid was used instead of benzo[c]phenanthrene-5-boronic aid and 6-bromo-2,2'-bipyridyl was used instead of 1-(4-bromophenyl)-2-phenyl-1H-benzimidazole.

As a result of mass spectroscopy, the resulting compound was found to be the following compound 18 and had an m/e value of 432 relative to a molecular weight of 432.16.

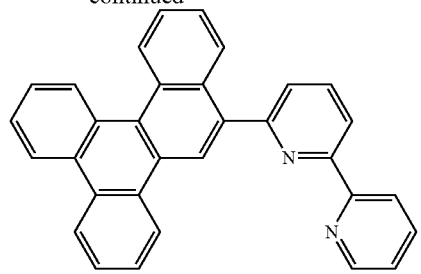

18

Fabrication of Organic EL Device
Example 19
The materials used in an organic EL device are as follows.
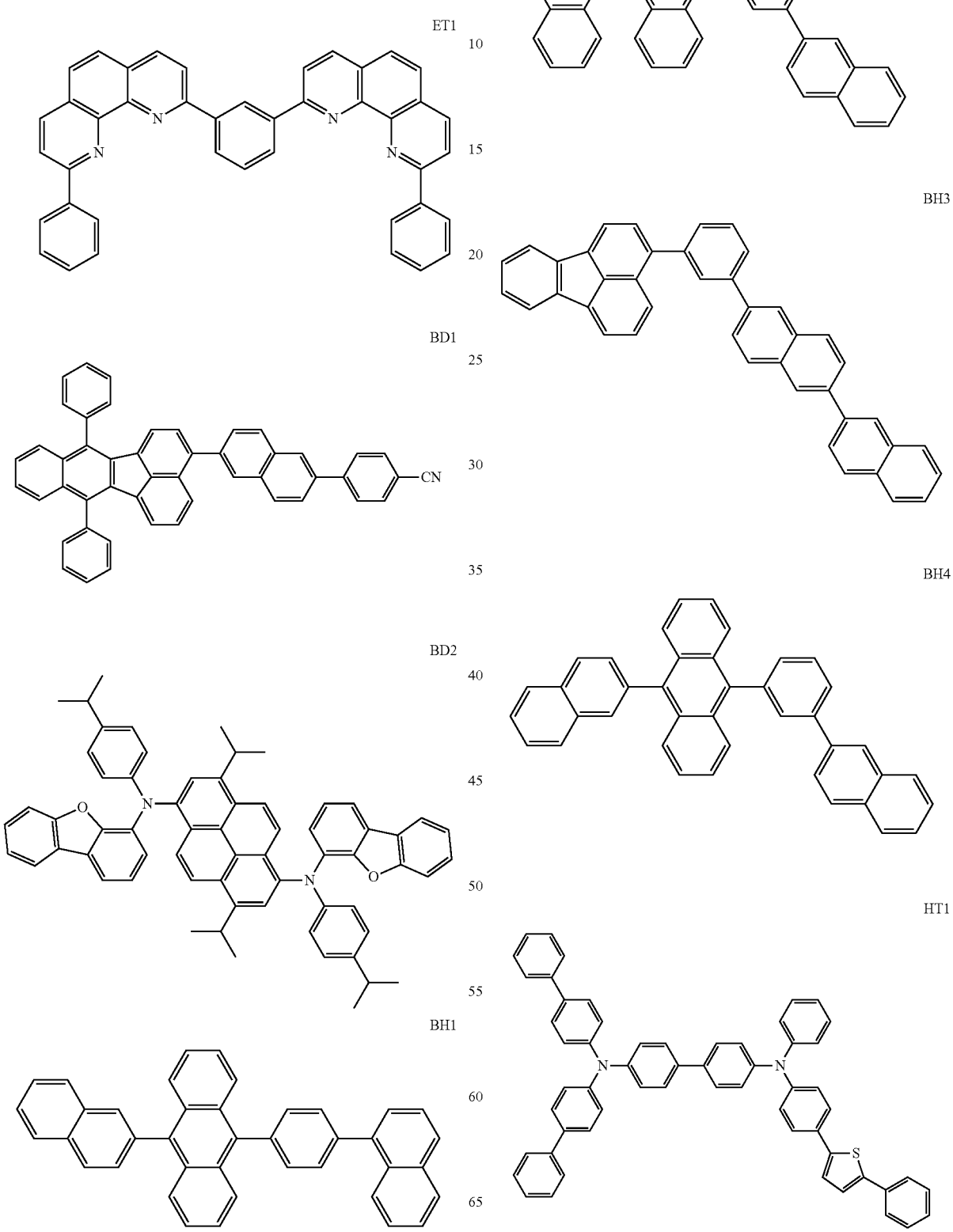

-continued

HT2

On a substrate on which a 130 nm-thick ITO (indium tin oxide) was formed, the following materials were sequentially deposited, whereby an organic EL device was obtained. The number in parenthesis (unit:nm) indicates the film thickness.
Anode: ITO (130)
Hole-injecting layer: HT1 (50)
Hole-transporting layer: HT2 (45)
Emitting layer: BH1 and BD1 (BD1 was doped in an amount of 5%) (25)
Blocking layer: Compound 6 (25)
Low-work function metal containing layer: LiF (1)
Cathode Al (80)

The following evaluation was made on the thus obtained organic EL device. The results are shown in Table 1.
(1) Initial Performance (Voltage, Chromaticity, Current Efficiency, External Quantum Efficiency, Main Peak Wavelength)

A voltage was applied to the device such that the current value became 10 mA/cm$^2$, and the voltage value at this time was measured. An EL emission spectrum at this time was measured by means of a spectroradiometer (CS-1000, manufactured by Konica Minolta Holdings, Inc.). From the resulting spectra radiance, chromaticity, current efficiency (cd/A) and external quantum efficiency (%) were calculated.
(2) Ratio of Emission Derived from TTF A voltage pulse waveform (pulse width: 500 microseconds, frequency: 20 Hz) which has been output from a pulse generator (8114A, manufactured by Adilent Corporation) was applied to a device. EL emission was input to a photomultiplier tube (R928 manufactured by Hamamatsu Photonics K.K.), and a pulse voltage waveform and EL emission were synchronized and input to an oscilloscope (2440, manufactured by Tektronix, Inc.) to obtain a transient EL waveform. Ratio of emission derived from TTF (TTF ratio) was determined by analyzing this EL waveform (see Japanese Patent Application No. 2009-125883).

The transient EL waveform was obtained by measuring the current density when the current efficiency (L/J) became the maximum in a current density-current efficiency curve, followed by application of a voltage pulse waveform corresponding to the current density.

The theoretical limit of Improvement in internal quantum efficiency by a TTF phenomenon is thought to be 62.5%. In this case, the ratio of emission derived from TTF is 60%.
(3) Method for Measuring Internal Quantum Efficiency According to the method stated in JP-A-2006-278035, the emission distribution and the outcoupling efficiency in the emission layer were determined. Thereafter, an EL spectrum measured by a spectroradiometer was divided by the thus determined outcoupling efficiency to obtain an internal EL spectrum. The ratio of the number of photons generated in the inside obtained from the spectrum and the number of electrons was taken as the internal quantum efficiency.

Examples 20 to 27 and Comparative Examples 1 and 2

Organic EL devices were fabricated and evaluated in the same manner as in Example 19, except that the compounds shown in Table 1 were used as the host material, and the dopant material in the emitting layer and the blocking layer material. The results obtained are shown in Table 1.

TABLE 1

|  | BH | BD | ET | Voltage [V] | Chromaticity x | Chromaticity y | L/J [cd/A] | EQE [%] | TTF ratio [%] |
|---|---|---|---|---|---|---|---|---|---|
| Example 19 | BH1 | BD1 | Compound 6 | 3.6 | 0.144 | 0.117 | 9.6 | 9.3 | 33 |
| Example 20 | BH2 | BD1 | Compound 6 | 3.7 | 0.143 | 0.116 | 9.9 | 9.7 | 34 |
| Example 21 | BH1 | BD1 | Compound 12 | 3.7 | 0.145 | 0.110 | 8.0 | 8.1 | 28 |
| Example 22 | BH2 | BD1 | Compound 12 | 3.8 | 0.144 | 0.110 | 8.5 | 8.6 | 28 |
| Example 23 | BH2 | BD2 | Compound 1 | 4.3 | 0.128 | 0.147 | 10.6 | 9.3 | 26 |
| Example 24 | BH4 | BD1 | Compound 15 | 3.9 | 0.143 | 0.118 | 9.0 | 8.8 | 32 |
| Example 25 | BH4 | BD1 | Compound 16 | 3.9 | 0.142 | 0.123 | 8.6 | 8.1 | 28 |
| Example 26 | BH4 | BD1 | Compound 17 | 3.8 | 0.142 | 0.124 | 10.0 | 9.4 | 31 |
| Example 27 | BH4 | BD1 | Compound 18 | 4.8 | 0.143 | 0.121 | 7.6 | 7.2 | 34 |
| Com. Ex. 1 | BH1 | BD1 | ET1 | 3.2 | 0.144 | 0.124 | 7.2 | 6.7 | 22 |
| Com. Ex. 2 | BH1 | BD1 | BH3 | 5.9 | 0.143 | 0.115 | 0.5 | 0.5 | 13 |

INDUSTRIAL APPLICABILITY

An organic EL device comprising the nitrogen-containing heterocyclic derivative of the invention can be used for a display panel or an illumination panel or the like used in large-sized televisions of which the reduction in power consumption is desired.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:
1. A nitrogen-containing heterocyclic derivative represented by formula (1):

(1)

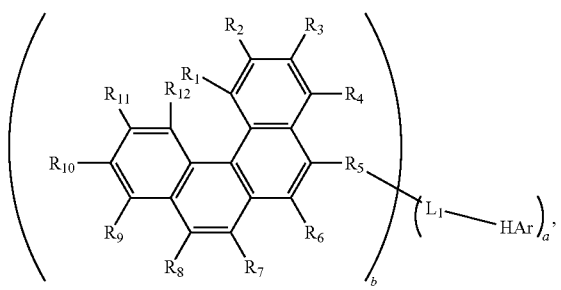

wherein:

$R_1$ to $R_{12}$ are independently a hydrogen atom, a fluorine atom, a substituted or unsubstituted aryl group having 6 to 30 ring carbon atoms, a substituted or unsubstituted heterocyclic group having 5 to 30 ring atoms or a single bond that is bonded to $L_1$;

$L_1$ is a single bond, a "b+1" valent substituted or unsubstituted hydrocarbon ring having 6 to 30 ring carbon atoms or a "b+1" valent substituted or unsubstituted heterocyclic group having 5 to 30 ring atoms;

HAr is a nitrogen-containing heterocyclic group represented by a formula (10)-(16):

(10)

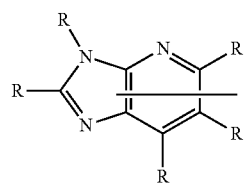

(11)

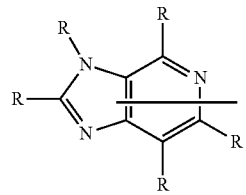

(12)

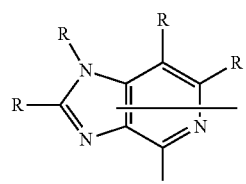

(13)

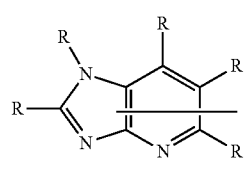

(14)

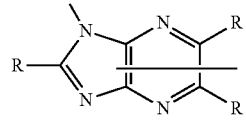

(15)

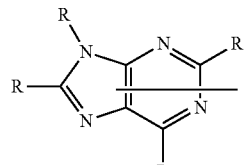

(16)

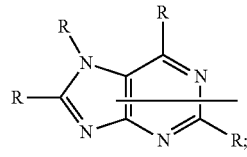

wherein any of the R groups which substitutes the heterocyclic skeleton of formulas (10) to (16) is a single bond and is bonded to $L_1$, and the other R groups are independently a hydrogen atom or a substituent of at least two adjacent groups thereof combined to form a saturated or unsaturated ring; and a and b are independently an integer of 1 to 4, such that at least one of a and b is 1.

2. The nitrogen-containing heterocyclic derivative of claim 1, wherein a is 1.

3. The nitrogen-containing heterocyclic derivative of claim 1 which is a material for an organic electroluminescence device.

4. The nitrogen-containing heterocyclic derivative of claim 3, wherein the material for an organic electroluminescence device is a material for a blocking layer.

5. An organic electroluminescence device, comprising an anode, an emitting layer, a blocking layer and a cathode sequentially, wherein the blocking layer comprises the nitrogen-containing heterocyclic derivative of claim 1.

6. An organic electroluminescence device, comprising an electron-injecting layer, an electron-transporting layer, or both, between an emitting layer and a cathode, wherein at least one layer of the electron-injecting layer and the electron-transporting layer comprises the nitrogen-containing heterocyclic derivative of claim 1.

7. The organic electroluminescence device of claim 5, wherein the emitting layer comprises an anthracene derivative represented by formula (41):

(41)

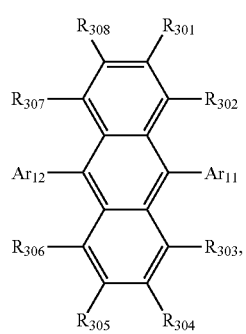

wherein:

$Ar_{11}$ and $Ar_{12}$ are independently a substituted or unsubstituted aryl group having 6 to 30 ring carbon atoms or a substituted or unsubstituted heterocyclic group having 5 to 30 ring atoms; and $R_{301}$ to $R_{308}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms.

8. The organic electroluminescence device of claim 7, wherein the emitting layer comprising the anthracene derivative represented by the formula (41) is adjacent to the blocking layer comprising the nitrogen-containing heterocyclic derivative.

9. A nitrogen-containing heterocyclic derivative represented by formula (21):

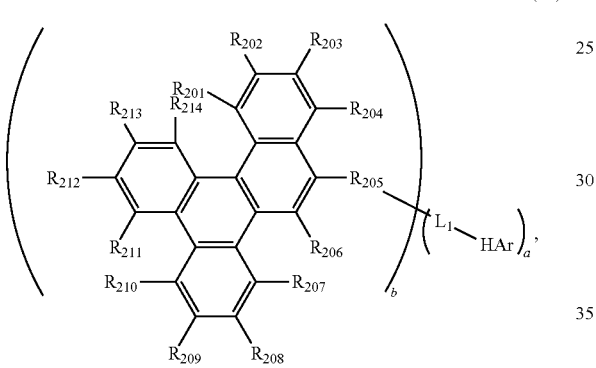

(21)

wherein:
$R_{201}$ to $R_{214}$ are independently a hydrogen atom, a fluorine atom, a substituted or unsubstituted alkyl group having 1 to 10 carbon atoms, a substituted or unsubstituted cycloalkyl group having 3 to 8 carbon atoms, a substituted or unsubstituted alkylsilyl group having 3 to 30 carbon atoms, a substituted or unsubstituted arylsily group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted phenyl group, a substituted or unsubstituted naphthyl group, a substituted or unsubstituted phenyanthryl group, a substituted or unsubstituted biphenyl group, a substituted or unsubstituted terphenyl group, a substituted or unsubstituted chrysenyl group, a substituted or unsubstituted benzophenanthryl group, a substituted or unsubstituted benzochrysenyl group, a substituted or unsubstituted fluorenyl group, a substituted or unsubstituted fluoranthenyl group, a substituted or unsubstituted heterocyclic group having 5 to 30 ring atoms, or a single bond that is bonded to $L_1$;

$L_1$ is a single bond, a substituted or unsubstituted phenylene group, a substituted or unsubstituted naphthylene group, a substituted or unsubstituted biphenylene group, a substituted or unsubstituted triphenylene group, a substituted or unsubstituted picenylene group, a substituted or unsubstituted pyrenylene group, a substituted or unsubstituted pentaphenylene group, a substituted or unsubstituted fluorenylene group, a substituted or unsubstituted chrysenylene group or a substituted or unsubstituted "b+1" valent heterocyclic group having 5 to 30 ring atoms;

HAr is any of the nitrogen-containing heterocylic groups represented by the following formulas (7), (9) to (16) and (i):

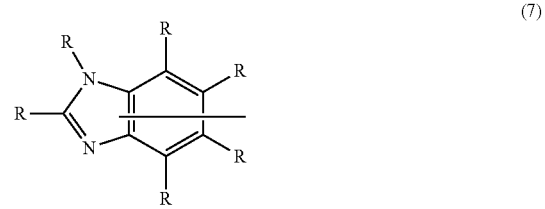
(7)

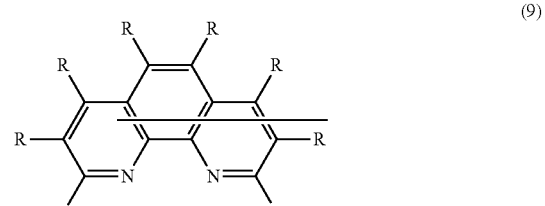
(9)

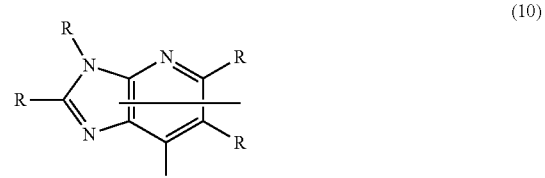
(10)

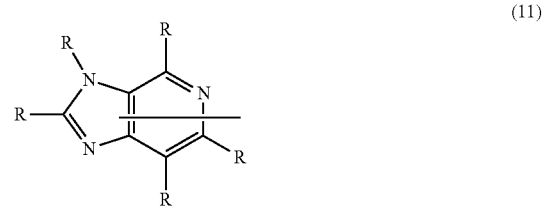
(11)

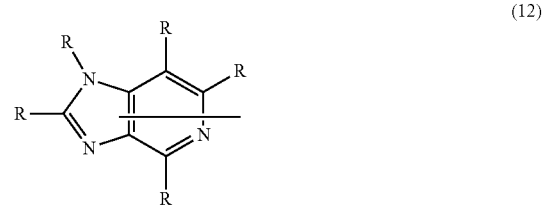
(12)

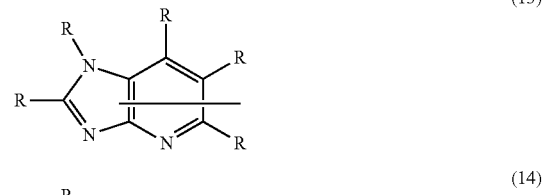
(13)

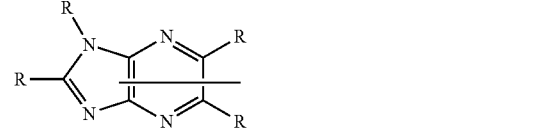
(14)

-continued

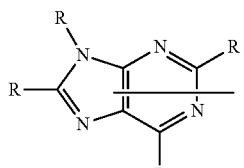
(15)

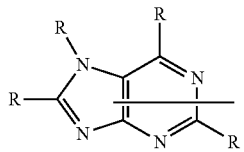
(16)

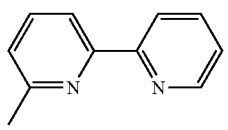
(I)

wherein any one of the R groups that substitutes the heterocyclic skeleton is a single bond and is bonded to $L_1$, and the other R groups are independently a hydrogen atom, an alkyl group, an alkylsilyl group, a halogenated alkyl group, a phenyl group, a naphthyl group, a phenanthryl group, a biphenyl group, a terphenyl group, a chrysenyl group, a benzophenanthryl group, a benzanthryl group, a fluorenyl group and a fluoranthenyl group, a cycloalkyl group, an alkoxy group, a heterocyclic group, an aralkyl group, an aryloxy group, an arylthio group, an alkoxycarbonyl group, a halogen atom, a hydroxyl group, a nitro group, a cyano group, a carboxyl group, or a dibenzofuranyl group; or at least two adjacent groups thereof are combined to form a saturated or unsaturated ring; and a is an integer of 1 to 4, and b is 1.

10. The nitrogen-containing heterocyclic derivative of claim 9, wherein a is 1.

11. The nitrogen-containing heterocyclic derivative of claim 9, which is a material adapted for an organic electroluminescence device.

12. The nitrogen-containing heterocyclic derivative of claim 11, which is a material adapted for a blocking layer of an organic electroluminescence device.

13. An organic electroluminescence device, comprising an anode, an emitting layer, a blocking layer and a cathode sequentially, wherein the blocking layer comprising the nitrogen-containing heterocyclic derivative of claim 9.

14. An organic electroluminescence device, comprising an electron-injecting layer and/or an electron-transporting layer between an emitting layer and a cathode, wherein at least one layer of the electron-injecting layer and the electron-transporting layer comprising the nitrogen-containing heterocyclic derivative of claim 9.

15. The organic electroluminescence device of claim 13, wherein the emitting layer comprises an anthracene derivative represented by formula (41):

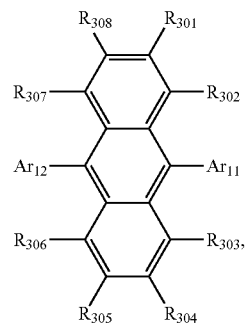
(41)

wherein $Ar_{11}$ and $Ar_{12}$ are independently a substituted or unsubstituted aryl group having 6 to 30 ring carbon atoms or a substituted or unsubstituted heterocyclic group having 5 to 30 ring atoms; and $R_{301}$ to $R_{308}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms.

16. The organic electroluminescence device of claim 15, wherein the emitting layer comprising the anthracene derivative represented by the formula (41) is adjacent to the blocking layer comprising the nitrogen-containing heterocyclic derivative.

17. A nitrogen-containing heterocyclic derivative represented by formula (33):

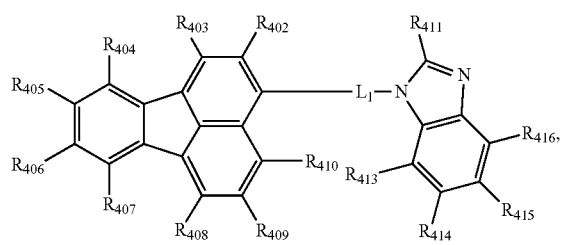
(33)

wherein:

$R_{402}$ to $R_{416}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted alkylamino group, a substituted or unsubstituted arylamino group, a substituted or unsubstituted aryl group having 6 to 30 ring carbon atoms or a substituted or unsubstituted heterocyclic group having 5 to 30 ring atoms; and $L_1$ is a single bond, a substituted or unsubstituted di-valent hydrocarbon group having 6 to 30 ring carbon atoms or a di-valent heterocyclic group having 5 to 30 ring atoms, provided that $L_1$, and $R_{402}$ to $R_{416}$ are not an anthracene containing group.

18. The nitrogen-containing heterocyclic derivative of claim 17, which is a material adapted for an organic electroluminescence device.

19. The nitrogen-containing heterocyclic derivative of claim 18, which is a material adapted for a blocking layer of an organic electroluminescence device.

20. An organic electroluminescence device, comprising an anode, an emitting layer, a blocking layer, and a cathode sequentially, wherein the blocking layer comprises the nitrogen-containing heterocyclic derivative of claim 17.

21. An organic electroluminescence device, comprising an electron-injecting layer and/or an electron-transporting layer between an emitting layer and a cathode, wherein at least one layer of the electron-injecting layer and the electron-transporting layer comprising the nitrogen-containing heterocyclic derivative of claim 17.

22. The organic electroluminescence device of claim 20, wherein the emitting layer comprises an anthracene derivative represented by formula (41):

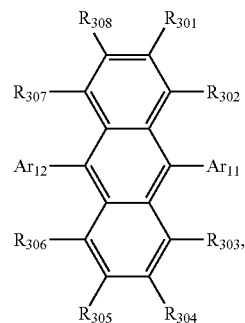

(41)

wherein $Ar_{11}$ and $Ar_{12}$ are independently a substituted or unsubstituted aryl group having 6 to 30 ring carbon atoms or a substituted or unsubstituted heterocyclic group having 5 to 30 ring atoms; and $R_{301}$ to $R_{308}$ are independently a hydrogen atom, a fluorine atom, a substituted or unsubstituted alkyl group having 1 to 10 carbon atoms, a substituted or unsubstituted cycloalkyl group having 3 to 10 carbon atoms, a substituted or unsubstituted alkylsilyl group having 3 to 30 carbon atoms, a substituted or unsubstituted arylsilyl group having 8 to 30 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 30 ring carbon atoms or a substituted or unsubstituted heterocyclic group having 5 to 30 ring atoms.

23. The organic electroluminescence device of claim 22, wherein the emitting layer comprising the anthracene derivative represented by the formula (41) is adjacent to the blocking layer comprising the nitrogen-containing heterocyclic derivative.

* * * * *